(12) United States Patent
Yoon et al.

(10) Patent No.: US 10,317,406 B2
(45) Date of Patent: Jun. 11, 2019

(54) SYSTEM FOR DETECTING RARE CELLS

(71) Applicant: The Regents of the University of Michigan, Ann Arbor, MI (US)

(72) Inventors: Hyeun Joong Yoon, Brookings, SD (US); Apoorv Shanker, Ann Arbor, MI (US); Jinsang Kim, Ann Arbor, MI (US); Sunitha Nagrath, Ann Arbor, MI (US); Vasudha Murlidhar, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 327 days.

(21) Appl. No.: 15/091,830

(22) Filed: Apr. 6, 2016

(65) Prior Publication Data
US 2016/0291019 A1    Oct. 6, 2016

Related U.S. Application Data

(60) Provisional application No. 62/245,594, filed on Oct. 23, 2015, provisional application No. 62/178,318, filed on Apr. 6, 2015.

(51) Int. Cl.
*G01N 33/543* (2006.01)
*G01N 33/574* (2006.01)
(Continued)

(52) U.S. Cl.
CPC .......... *G01N 33/574* (2013.01); *C08L 33/26* (2013.01); *G01N 33/543* (2013.01);
(Continued)

(58) Field of Classification Search
None
See application file for complete search history.

(56) References Cited

U.S. PATENT DOCUMENTS 5,376,252 A    12/1994   Ekstrom et al.
5,770,528 A     6/1998   Mumick et al.
(Continued)

FOREIGN PATENT DOCUMENTS

EP    1 214 361 A    2/2001
EP    2 335 075 A    3/2010
(Continued)

OTHER PUBLICATIONS

Vancoillie et al., Thermoresponsive poly(oligo ethylene glycol acrylates), Jun. 2014, Progress in Polymer Science, vol. 39, Issue 6, pp. 1074-1095 (Year: 2014).*

(Continued)

*Primary Examiner* — Erik B Crawford
(74) *Attorney, Agent, or Firm* — Howard & Howard Attorneys PLLC

(57) ABSTRACT

A system for detecting rare cells in a fluid is disclosed. The system includes a substrate and a mixture disposed on the substrate and including a carrier and a thermo-responsive polymer for capture and release of the rare cells. Also disclosed is a method for detecting rare cells in a fluid using a system including a substrate and a mixture that is disposed on the substrate. The mixture includes a carrier and a thermo-responsive polymer. The method includes providing the system and introducing a sample of fluid containing the rare cells into the system such that the sample interacts with the carrier for capturing the rare cells.

12 Claims, 32 Drawing Sheets
(5 of 32 Drawing Sheet(s) Filed in Color)

(51) Int. Cl.
  *G01N 33/545* (2006.01)
  *C08L 33/26* (2006.01)
(52) U.S. Cl.
  CPC ..... *G01N 33/545* (2013.01); *G01N 33/54353* (2013.01); *C08L 2203/02* (2013.01); *C12N 2539/10* (2013.01)

(56) References Cited

U.S. PATENT DOCUMENTS

| | | | |
|---|---|---|---|
| 5,776,487 | A | 7/1998 | Maxfield Wilson et al. |
| 6,485,690 | B1 | 11/2002 | Pfost et al. |
| 6,803,019 | B1 | 10/2004 | Bjornson et al. |
| 7,179,867 | B2 | 2/2007 | Chang et al. |
| 7,332,288 | B2 | 2/2008 | Terstappen et al. |
| 7,846,393 | B2 | 12/2010 | Tai et al. |
| 8,548,219 | B2 | 10/2013 | Ortyn et al. |
| 9,140,697 | B2 | 9/2015 | Tseng et al. |
| 2004/0005582 | A1 | 1/2004 | Shipwash |
| 2004/0137300 | A1 | 7/2004 | Gemmen et al. |
| 2005/0181463 | A1 | 8/2005 | Rao et al. |
| 2006/0160243 | A1 | 7/2006 | Tang et al. |
| 2007/0224591 | A1 | 9/2007 | Gui et al. |
| 2007/0263477 | A1 | 11/2007 | Sudarsan et al. |
| 2008/0267845 | A1 | 10/2008 | Hoglund et al. |
| 2009/0303472 | A1 | 12/2009 | Zhao et al. |
| 2010/0028681 | A1 | 2/2010 | Dai et al. |
| 2010/0068105 | A1 | 3/2010 | Green |
| 2010/0255479 | A1 | 10/2010 | Mikolajczyk et al. |
| 2010/0255581 | A1* | 10/2010 | Naqvi ............... A61L 27/16 435/396 |
| 2011/0091864 | A1 | 4/2011 | Karlsson et al. |
| 2011/0096327 | A1 | 4/2011 | Papautsky et al. |
| 2011/0104732 | A1 | 5/2011 | Lucic et al. |
| 2011/0189650 | A1 | 8/2011 | Ayliffe et al. |
| 2012/0003711 | A1 | 1/2012 | Tseng et al. |
| 2012/0040843 | A1 | 2/2012 | Ducree et al. |
| 2012/0209116 | A1 | 8/2012 | Hossack et al. |
| 2012/0300576 | A1 | 11/2012 | Li et al. |
| 2013/0129829 | A1 | 5/2013 | He |
| 2013/0236881 | A1 | 9/2013 | Spatz et al. |
| 2013/0261266 | A1* | 10/2013 | Bunyard ............... C08F 299/00 525/292 |
| 2014/0186426 | A1 | 7/2014 | Tseng et al. |
| 2014/0315213 | A1 | 10/2014 | Nagrath et al. |
| 2015/0285808 | A1 | 10/2015 | Nagrath et al. |
| 2015/0293010 | A1 | 10/2015 | Nagrath et al. |
| 2015/0337128 | A1* | 11/2015 | Gray ............... C12M 25/14 514/772.1 |

FOREIGN PATENT DOCUMENTS

| | | |
|---|---|---|
| WO | WO 01/09198 A1 | 2/2001 |
| WO | WO 2009/051734 A1 | 4/2009 |
| WO | WO 2010/028160 A1 | 3/2010 |
| WO | WO 2010/108003 A2 | 9/2010 |
| WO | WO 2010/124227 A2 | 10/2010 |
| WO | WO 2011/049963 A2 | 4/2011 |
| WO | WO 2011/094279 A1 | 8/2011 |
| WO | WO 2012/094642 A2 | 7/2012 |
| WO | WO 2013/049636 A1 | 4/2013 |
| WO | WO 2013/116523 A1 | 8/2013 |
| WO | WO 2014/022581 A1 | 2/2014 |
| WO | WO 2014/036951 A1 | 3/2014 |
| WO | WO 2014/072465 A1 | 5/2014 |
| WO | WO 2014/120265 A1 | 8/2014 |

OTHER PUBLICATIONS

Lu et al. "A Graphene Platform for Sensing Biomolecules" Angew Chem Int Ed Engl 48, 2009, pp. 4785-4787.

Maheswaran et al. "Detection of mutations in EGFR in circulating lung-cancer cells" The New England Journal of Medicine, vol. 359, Jul. 2008, pp. 366-377.

Mohanty et al. "Graphene-based single-bacterium resolution biodevice and DNA transistor: interfacing graphene derivatives with nanoscale and microscale biocomponents" Nano Lett 8, 2008, pp. 4469-4476.

Molloy et al. "The prognostic significance of tumour cell detection in the peripheral blood versus the bone marrow in 733 early-stage breast cancer patients" Breast Cancer Research 13, R61, 2011, 11 pages.

Mueller et al. "Prognostic impact of circulating tumor cells assessed with CellSearch System(TM) and AdnaTest Breast(TM) in metastatic breast cancer patients: the DETECT study" Breast Cancer Research 14:R118, 2012, 8 pages.

Nagrath et al. "Isolation of rare circulating tumour cells in cancer patients by microchip technology" Nature 450, 2007, pp. 1235-1239.

Nejlund et al. "In vitro detection of CTCs with the CytoTrack method", a poster presentation retrieved from www.cytotrack.dk/page12 on Apr. 16, 2014, 1 page.

Novoselov et al. "Two-dimensional gas of massless Dirac fermions in graphene" Nature, vol. 438, Issue 7065, Nov. 2005, pp. 197-200.

Nygaard et al. "Method comparison of CTC detection with CytoTrack and CellSearch", a poster presentation retrieved from www.cytotrack.dk/page12 on Apr. 16, 2014, 1 page.

Pantel et al. "Detection, clinical relevance and specific biological properties of disseminating tumour cells" Nat Rev Cancer 8, 2008, pp. 329-340.

Park et al. "Graphene oxide papers modified by divalent ions-enhancing mechanical properties via chemical cross-linking" ACS Nano 2, 2008, pp. 572-578.

Arya et al., "Enrichment, detection and clinical significance of circulating tumor cells", Lab on a Chip, 13, 2013, pp. 1995-2027.

Brongersma et al., "Plasmon-induced hot carrier science and technology", Nat. Nano. 10, 2015, pp. 25-34.

Cecchet et al., "One Step Growth of Protein Antifouling Surfaces: Monolayers of Poly(ethylene oxide) (PEO) Derivatives on Oxidized and Hydrogen-Passivated Silicon Surfaces", Langmuir: the ACS Journal of Surfaces and Colloids, 22, 2006, pp. 1173-1181.

Chaudhuri et al., "Myoblast differentiation of human mesenchymal stem cells on graphene oxide and electrospun graphene oxide—polymer composite fibrous meshes: importance of graphene oxide conductivity and dielectric constant on their biocompatibility", Biofabrication, 7, 2015, pp. 1-13.

Cunliffe et al., "Bacterial adsorption to thermoresponsive polymer surfaces", Biotechnology Letters 22, 2000, pp. 141-145.

Das et al., "Graphene-Based Polymer Composites and Their Applications", Polymer-Plastics Technology and Engineering, 52, 2013, pp. 319-331.

Gupta et al., "Cancer Metastasis: Building a Framework", Massague, Cell 127, 2006, pp. 679-695.

Hatch et al., "Engineered Alginate Hydrogels for Effective Microfluidic Capture and Release of Endothelial Progenitor Cells from Whole Blood", Langmuir, 27, 2011, pp. 4257-4264.

Hoshino et al., "Preparation of a New Thermo-Responsive Adsorbent with Maltose as a Ligand and Its Application to Affinity Precipitation", Biotechnol Bioeng., 60, 1998, pp. 568-579.

Huber et al., "Programmed Adsorption and Release of Proteins in a Microfluidic Device", Science 301, 2003, pp. 352-355.

Hu et al., "Quantum-Dot-Tagged Reduced Graphene Oxide Nanocomposites for Bright Fluorescence Bioimaging and Photothermal Therapy Monitored in Situ", Advanced Materials, 24, 2012, pp. 1748-1754.

Ithimakin et al., "HER2 Drives Luminal Breast Cancer Stem Cells in the Absence of HER2 Amplification: Implications for Efficacy of Adjuvant Trastuzumab", Cancer Research, 73, 2013, pp. 1635-1646.

Kamande et al., "Modular Microsystem for the Isolation, Enumeration, and Phenotyping of Circulating Tumor Cells in Patients with Pancreatic Cancer", Analytical Chemistry 85, 2013, pp. 9092-9100.

Kim et al., "Graphene Oxide—Polyethylenimine Nanoconstruct as a Gene Delivery Vector and Bioimaging Tool", Bioconjugate Chemistry, 22, 2011, pp. 2558-2567.

Kumar et al., "Chemical Functionalization of Graphene to Augment Stem Cell Osteogenesis and Inhibit Biofilm Formation on Polymer

(56) References Cited

OTHER PUBLICATIONS

Composites for Orthopedic Applications", ACS Applied Materials & Interfaces, 7, 2015, pp. 3237-3252.
Li et al., "Organo- and Water-Dispersible Graphene Oxide-Polymer Nanosheets for Organic Electronic Memory and Gold Nanocomposites", Journal of Physical Chemistry C, 114, 2010, p. 12742-12748.
Liu et al., "Hydrophobic Interaction-Mediated Capture and Release of Cancer Cells on Thermoresponsive Vanostructured Surfaces", Advanced Materials 25, 2013, pp. 922-927.
Maheswaran et al., "Circulating tumor cells: a window into cancer biology and metastasis", Current Opinion in Genetics & Development 20, 2010, pp. 96-99.
Nakamura et al., "Uptake and release of budesonide from mucoadhesive, pH-sensitive copolymers and their application to nasal delivery", Journal of Controlled Release 61, 1999, pp. 329-335.
Nitschke et al., "Thermo-responsive poly(NiPAAm-co-DEGMA) substrates for gentle harvest of human corneal endothelial cell sheets", Journal of Biomedical Materials Research Part A, 80A, 2007, pp. 1003-1010.
Pant et al., "Processing and characterization of electrospun graphene oxide/polyurethane composite nanofibers for stent coating", Chemical Engineering Journal, 270, 2015, pp. 336-342.
Paterlini-Brechot et al., "Circulating tumor cells (CTC) detection: Clinical impact and future directions", Cancer Letters 253, 2007, pp. 180-204.
Reategui et al., "Tunable Nanostructured Coating for the Capture and Selective Release of Viable Circulating Tumor Cells", Adv. Mater, 27, 2015, pp. 1593-1599.
Sahoo et al., "Functionalized carbon nanomaterials as nanocarriers for loading and delivery of a poorly water-soluble anticancer drug: a comparative study", Chemical Communications, 47, 2011, pp. 5235-5237.
Stile et al., "Thermo-Responsive Peptide-Modified Hydrogels for Tissue Regeneration", Biomacromolecules, 2, 2001, pp. 185-194.
Sun et al., "Nano-Graphene Oxide for Cellular Imaging and Drug Delivery", Nano Research 1, 2008, pp. 203-212.
Thampi et al., "Mechanical characterization of high-performance graphene oxide incorporated aligned fibroporous poly(carbonate urethane) membrane for potential biomedical applications", Journal of Applied Polymer Science, 2015, pp. 132-139.
Wang et al., "Nanostructured substrates for isolation of circulating tumor cells", Nano Today 8, 2013, pp. 374-387.
Wu et al., "Supercapacitors Based on Flexible Graphene/Polyaniline Nanofiber Composite Films", ACS Nano, 4, 2010, pp. 1963-1970.
Yoon et al., "Emerging Role of Nanomaterials in Circulating Tumor Cell Isolation and Analysis", ACS Nano 8, 2014, pp. 1995-2017.
Zhang et al., "Microfluidics and cancer: are we there yet?", Biomedical Microdevices 15, 2013, pp. 595-609.
Zhuang et al., "Conjugated-Polymer-Functionalized Graphene Oxide: Synthesis and Nonvolatile Rewritable Memory Effect", Adv. Mater., 22, 2010, pp. 1731-1735.
Bhagat et al., Inertial Microfluidics for Continuous Particle Filtration and Extraction, Microfluidics and Nanofluidics, vol. 7, No. 2, 2008, pp. 217-226.
Gossett et al., "Label-Free Cell Separation and Sorting in Microfluidic Systems", Analytical and Bioanalytical Chemistry, vol. 397, No. 8, 2010, pp. 3249-3267.
Yu et al., "RNA sequencing of pancreatic circulating tumour cells implicates WNT signalling in metastasis", Nature, vol. 487, Jul. 26, 2012, pp. 510-514.
Zhang et al. "Binding Affinities/Avidities of Antibody-Antigen Interactions: Quantification and Scale-Up Implications", Biotechnology and Bioengineering, vol. 95, No. 5, Dec. 5, 2006, pp. 812-829.
Zhang et al. "Electrospun TiO2 Nanofiber-Based Cell Capture Assay for Detecting Circulating Tumor Cells from Colorectal and Gastric Cancer Patients", Advanced Materials 24, 2012, pp. 2756-2760.
Zhang et al. "Experimental observation of the quantum Hall effect and Berry's phase in graphene", Nature, vol. 438, Issue 7065, Nov. 2005, pp. 201-204.
Zheng et al. "A high-performance microsystem for isolating circulating tumor cells", Lab Chip, The Royal Society of Chemistry, 2011, pp. 3269-3276.
Zheng et al. "Membrane microfilter device for selective capture, electrolysis and genomic analysis of human circulating tumor cells", Journal of Chromatography A 1162, pp. 154-161 (2007).
"Circulating tumor cells: the Grand Challenge", Lab Chip, The Royal Society of Chemistry, 2011, pp. 375-377.
International Search Report for Application No. PCT/US2012/058013 dated Feb. 14, 2013, 4 pages.
Adams et al. "Highly efficient circulating tumor cell isolation from whole blood and label-free enumeration using polymer-based microlluidics with an integrated conductivity sensor", J. Am. Chemical Society, 130, 2007, pp. 8633-8641.
Allard et al. "Tumor Cells Circulate in the Peripheral Blood of All Major Carcinomas but not in Healthy Subjects or Patients With Nonmalignant Diseases", Clinical Cancer Research 10, 2004, pp. 6897-6904.
Kuntaegowdanahalli et al., "Inertial Microfluidics for Continuous Particle Separation in Spiral Microchannels", Lab on a Chip, vol. 9, 2009, pp. 2973-2980.
Andreopoulou et al. "Comparison of assay methods for detection of circulating tumor cells in metastatic breast cancer: AdnaGen AdnaTest Breast Cancer Select/Detect(TM) versus Veridex CellSearch(TM) system", Int. J. Cancer: 130, 2012, pp. 1590-1597.
Antolovic et al. "Heterogeneous detection of circulating tumor cells in patients with colorectal cancer by immunomagnetic enrichment using different EpCAM-specific antibodies", BMC Biotechnology 10, 35, 2010, 8 pages.
Barreto et al. "Nanomaterials: Applications in Cancer Imaging and Therapy" Advanced Materials 23, 2011, pp. H18-H40.
Bednarz-Knoll et al. "Plasticity of disseminating cancer cells in patients with epithelial malignancies" Cancer and Metastasis Reviews, Jun. 26, 2012, 15 pages.
Chen et al. "Aptamer-Enabled Efficient Isolation of Cancer Cells from Whole Blood Using a Microfluidic Device", Anal. Chem., 1:84(9), May 1, 2012, pp. 4199-4206.
Cohen et al. "Relationship of Circulating Tumor Cells to Tumor Response, Progression-Free Survival, and Overall Survival in Patients With Metastatic Colorectal Cancer" Journal of Clinical Oncology 26, 2008, pp. 3213-3221.
Cristofanilli et al. "Circulating Tumor Cells, Disease Progression, and Survival in Metastatic Breast Cancer", New England Journal of Medicine 351, 2004, pp. 781-791.
De Bono et al. "Circulating Tumor Cells Predict Survival Benefit from Treatment in Metastatic Castration-Resistant Prostate Cancer", Clinical Cancer Research 14, 2008, pp. 6302-6309.
Dikin et al. "Preparation and characterization of graphene oxide paper", Nature 448, 2007, pp. 457-460.
Dobrovolskaia et al. "Immunological properties of engineered nanomaterials", Nat Nano 2, 2007, pp. 469-478.
Dreyer et al. "The chemistry of graphene oxide", Chemical Society Reviews 39, 2010, pp. 228-240.
Eda et al. "Large-area ultrathin films of reduced graphene oxide as a transparent and flexible electronic material", Nat, Nano 3, 2008, pp. 270-274.
Farace et al. "A direct comparison of CellSearch and ISET for circulating tumour-cell detection in patients with metastic carcinomas", British Journal of Cancer 105, 2011, pp. 847-853.
Fehm et al. "Detection and characterization of circulating tumor cells in blood of primary breast cancer patients by RT-PCR and comparison to status of bone marrow disseminated cells", Breast Cancer Research 11:R59, 2009, 9 pages.
Fehm et al. "HER2 status of circulating tumor cells in patients with metastatic breast cancer: a prospective, multicenter trial", Breast Cancer Res. Treat, 124, 2010, pp. 403-412.
Geim et al. "The rise of graphene", Nature Materials, vol. 6, 2007, pp. 183-191.
Gleghorn et al. "Capture of circulating tumor cells from whole blood of prostate cancer patients using geometrically enhanced

(56) References Cited

OTHER PUBLICATIONS differential immunocapture (GEDI) and a prostate-specific antibody", Lab on a Chip 10, 2010, pp. 27-29.
Hanahan et al., "Hallmarks of Cancer: The Next Generation", Cell, 144, Mar. 4, 2011, pp. 646-674.
Haugaard et al. "In vitro detection of CTCs with the CytoTrack method", a poster presentation retrieved from www.cytotrack.dk/page12 on Apr. 16, 2014, 1 page.
Hayes et al. "Circulating Tumor Cells at Each Follow-up Time Point during Therapy of Metastatic Breast Cancer Patients Predict Progression-Free and Overall Survival", Clin Cancer Res 12, 2006, pp. 4218-4224.
Hillig et al. "In vitro validation of an ultra-sensitive scanning fluorescence microscope for analysis of Circulating Tumor Cells", APMIS 2013 published by John Wiley & Sons Ltd, 7 pages.
Hillig et al. "Monitoring CTC in metastatic breast cancer patients using the CytoTrack method", a poster presentation retrieved from www.cytrotrack.dk/page12 on Apr. 16, 2014, 1 page.
Hummers et al. "Preparation of graphitic oxide", Journal of the American Chemical Society, vol. 80, Mar. 1958, p. 1339.
Amnis Corporation, "Brochure for ImageStreamX, Imaging Flow Cytometer", 2012, 16 pages.
Jung et al. "A graphene oxide based immuno-biosensor for pathogen detection", Angew. Chem. 122, 2010, pp. 5844-5847.
Kaiser "Cancer's Circulation Problem", Science 327, 2010, pp. 1072-1074.
Kim et al. "Nanomedicine", New England Journal of Medicine 363, 2010, pp. 2434-2443.
Kurkuri et al. "Plasma functionalized PDMS microfluidic chips: towards point-of-care capture of circulating tumor cells", Journal of Materials Chemistry 21, 2011, pp. 8841-8848.
Lee et al. "Nanowire Substrate-Based Laser Scanning Cytometry for Quantitation of Circulating Tumor Cells", Nano Letters 12, 2012, pp. 2697-2704.
Li et al. "Processable aqueous dispersions of graphene nanosheets", Nature Nanotechnology, vol. 3, 2008, pp. 101-105.
Li et al. "Highly conducting graphene sheets and Langmuir-Blodgett films", Nat. Nano. 3, 2008, pp. 538-542.
Lin et al. "Portable Filter-Based Microdevice for Detection and Characterization of Circulating Tumor Cells", Clinical Cancer Research 16, 2010, pp. 5011-5018.
Liu et al. "Biocompatable graphene oxide-based glucose biosensors", Langmuir 26(9), 2010, pp. 6158-6160.
Liu et al. "Supramolecular chemistry on water-soluble carbon nanotubes for drug loading and delivery", ACS Nanovol. 1, 2007, pp. 50-56.
Liu et al. "Intercalation of Organic Ammonium Ions into Layered Graphite Oxide", Langmuir 18, 2002, pp. 4926-4932.
Liu et al. "PEGylated nanographene oxide for delivery of water-insoluble cancer drugs", J Am Chem Soc 130, 2008, pp. 10876-10877.
Liu et al. "Preparation of carbon nanotube bioconjugates for biomedical applications", Nat. Protocols 4, 2009, pp. 1372-1381.
Loh et al. "Graphene oxide as a chemically tunable platform for optical applications", Nat Chem 2, 2010, pp. 1015-1024.
Lopez-Riquelme et al. "Imaging cytometry for counting circulating tumor cells: comparative analysis of the CellSearch vs. ImageStream systems", APMIS, 121, published by John Wiley & Sons Ltd., 2013, pp. 1139-1143.
English language abstract for WO 2014/036951 extracted from espacenet.com database on May 25, 2016, 2 pages.
Aceto et al., "Circulating tumor cell clusters are oligoclonal precursors of breast cancer metastasis," Cell, 158, Aug. 28, 2014, pp. 1110-1122.
Aguirre-Ghiso et al., "Targeting dormant cancer," Nature Medicine, vol. 19, No. 3, Mar. 2013, pp. 276-277.
Alix-Panabieres et al., "Challenges in circulating tumour cell research", Nature Reviews, Cancer, vol. 14, Sep. 2014, pp. 623-631.

Baccelli et al., "Identification of a population of blood circulating tumor cells from breast cancer patients that initiates metastasis in a xenograft assay", Nature Biotechnology, vol. 31, No. 6, Jun. 2013, pp. 539-544.
Bhagat et al., "Pinched flow coupled shear-modulated inertial microfluidics for high-throughput rare blood cell separation", Lab on a Chip, The Royal Society of Chemistry, www.rsc.org/loc 2011, pp. 1870-1878.
Bissolati et al., "Portal vein-circulating tumor cells predict liver metastases in patients with resectable pancreatic cancer", Tumour Biology: The Journal of the International Society for Oncodevelopmental Biology and Medicine, 2015, pp. 991-996.
Brechot et al., "Circulating tumor cells (CTC) detection: Clinical impact and future directions", Science Direct, www.sciencedirect.com, 2006, pp. 180-204.
Carlsson et al., "Circulating tumor microemboli diagnostics for patients with non-small-cell lung cancer", Journal of Thoracic Oncology: Official Publication of the International Association for the Study of Lung Cancer, vol. 9, No. 8, Aug. 2014, pp. 1111-1119.
Dickson et al., "Efficient capture of circulating tumor cells with a novel immunocytochemical microfluidic device" AIP Biomicrofluidics, 2011, pp. 1-16.
Dharmasiri et al. "Highly efficient capture and enumeration of low abundance prostate cancer cells using prostate-specific membrane antigen aptamers immobilized to a polymeric microfluidic device", Electrophoresis, 2009, pp. 3289-3300.
Dong et al. "Microfluidics and Circulating Tumor Cells", The Journal of Molecular Diagnostics, 2012, pp. 1-9.
Fan et al. "Clinical significance of circulating tumor cells detected by an invasion assay in peripheral blood of patients with ovarian cancer", Gynecologic Oncology 112, 2009, pp. 185-191.
Funaki et al., "Novel approach for detection of isolated tumor cells in pulmonary vein using negative selection method: morphological classification and clinical implications", European Journal of Cardio-Thoracic Surgery: Official Journal of the European Association for Cardio-Thoracic Surgery, vol. 40, 2011, pp. 322-327.
Funaki et al., "Significance of tumour vessel invasion in determining the morphology of isolated tumour cells in the pulmonary vein in non-small-cell lung cancer", European Journal of Cardio-Thoracic Surgery: Official Journal of the European Association for Cardio-thoracic Surgery, vol. 43, 2013, pp. 1126-1130.
Haber et al., "Blood-based analyses of cancer: circulating tumor cells and circulating tumor DNA" Cancer Discovery, Jun. 2014, pp. 650-651.
Hashimoto et al., "Significant increase in circulating tumour cells in pulmonary venous blood during surgical manipulation in patients with primary lung cancer", Interactive Cardiovascular and Thoracic Surgery, vol. 18, 2014, pp. 775-783.
Hirsch et al., "Early detection of lung cancer: clinical perspectives of recent advances in biology and radiology", Clinical Cancer Research: An Official Journal of the American Association for Cancer Research, vol. 7, Jan. 2001, pp. 5-22.
Hoshino et al. "Microchip-based immunomagnetic detection of circulating tumor cells", Lab Chip, 2011, pp. 3449-3457.
Hou et al. "Capture and Stimulated Release of Circulating Tumor Cells on Polymer-Grafted Silicon Nanostructures", Advanced Materials, 2013, pp. 1547-1551.
Hou et al. "Circulating Tumor Cells as a Window on Metastasis Biology in Lung Cancer", The American Journal of Pathology, vol. 178, No. 3, Mar. 2011, pp. 989-996.
Hou et al., "Clinical significance and molecular characteristics of circulating tumor cells and circulating tumor microemboli in patients with small-cell lung cancer", Journal of Clinical Oncology: Official Journal of the American Society of Clinical Oncology, vol. 30, No. 5, Feb. 10, 2012, pp. 525-532.
Hou et al. "Isolation and retrieval of circulating tumor cells using centrifugal faces", Scientific Reports, 2013, pp. 1-8.
Iniesta et al., "Biological and clinical significance of MMP-2, MMP-9, TIMP-1 and TIMP-2 in non-small cell lung cancer", Oncology Reports, vol. 17, 2007, pp. 217-223.
Karabacak et al. "Microfluidic, marker-free isolation of circulating tumor cells from blood samples", Nature Protocols, vol. 9, No. 3, 2014, pp. 694-710.

(56) References Cited

OTHER PUBLICATIONS

Ke et al. "Programming Thermoresponsiveness of Nano Velcro Substrates Enables Effective Purification of Circulating Tumor Cells in Lung Cancer Patients", American Chemical Society, vol. 9, No. 1, 2015, pp. 62-70.
Khoja et al. "A pilot study to explore circulating tumour cells in pancreatic cancer as a novel biomarker" British Journal of Cancer, 2012, pp. 508-516.
Krebs et al., "Analysis of circulating tumor cells in patients with non-small cell lung cancer using epithelial marker-dependent and -independent approaches", Journal of Thoracic Oncology: Official Publication of the International Association for the Study of Lung Cancer, vol. 7, No. 2, 2012, pp. 306-315.
Koukourakis et al., "Enhanced expression of SPARC/osteonectin in the tumor-associated stroma of non-small cell lung cancer is correlated with markers of hypoxia/acidity and with poor prognosis of patients", Cancer Research, vol. 63, Sep. 1, 2003, pp. 5376-5380.
Lecharpentier et al., "Detection of circulating tumour cells with a hybrid (epithelial/mesenchymal) phenotype in patients with metastatic non-small cell lung cancer", British Journal of Cancer, vol. 105, 2011, pp. 1338-1341.
Lin et al. "Nanostructure Embedded Microchips for Detection, Isolation, and Characterization of Circulating Tumor Cells", Account of Chemical Research, 2014, pp. 2941-2950.
Liotta et al., "The significance of hematogenous tumor cell clumps in the metastatic process", Cancer Research, vol. 36, Mar. 1976, pp. 889-894.
Liu et al. "High throughout capture of circulating tumor cells using an integrated microfluidic system", Biosensors and Bioelectronics, 2013, pp. 113-119.
Livak et al., "Analysis of relative gene expression data using real-time quantitative PCR and the 2(-Delta Delta C(T)) Method", Methods, vol. 25, 2001, pp. 402-408.
Lortent-Tieulentet al., "International trends in lung cancer incidence by histological subtype: adenocarcinoma stabilizing in men but still increasing in women", Lung Cancer, vol. 84, 1014, pp. 13-22.
Luo et al., "Epithelial-mesenchymal plasticity of breast cancer stem cells: implications for metastasis and therapeutic resistance", Current Pharmaceutical Design, vol. 21, 2015, pp. 1301-1310.
Maheswaran et al., "Detection of Mutations in EGFR in Circulating Lung-Cancer Cells", The New England Journal of Medicine, Jul. 24, 2008, pp. 366-377.
Marrinucci et al., "Case study of the morphologic variation of circulating tumor cells", Human Pathology, vol. 38, 2007, pp. 514-519.
Marrinucci et al., "Cytomorphology of circulating colorectal tumor cells:a small case series", Journal of Oncology, Article I.D. 861341, 2010, pp. 1-7.
Mikolajczyk et al., "Detection of EpCAM-Negative and Cytokeratin-Negative Circulating Tumor Cells in Peripheral Blood", Journal of Oncology, 2011, pp. 1-10.
Miller et al. "Significance of Circulating Tumor Cells Detected by the Cellsearch System in Patients with Metastatic Breast Colorectal and Prostate Cancer", Journal of Oncology, Hindawi Publishing Corporation, vol. 2010, Article ID 617421, pp. 1-8.
Mittal et al. "Antibody-Functionalized Fluid-Permeable Surfaces for Rolling Cell Capture at High Flow Rates", Biophysical Journal, vol. 102, Feb. 2012, pp. 721-730.
Mittal et al. "Discontinuous Nanoporous Membranes Reduce Non-Specific Fouling for Immunoaffinity Cell Capture" Small, vol. 9, No. 24, 2013, pp. 4207-4214.
Murlidhar et al., "A radial flow microfluidic device for ultra-high-throughput affinity-based isolation of circulating tumor cells", Small, vol. 10, No. 23, 2014, pp. 4895-4904.
Nanguzgambo et al., Immunochemistry and lung cancer: application in diagnosis, prognosis and targeted therapy:, Oncology, vol. 80, 2011 pp. 247-256.
Okumura et al., "Circulating Tumor Cells in Pulmonary Venous Blood of Primary Lung Cancer Patients", The Annals of thoracic surgery, vol. 87, 2009, pp. 1669-1675.
Ozkumur et al. "Inertial Focusing for Tumor Antigen-Dependent and-Independent Sorting of Rare Circulating Tumor Cells", Science Translational Medicine, vol. 5, Issue 179, Apr. 3, 2013, pp. 1-11.
Pantel et al., "Functional Studies on Viable Circulating Tumor Cells", Clinical Chemistry, vol. 62, No. 2, 2015, pp. 328-334.
Peeters et al., "Circulating tumour cells and lung microvascular tumour cell retention in patients with metastatic breast and cervical cancer", Cancer Letters, vol. 356, 2015, pp. 872-879.
Pirozzi et al., "Prognostic value of cancer stem cells, epithelial-mesenchymal transition and circulating tumor cells in lung cancer", Oncology Reports, vol. 29, 2013, pp. 1763-1768.
Pantel et al., "Circulating Tumour Cells in Cancer Patients: Challenges and Perspectives", Trends. Mol. Med. 2010, 16(9), pp. 398-406.
Park et al. "Chemical methods for the production of graphenes" Nature Nanotechnology, vol. 4, Apr. 2009, pp. 217-224.
Pierce Biotechnology, Inc., "GMBS and Sulfo-GMBS" Rockford, IL, Jul. 2005, retrieved from http://www.piercenet.com/instructions/2161763.pdf on Apr. 16, 2014, 3 pages.
Poveda et al., "Circulating tumor cells predict progression free survival and overall survival in patients with relapsed/recurrent advanced ovarian cancer", Gynecologic Oncology, vol. 122, 2011, pp. 567-572.
Powell et al. "Single Cell Profiling of Circulating Tumor Cells: Transcriptional Heterogeneity and Diversity from Breast Cancer Cell Lines", PLoS one, vol. 7, Issue 5, May 2012, pp. 1-11.
Punnoose et al. "Evaluation of Circulating Tumor Cells and Circulating Tumor DNA in Non-Small Cell Lung Cancer: Association with Clinical Endpoints in a Phase 11 Clinical Trial of Pertuzumab and Erlotinib", Clinical Cancer Research, 2012, pp. 2391-2401.
Punnoose et al. "Molecular Biomarker Analyses Using Circulating Tumor Cells" PLoS One vol. 5, Issue 9, e12517, 2010, 12 pages.
Rahbari et al., "Compartmental differences of circulating tumor cells in colorectal cancer", Annals of Surgical Oncology, vol. 19, 2012, pp. 2195-2202.
Ramanathan et al. "Functionalized graphene sheets for polymer nanocomposites" Nat Nanotechnol 3, 2008 pp. 327-331.
Reddy et al., "Pulmonary venous blood sampling significantly increases the yield of circulating tumor cells in early-stage lung cancer", The Journal of Thoracic and Cardiovascular Surgery, 2015, pp. 852-858.
Riethdorf et al. "Detection of Circulating Tumor Cells in Peripheral Blood of Patients with Metastatic Breast Cancer: A Validation Study of the CellSearch System" Clin Cancer Res 13, 2007, pp. 920-928.
Roy et al. "New directions in thermoresponsive polymers", The Royal Society of Chemistry, 2013, pp. 7214-7243.
Rudin et al. "Phase II Study of Single-Agent Navitoclax (ABT-263) and Biomarker Correlates in Patients with Relapsed Small Cell Lung Cancer", Clinical Cancer Research, Jun. 1, 2012, pp. 3163-3169.
Sarioglu et al., "A microfluidic device for label-free, physical capture of circulating tumor cell clusters", Nature Methods, vol. 12, No. 7, 2015, pp. 685-691.
Schmittgen et al., "Analyzing real-time PCR data by the comparative C(T) method", Nature Protocols, vol. 3, No. 6, 2008, pp. 1101-1108.
Sequist et al., "An Exciting New Tool to Detect Circulating Tumor Cells in Lung Cancer Patients", Journal of Thoracic Oncology, vol. 4, No. 3, Mar. 2009, pp. 281-283.
Shah et al., "Biopolymer System for Cell Recovery from Microfluidic Cell Capture Devices" American Chemical Society Publications, 2012, pp. 3682-3688.
Shao et al. "Graphene based electrochemical sensors and biosensors: A review", Electroanalysis 22, No. 10, 2010, pp. 1027-1036.
Shanker et al., "Microfluidic Device with Polyer-Graphene Oxide Composite Platform for Efficient Capture and Release of Circulating Tumor Cells," University of Michigan, Date: 2015, 1 page.
Sheng et al. "Aptamer-Enabled Efficient Isolation of Cancer Cells from Whole Blood Using a Microfluidic Device" Analytical Chemistry 84, 2012, pp. 4199-4206.
Sienel et al., "Tumour cells in the tumour draining vein of patients with non-small cell lung cancer: detection rate and clinical signifi-

(56) References Cited

OTHER PUBLICATIONS cance", European Journal of Cardio-Thoracic Surgery: Official Journal of the European Association for Cardio-thoracic Surgery, vol. 23, 2003, pp. 451-456.
Smirnov et al., "Global Gene Expression Profiling of Circulating Tumor Cells", American Association for Cancer Research, Jun. 15, 2005, pp. 4993-4997.
Stankovich et al. "Graphene-based composite materials" Nature 442, 2006, pp. 282-286.
Stankovich et al. "Synthesis and exfoliation of isocyanate-treated graphene oxide nanoplatelets" Carbon, vol. 44, 2006, pp. 3342-3347.
Stott et al., "Isolation and characterization of circulating tumor cells from patients with localized and metastatic prostate cancer", Science Translational Medicine, vol. 2, Issue 25, 2010, pp. 1-10.
Sun et al. "Circulating tumor cells: advances in detection methods, biological issues, and clinical relevance" J Cancer Research Clinical Oncology, 2011, pp. 1151-1173.
Sun et al. "Nano-Graphene Oxide for Cellular Imaging and Drug Delivery" Nano Res 1, 2008, pp. 203-212.
Suzuki et al., "Aberrant methylation of SPARC in human lung cancers", British Journal of Cancer, vol. 92, 2005, pp. 942-948.
Ting et al., "Single-cell RNA sequencing identifies extracellular matrix gene expression by pancreatic circulating tumor cells", Cell Reports, vol. 8, 2014, pp. 1905-1918.
Tjensvoll et al. "Circulating tumor cells in pancreatic cancer patients: Methods of detection and clinical implications" Int. J. Cancer: 134, 2014, pp. 1-8.
Tymosiak-Zielinska et al. "Interfacial properties of polycrystalline gold electrodes in tetraalkylammonium electrolytes" Electrochimica Acta 46, 2001, pp. 3073-3082.
Wang et al. "Chemical self-assembly of graphene sheets" Nano Research, vol. 2, Feb. 2009, pp. 336-342.
Wang et al. "Highly efficient capture of circulating tumor cells by using nanostructured silicon substrates with integrated chaotic micromixers", Angewandte Chemmie International Edition, vol. 50, Issue 13, Mar. 4, 2011, pp. 3084-3088 (Mar. 4, 2011).
Wang et al. "Three-Dimensional Nanostructured Substrates toward Efficient Capture of Circulating Tumor Cells" Angewandte Chemie 121, 2009, pp. 9132-9135.
Wei et al. "The assembly of single-layer graphene oxide and graphene using molecular templates" Nano Letters, vol. 8, Aug. 2008, pp. 3141-3145, Aug. 2008.
Wendel et al., "Fluid biopsy for circulating tumor cell identification in patients with early-and late-stage non-small cell lung cancer: a glimpse into lung cancer biology", Physical Biology, vol. 9, 2012, pp. 1-9.
Wicha et al., Circulating tumor cells: not all detected cells are bad and not all bad cells are detected. Journal of Clinical Oncology: Official Journal of the American Society of Clinical Oncology, vol. 29, 2011, pp. 1508-1511.
Wikipedia, "Bovine serum albumin" http://en.wikipedia.org/wiki/Bovine_serum_albumin, retrieved Sep. 29, 2011, 1 Page.
Wikipedia, "Epithelial cell adhesion molecule" http://en.wikipedia.org/wiki/Epithelial_cell_adhesion_moledcule, retrieved Sep. 29, 2011, 1 Page.
Wikipedia, "Phosphate buffered saline" http://en.wikipedia.org/wiki/Phosphate_buffered_saline, retrieved Sep. 29, 2011, 1 page.
Willipinski-Stapelfeldt et al. "Changes in Cytoskeletal Protein Composition Indicative of an Epithelial-Mesenchymal Transition in Human Micrometastatic and Primary Breast Carcinoma Cells" Clinical Cancer Research 11, 2005, 2005, pp. 8006-8014.
Wu et al., "Preliminary investigation of the clinical significance of detecting circulating tumor cells enriched from lung cancer patients", Journal of Thoracic Oncology: Official Publication of the International Association for the Study of Lung Cancer, vol. 4, No. 1, 2009, pp. 30-36.
Xia et al. "An index for characterization of nanomaterials in biological systems" Nat Nano 5, 2010, pp. 671-675.
Xu et al. "Aptamer-based microfluidic device for enrinchment, sorting, and detection of multiple cancer cells" J. Analytical Chemistry, 81 (17), 2009, pp. 7436-7442.
Yoon et al. "Nanoassembly of graphene oxide for circulating tumor cell isolation" MicroTAS 2011 Conference, Oct. 2-6, 2011, Seatle WA (www.microtas2011.org).
Yoon et al. "Sensitive capture of circulating tumour cells by functionalized graphene oxide nanosheets" Nature Nanotechnology vol. 8 (Oct. 2013), 8 pages.
Yoon et al. "Sensitive Detection of circulating tumor cells by graphene oxide nanoassembly" AIChE Annual Meeting 2011, Oct. 16-21, 2011, Minneapolis MN (www.aiche.org/Conferences/AnnualMeeting/index.aspx), 1 page.
Yu et al., "Circulating breast tumor cells exhibit dynamic changes in epithelial and mesenchymal composition", Science, vol. 339, Feb. 1, 2013, pp. 580-584.
Yu et al. "Circulating tumor cells: approaches to isolation and characterization" The Journal of Cell Biology 192, 2011, pp. 373-382.
Cogswell et al., "A Planar Labyrinth Micromixer", Proceedings of the 14th International Heat Transfer Conference IHTC14, Aug. 8-13, 2010, 5 pages.

\* cited by examiner

| A | |
|---|---|
| From | To |
| 2 | 500 |
| 4 | 498 |
| 6 | 496 |
| 8 | 494 |
| 10 | 492 |
| 12 | 490 |
| 14 | 488 |
| 16 | 486 |
| 18 | 484 |
| 20 | 482 |
| 22 | 480 |
| 24 | 478 |
| 26 | 476 |
| 28 | 474 |
| 30 | 472 |
| 32 | 470 |
| 34 | 468 |
| 36 | 466 |
| 38 | 464 |
| 40 | 462 |
| 42 | 460 |
| 44 | 458 |
| 46 | 456 |
| 48 | 454 |
| 50 | 452 |
| 52 | 450 |
| 54 | 448 |
| 56 | 446 |
| 58 | 444 |
| 60 | 442 |
| 62 | 440 |
| 64 | 438 |
| 66 | 436 |
| 68 | 434 |
| 70 | 432 |
| 72 | 430 |
| 74 | 428 |
| 76 | 426 |
| 78 | 424 |
| 80 | 422 |
| 82 | 420 |
| 84 | 418 |
| 86 | 416 |
| 88 | 414 |
| 90 | 412 |
| 92 | 410 |
| 94 | 408 |
| 96 | 406 |
| 98 | 404 |
| 100 | 402 |
| 102 | 400 |
| 104 | 398 |
| 106 | 396 |
| 108 | 394 |
| 110 | 392 |
| 112 | 390 |
| 114 | 388 |
| 116 | 386 |
| 118 | 384 |
| 120 | 382 |
| 122 | 380 |
| 124 | 378 |
| 126 | 376 |
| 128 | 374 |
| 130 | 372 |
| 132 | 370 |
| 134 | 368 |
| 136 | 366 |
| 138 | 364 |
| 140 | 362 |
| 142 | 360 |
| 144 | 358 |
| 146 | 356 |
| 148 | 354 |
| 150 | 352 |
| 152 | 350 |
| 154 | 348 |
| 156 | 346 |
| 158 | 344 |
| 160 | 342 |
| 162 | 340 |
| 164 | 338 |
| 166 | 336 |
| 168 | 334 |
| 170 | 332 |
| 172 | 330 |
| 174 | 328 |
| 176 | 326 |
| 178 | 324 |
| 180 | 322 |
| 182 | 320 |
| 184 | 318 |
| 186 | 316 |
| 188 | 314 |
| 190 | 312 |
| 192 | 310 |
| 194 | 308 |
| 196 | 306 |
| 198 | 304 |
| 200 | 102 |
| 202 | 300 |
| 204 | 298 |
| 206 | 296 |
| 208 | 294 |
| 210 | 292 |
| 212 | 290 |
| 214 | 288 |
| 216 | 286 |
| 218 | 284 |
| 220 | 282 |
| 222 | 280 |
| 224 | 278 |
| 226 | 276 |
| 228 | 274 |
| 230 | 272 |
| 232 | 270 |
| 234 | 268 |
| 236 | 266 |
| 238 | 264 |
| 240 | 262 |
| 242 | 260 |
| 244 | 258 |
| 246 | 256 |
| 248 | 254 |
| 250 | 252 |

FIG. 20A

| B | | | | | | | | | |
|---|---|---|---|---|---|---|---|---|---|
| From | To | 200 | 1805 | 405 | 1600 | 610 | 1395 | 815 | 1190 |
| 5 | 2000 | 205 | 1800 | 410 | 1595 | 615 | 1390 | 820 | 1185 |
| 10 | 1995 | 210 | 1795 | 415 | 1590 | 620 | 1385 | 825 | 1180 |
| 15 | 1990 | 215 | 1790 | 420 | 1585 | 625 | 1380 | 830 | 1175 |
| 20 | 1985 | 220 | 1785 | 425 | 1580 | 630 | 1375 | 835 | 1170 |
| 25 | 1980 | 225 | 1780 | 430 | 1575 | 635 | 1370 | 840 | 1165 |
| 30 | 1975 | 230 | 1775 | 435 | 1570 | 640 | 1365 | 845 | 1160 |
| 35 | 1970 | 235 | 1770 | 440 | 1565 | 645 | 1360 | 850 | 1155 |
| 40 | 1965 | 240 | 1765 | 445 | 1560 | 650 | 1355 | 855 | 1150 |
| 45 | 1960 | 245 | 1760 | 450 | 1555 | 655 | 1350 | 860 | 1145 |
| 50 | 1955 | 250 | 1755 | 455 | 1550 | 660 | 1345 | 865 | 1140 |
| 55 | 1950 | 255 | 1750 | 460 | 1545 | 665 | 1340 | 870 | 1135 |
| 60 | 1945 | 260 | 1745 | 465 | 1540 | 670 | 1335 | 875 | 1130 |
| 65 | 1940 | 265 | 1740 | 470 | 1535 | 675 | 1330 | 880 | 1125 |
| 70 | 1935 | 270 | 1735 | 475 | 1530 | 680 | 1325 | 885 | 1120 |
| 75 | 1930 | 275 | 1730 | 480 | 1525 | 685 | 1320 | 890 | 1115 |
| 80 | 1925 | 280 | 1725 | 485 | 1520 | 690 | 1315 | 895 | 1110 |
| 85 | 1920 | 285 | 1720 | 490 | 1515 | 695 | 1310 | 900 | 1105 |
| 90 | 1915 | 290 | 1715 | 495 | 1510 | 700 | 1305 | 905 | 1100 |
| 95 | 1910 | 295 | 1710 | 500 | 1505 | 705 | 1300 | 910 | 1095 |
| 100 | 1905 | 300 | 1705 | 505 | 1500 | 710 | 1295 | 915 | 1090 |
| 105 | 1900 | 305 | 1700 | 510 | 1495 | 715 | 1290 | 920 | 1085 |
| 110 | 1895 | 310 | 1695 | 515 | 1490 | 720 | 1285 | 925 | 1080 |
| 115 | 1890 | 315 | 1690 | 520 | 1485 | 725 | 1280 | 930 | 1075 |
| 120 | 1885 | 320 | 1685 | 525 | 1480 | 730 | 1275 | 935 | 1070 |
| 125 | 1880 | 325 | 1680 | 530 | 1475 | 735 | 1270 | 940 | 1065 |
| 130 | 1875 | 330 | 1675 | 535 | 1470 | 740 | 1265 | 945 | 1060 |
| 135 | 1870 | 335 | 1670 | 540 | 1465 | 745 | 1260 | 950 | 1055 |
| 140 | 1865 | 340 | 1665 | 545 | 1460 | 750 | 1255 | 955 | 1050 |
| 145 | 1860 | 345 | 1660 | 550 | 1455 | 755 | 1250 | 960 | 1045 |
| 150 | 1855 | 350 | 1655 | 555 | 1450 | 760 | 1245 | 965 | 1040 |
| 155 | 1850 | 355 | 1650 | 560 | 1445 | 765 | 1240 | 970 | 1035 |
| 160 | 1845 | 360 | 1645 | 565 | 1440 | 770 | 1235 | 975 | 1030 |
| 165 | 1840 | 365 | 1640 | 570 | 1435 | 775 | 1230 | 980 | 1025 |
| 170 | 1835 | 370 | 1635 | 575 | 1430 | 780 | 1225 | 985 | 1020 |
| 175 | 1830 | 375 | 1630 | 580 | 1425 | 785 | 1220 | 990 | 1015 |
| 180 | 1825 | 380 | 1625 | 585 | 1420 | 790 | 1215 | 995 | 1010 |
| 185 | 1820 | 385 | 1620 | 590 | 1415 | 795 | 1210 | 1000 | 1005 |
| 190 | 1815 | 390 | 1615 | 595 | 1410 | 800 | 1205 | | |
| 195 | 1810 | 395 | 1610 | 600 | 1405 | 805 | 1200 | | |
| | | 400 | 1605 | 605 | 1400 | 810 | 1195 | | |

FIG. 20B

| C | |
|---|---|
| From | To |
| 2 | 1000 |
| 4 | 998 |
| 6 | 996 |
| 8 | 994 |
| 10 | 992 |
| 12 | 990 |
| 14 | 988 |
| 16 | 986 |
| 18 | 984 |
| 20 | 982 |
| 22 | 980 |
| 24 | 978 |
| 26 | 976 |
| 28 | 974 |
| 30 | 972 |
| 32 | 970 |
| 34 | 968 |
| 36 | 966 |
| 38 | 964 |
| 40 | 962 |
| 42 | 960 |
| 44 | 958 |
| 46 | 956 |
| 48 | 954 |
| 50 | 952 |
| 52 | 950 |
| 54 | 948 |
| 56 | 946 |
| 58 | 944 |
| 60 | 942 |
| 62 | 940 |
| 64 | 938 |
| 66 | 936 |
| 68 | 934 |
| 70 | 932 |
| 72 | 930 |
| 74 | 928 |
| 76 | 926 |
| 78 | 924 |
| 80 | 922 |

| | |
|---|---|
| 82 | 920 |
| 84 | 918 |
| 86 | 916 |
| 88 | 914 |
| 90 | 912 |
| 92 | 910 |
| 94 | 908 |
| 96 | 906 |
| 98 | 904 |
| 100 | 902 |
| 102 | 900 |
| 104 | 898 |
| 106 | 896 |
| 108 | 894 |
| 110 | 892 |
| 112 | 890 |
| 114 | 888 |
| 116 | 886 |
| 118 | 884 |
| 120 | 882 |
| 122 | 880 |
| 124 | 878 |
| 126 | 876 |
| 128 | 874 |
| 130 | 872 |
| 132 | 870 |
| 134 | 868 |
| 136 | 866 |
| 138 | 864 |
| 140 | 862 |
| 142 | 860 |
| 144 | 858 |
| 146 | 856 |
| 148 | 854 |
| 150 | 852 |
| 152 | 850 |
| 154 | 848 |
| 156 | 846 |
| 158 | 844 |
| 160 | 842 |
| 162 | 840 |
| 164 | 838 |

| | |
|---|---|
| 166 | 836 |
| 168 | 834 |
| 170 | 832 |
| 172 | 830 |
| 174 | 828 |
| 176 | 826 |
| 178 | 824 |
| 180 | 822 |
| 182 | 820 |
| 184 | 818 |
| 186 | 816 |
| 188 | 814 |
| 190 | 812 |
| 192 | 810 |
| 194 | 808 |
| 196 | 806 |
| 198 | 804 |
| 200 | 802 |
| 202 | 800 |
| 204 | 798 |
| 206 | 796 |
| 208 | 794 |
| 210 | 792 |
| 212 | 790 |
| 214 | 788 |
| 216 | 786 |
| 218 | 784 |
| 220 | 782 |
| 222 | 780 |
| 224 | 778 |
| 226 | 776 |
| 228 | 774 |
| 230 | 772 |
| 232 | 770 |
| 234 | 768 |
| 236 | 766 |
| 238 | 764 |
| 240 | 762 |
| 242 | 760 |
| 244 | 758 |
| 246 | 756 |
| 248 | 754 |

| | |
|---|---|
| 250 | 752 |
| 252 | 750 |
| 254 | 748 |
| 256 | 746 |
| 258 | 744 |
| 260 | 742 |
| 262 | 740 |
| 264 | 738 |
| 266 | 736 |
| 268 | 734 |
| 270 | 732 |
| 272 | 730 |
| 274 | 728 |
| 276 | 726 |
| 278 | 724 |
| 280 | 722 |
| 282 | 720 |
| 284 | 718 |
| 286 | 716 |
| 288 | 714 |
| 290 | 712 |
| 292 | 710 |
| 294 | 708 |
| 296 | 706 |
| 298 | 704 |
| 300 | 702 |
| 302 | 700 |
| 304 | 698 |
| 306 | 696 |
| 308 | 694 |
| 310 | 642 |
| 312 | 690 |
| 314 | 688 |
| 316 | 686 |
| 318 | 684 |
| 320 | 682 |
| 322 | 680 |
| 324 | 678 |
| 326 | 676 |
| 328 | 674 |
| 330 | 672 |
| 332 | 670 |

| | |
|---|---|
| 334 | 668 |
| 336 | 666 |
| 338 | 664 |
| 340 | 662 |
| 342 | 660 |
| 344 | 658 |
| 346 | 656 |
| 348 | 654 |
| 350 | 652 |
| 352 | 650 |
| 354 | 648 |
| 356 | 646 |
| 358 | 644 |
| 360 | 642 |
| 362 | 640 |
| 364 | 638 |
| 366 | 636 |
| 368 | 634 |
| 370 | 632 |
| 372 | 630 |
| 374 | 628 |
| 376 | 626 |
| 378 | 624 |
| 380 | 622 |
| 382 | 620 |
| 384 | 618 |
| 386 | 616 |
| 388 | 614 |
| 390 | 612 |
| 392 | 610 |
| 394 | 608 |
| 396 | 606 |
| 398 | 604 |
| 400 | 602 |
| 402 | 600 |
| 404 | 598 |
| 406 | 596 |
| 408 | 594 |
| 410 | 592 |
| 412 | 590 |
| 414 | 588 |
| 416 | 586 |

| | |
|---|---|
| 418 | 584 |
| 420 | 582 |
| 422 | 580 |
| 424 | 578 |
| 426 | 576 |
| 428 | 574 |
| 430 | 572 |
| 432 | 570 |
| 434 | 68 |
| 436 | 566 |
| 438 | 564 |
| 440 | 562 |
| 442 | 560 |
| 444 | 558 |
| 446 | 556 |
| 448 | 554 |
| 450 | 552 |
| 452 | 550 |
| 454 | 548 |
| 456 | 546 |
| 458 | 544 |
| 460 | 542 |
| 462 | 540 |
| 464 | 538 |
| 466 | 536 |
| 468 | 534 |
| 470 | 532 |
| 472 | 530 |
| 474 | 528 |
| 476 | 526 |
| 478 | 524 |
| 480 | 522 |
| 482 | 520 |
| 484 | 518 |
| 486 | 516 |
| 488 | 514 |
| 490 | 512 |
| 492 | 510 |
| 494 | 508 |
| 496 | 506 |
| 498 | 504 |
| 500 | 502 |

FIG. 20C

| D | | | | | | | |
|---|---|---|---|---|---|---|---|
| From | To | | | | | | |
| 2 | 500 | 62 | 440 | 126 | 376 | 190 | 312 |
| 4 | 498 | 64 | 438 | 128 | 374 | 192 | 310 |
| 6 | 496 | 66 | 436 | 130 | 372 | 194 | 308 |
| 8 | 494 | 68 | 434 | 132 | 370 | 196 | 306 |
| 10 | 492 | 70 | 432 | 134 | 368 | 198 | 304 |
| 12 | 490 | 72 | 430 | 136 | 366 | 200 | 302 |
| 14 | 488 | 74 | 428 | 138 | 364 | 202 | 300 |
| 16 | 486 | 76 | 426 | 140 | 362 | 204 | 298 |
| 18 | 484 | 78 | 424 | 142 | 360 | 206 | 296 |
| 20 | 482 | 80 | 422 | 144 | 358 | 208 | 294 |
| 22 | 480 | 82 | 420 | 146 | 356 | 210 | 292 |
| 24 | 478 | 84 | 418 | 148 | 354 | 212 | 290 |
| 26 | 476 | 86 | 416 | 150 | 352 | 214 | 288 |
| 28 | 474 | 88 | 414 | 152 | 350 | 216 | 286 |
| 30 | 472 | 90 | 412 | 154 | 348 | 218 | 284 |
| 32 | 470 | 92 | 410 | 156 | 346 | 220 | 282 |
| 34 | 468 | 94 | 408 | 158 | 344 | 222 | 280 |
| 36 | 466 | 96 | 406 | 160 | 342 | 224 | 278 |
| 38 | 464 | 98 | 404 | 162 | 340 | 226 | 276 |
| 40 | 462 | 100 | 402 | 164 | 338 | 228 | 274 |
| 42 | 460 | 102 | 400 | 166 | 336 | 230 | 272 |
| 44 | 458 | 104 | 398 | 168 | 334 | 232 | 270 |
| 46 | 456 | 106 | 396 | 170 | 332 | 234 | 268 |
| 48 | 454 | 108 | 394 | 172 | 330 | 236 | 266 |
| 50 | 452 | 110 | 392 | 174 | 328 | 238 | 264 |
| 52 | 450 | 112 | 390 | 176 | 326 | 240 | 262 |
| 54 | 448 | 114 | 388 | 178 | 324 | 242 | 260 |
| 56 | 446 | 116 | 386 | 180 | 322 | 244 | 258 |
| 58 | 444 | 118 | 384 | 182 | 320 | 246 | 256 |
| 60 | 442 | 120 | 382 | 184 | 318 | 248 | 254 |
|  |  | 122 | 380 | 186 | 316 | 250 | 252 |
|  |  | 124 | 378 | 188 | 314 |  |  |

FIG. 20D

Quantification of CTCs from cancer patients and healthy donors.

| Sample number | Cancer type | Age | Gender | Cancer stage at the diagnosis | Staining | CTC/mL |
|---|---|---|---|---|---|---|
| Br1 | Breast | 65 | F | IIB | CK | 2 |
|  |  |  |  |  | CK | 1 |
|  |  |  |  |  | CK | 2 |
|  |  |  |  |  | CK | 4 |
|  |  |  |  |  | CK | 5 |
|  |  |  |  |  | CK | 1 |
| Br2 | Breast | 54 | F | IIIA | CK | 5 |
|  |  |  |  |  | HER2 | 23 |
| Br3 | Breast | 38 | F | IIB | CK | 5 |
|  |  |  |  |  | HER2 | 14 |
| Br4 | Breast | 60 | F | IIB | CK | 3 |
|  |  |  |  |  | HER2 | 12 |
| Br5 | Breast | 81 | F | IIB | CK | 2 |
|  |  |  |  |  | HER2 | 4 |
| Br6 | Breast | 61 | F | IIIB | CK | 5 |
|  |  |  |  |  | HER2 | 7 |
| Br7 | Breast | 80 | F | IIB | CK | 4 |
|  |  |  |  |  | HER2 | 11 |
| Pan1 | Pancreatic | 73 | F | IV | CK | 2 |
| Pan2 | Pancreatic | N/A | N/A | N/A | CK | 6 |
|  |  |  |  |  | Zeb-1 | 4 |
| Pan3 | Pancreatic | N/A | N/A | N/A | CK | 6 |
|  |  |  |  |  | Zeb-1 | 2 |
| Pan4 | Pancreatic | 69 | M | N/A | CK | 4 |
|  |  |  |  |  | Zeb-1 | 5 |
| Pan5 | Pancreatic | 75 | M | N/A | CK | 14 |
|  |  |  |  |  | Zeb-1 | 6 |
| Pan6 | Pancreatic | 74 | F | N/A | CK | 6 |
|  |  |  |  |  | Zeb-1 | 1 |
| Pan7 | Pancreatic | 53 | F | N/A | CK | 7 |
|  |  |  |  |  | Zeb-1 | 2 |
| Pan8 | Pancreatic | 53 | F | N/A | CK | 4 |
|  |  |  |  |  | Zeb-1 | 1 |
| Pan9 | Pancreatic | 50 | M | N/A | CK | 0 |
|  |  |  |  |  | Zeb-1 | 5 |
| L1 | Lung | 75 | M | IB | CK | 5 |
| L2 | Lung | 71 | M | IA | CK | 5 |
| L3 | Lung | 53 | M | IIA | CK | 2 |
| L4 | Lung | 79 | F | N/A | CK | 3 |
| H1 | None | 64 | F | N/A | CK | 0 |
| H2 | None | 62 | F | N/A | CK | 0 |
| H3 | None | 34 | M | N/A | CK | 0 |
| H4 | None | 20 | F | N/A | CK | 0 |
| H5 | None | 36 | F | N/A | CK | 0 |
| H6 | None | 36 | F | N/A | CK | 0 |

FIG. 32G

SYSTEM FOR DETECTING RARE CELLS

CROSS REFERENCE TO RELATED APPLICATIONS

The subject patent application claims priority to and all the advantages of U.S. Provisional Application Ser. No. 62/178,318, filed on Apr. 6, 2015, and U.S. Provisional Application Ser. No. 62/245,594, filed on Oct. 23, 2015. The contents of U.S. Provisional Application Ser. Nos. 62/178,318 and 62/245,594 are incorporated herein by reference in their entirety.

FIELD OF THE DISCLOSURE

The present disclosure relates generally to a system for detecting rare cells and a method for detecting rare cells in a fluid.

BACKGROUND

As is well appreciated in the art, there are myriad technological obstacles in the identification, enumeration, detection, capture, and isolation of rare cells. These technological obstacles tend to limit the quantitative evaluation of rare cells, for example, in early diagnosis of metastatic diseases and effective monitoring of therapeutic response in patients.

Some rare cells, e.g. circulating tumor cells (CTCs) and/or viable tumor-derived epithelial cells, have been identified in peripheral blood from cancer patients and are likely the origin of intractable metastatic disease. CTCs, as just one type of rare cell, tend to be present in an amount of about 1 CTC per 1 billion blood cells and tend to circulate in peripheral blood of patients with metastatic cancer. Detection, isolation, and capture of CTCs represent a potential alternative to invasive biopsies during diagnosis of disease. More specifically, the ability to identify, isolate, propagate and molecularly characterize CTC subpopulations could further the discovery of cancer stem cell biomarkers, expand the understanding of the biology of metastasis, and improve the therapeutic treatment of cancer patients and the ultimate treatment outcome. Many current strategies for isolating CTCs are limited to complex analytic approaches that are typically very low yield and low purity and that could be improved relative to sensitivity and accuracy.

Many technologies utilize devices through which blood flows over and around large three-dimensional structures for capturing CTCs. These structures tend to be expensive to produce, tend to act as obstacles to the flow of blood thereby decreasing the efficiency of the devices, and tend to lack sensitivity for the CTCs thereby causing the device to have a low cell capture efficiency. In addition, these devices typically face impediments to the release of captured cells, which may be due, at least in part, to the conjugation of antibodies to permanent structures within the devices.

Other technologies utilize microfeatures coated with antibodies, examples of which include the geometrically enhanced differential immunocapture chip (GEDI) chip, the chaotic micromixer HB CTC chip, the high throughput microsampling unit (HTMSU), and the HD-CTC module of an integrated system. These immunocapture devices include features fabricated from polymers, such as polydimethylsiloxane (PDMS), poly(methyl methacrylate) (PMMA), and cyclic olefin copolymer (COC). For capture of rare cells at an early cancer stage as well as during mid-metastasis, however, additional techniques and/or materials may be necessary to enhance sensitivity. Although capture of the rare cells may be accomplished, these technologies are limited with respect to post-capture analysis. This is because release of viable cells from the capture substrate is a challenge.

Accordingly, there remains an opportunity to develop an improved system for detecting rare cells and a method for detecting rare cells in a fluid.

SUMMARY OF THE DISCLOSURE

One embodiment of the present disclosure provides a system for detecting rare cells in a fluid. The system comprises a substrate and a mixture disposed on the substrate and comprising a carrier and a thermo-responsive polymer for capture and release of the rare cells.

Another embodiment of the present disclosure provides a method of detecting rare cells using a system comprising a substrate and a mixture that is disposed on the substrate and the mixture comprises a carrier and a thermo-responsive polymer. The method comprises the steps of providing the system and introducing a sample of fluid containing the rare cells into the system such that the sample interacts with the carrier for capturing the rare cells.

In yet another embodiment, the present disclosure provides a functionalized thermo-responsive polymer comprising a homo-polymer having at least one functional group for capture and release of an entity in a fluid.

In another embodiment, the present disclosure provides a thermo-responsive polymer for capturing and releasing rare cells in a fluid. The thermo-responsive polymer comprises a homo-polymer having a functional group for capturing the rare cells and a tunable lower critical solution temperature (LCST). The thermo-responsive polymer releases the captured rare cells when a temperature of the fluid is below the LCST of the thermo-responsive polymer.

In still another embodiment, the present disclosure provides a nano-composite for use in a system for detecting rare cells in a fluid. The nano-composite comprises a carrier for capturing the rare calls and selected from a functionalized nanoparticle, a functionalized graphene oxide, and combinations thereof. The nano-composite further comprises a thermo-responsive polymer for releasing the captured rare cells attached to the carrier.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Advantages of the present disclosure will be readily appreciated, as the present disclosure becomes better understood by reference to the following detailed description when considered in connection with the accompanying drawings. It is to be understood that the drawings are illustrative and may not necessarily be drawn to scale.

FIG. 20A is a table that sets forth optional non-limiting values of (A) of various embodiments of the leaf pattern set forth in FIG. 19A.

FIG. 20B is a table that sets forth optional non-limiting values of (B) of various embodiments of the leaf pattern set forth in FIG. 19A.

FIG. 20C is a table that sets forth optional non-limiting values of (C) of various embodiments of the leaf pattern set forth in FIG. 19A.

FIG. 20D is a table that sets forth optional non-limiting values of (D) of various embodiments of the leaf pattern set forth in FIG. 19A.

FIG. 32G is a table showing a quantification of CTCs from cancer patients and healthy donors.

DETAILED DESCRIPTION

Figure 1:
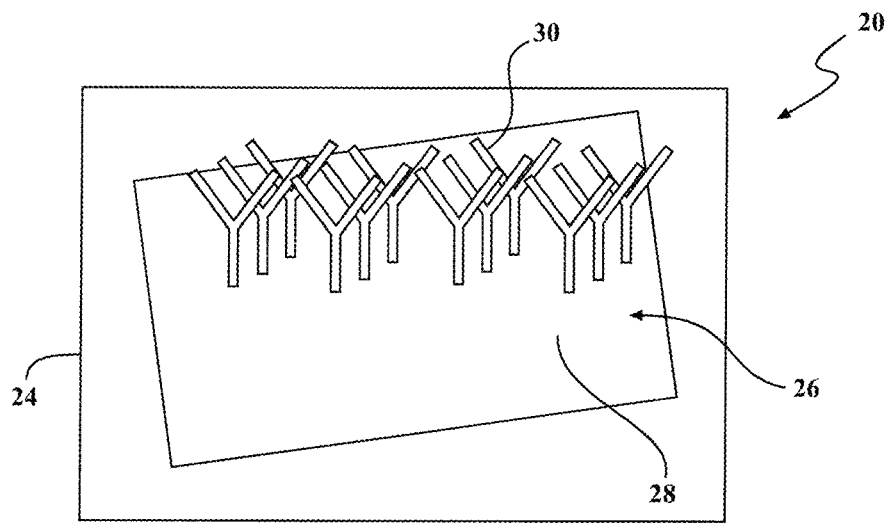
FIG. 1 is a schematic illustration of a non-limiting embodiment of a system for detecting rare cells comprising a substrate and a mixture disposed on the substrate, where the mixture includes a thermo-responsive polymer and a carrier.

The present disclosure provides a system (20), (120), (220), (320) for detecting rare cells (22). Most typically, the rare cells (22) are present in samples of blood, e.g. anticoagulated whole blood. However, it is also contemplated that the rare cells (22) may be present in samples of other bodily fluids that may be, include, consist essentially of, or consist of, but are not limited to, saliva, mucus, excretions, and the like. The terminology "consist essentially of" describes an embodiment wherein the bodily fluid is not diluted with a diluent. In one embodiment, the rare cells (22) may be transmitted via breath, i.e., breathing, sneezing, coughing, and the like, such that the rare cells (22) may be, at least for a time, airborne and thus still be present in a bodily fluid for purposes of this disclosure. The bodily fluid may be utilized without pre-dilution, pre-labeling, pre-fixation, centrifugation, lysis, or any other processing steps.

Transporting fluids, such as buffers, which may be miscible or immiscible with various samples of blood and/or bodily fluids, may also be employed. In various embodiments, samples of blood, bodily fluids, and the like, may be evaluated in volumes of about 50 µL to about 5 mL, about 100 µL to about 1 mL, or about 250 µL to about 550 µL. However, the present disclosure is not limited to these volumes or to dilution of bodily fluids. In one embodiment, about 1 mL of sample is utilized. In other embodiments, 1 to 20, 2 to 19, 3 to 18, 4 to 17, 5 to 16, 6 to 15, 7 to 14, 8 to 13, 9 to 12, or 10 to 11 mL of sample are utilized. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The particular type of rare cells (22) contemplated in this disclosure is not limited. In one embodiment, the rare cells (22) are further defined as circulating tumor cells (CTCs). In other embodiments, the rare cells (22) are chosen from the group of endothelial cells, fetal cells, and/or cells of hemopoietic origin (e.g. platelets, sickle cell red blood cells, and subpopulations of leukocytes). In still other embodiments, the terminology "rare cells" alternatively describes exosomes, microvesicles, bacteria, viruses, protists, and/or fungi.

The rare cells, such as CTCs, may be present, for example in blood, bodily fluids, and the like, in any amount, e.g. in amounts of from 0.01 to 10, from 0.1 to 10, from 1 to 10, from 1 to 20, from 1 to 30, from 1 to 40, from 1 to 50, from 1 to 60, from 1 to 70, from 1 to 80, from 1 to 90, from 1 to 100, from 100 to 1000, from 200 to 900, from 300 to 800, from 400 to 700, from 500 to 600, from 1 to 5, or 0.1, 0.2, 0.3, 0.4, 0.5, 0.6, 0.7, 0.8, 0.9, 1, 2, 3, 4, 5, 6, 7, 8, 9, or 10, rare cells per one billion total blood cells. Alternatively, the rare cells may be present in amounts of greater than 0.01, 0.1, 1, 10, 50, 100, 500, 1000, 5000, or 10000, rare cells per one billion total blood cells. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments. Rare cells present in bodily fluids other than blood and/or CTCs may also be present in the aforementioned amounts. However, the instant disclosure is not limited to these amounts of rare cells present in bodily fluids and it is contemplated that higher or lower amounts may also be utilized.

Figure 27:
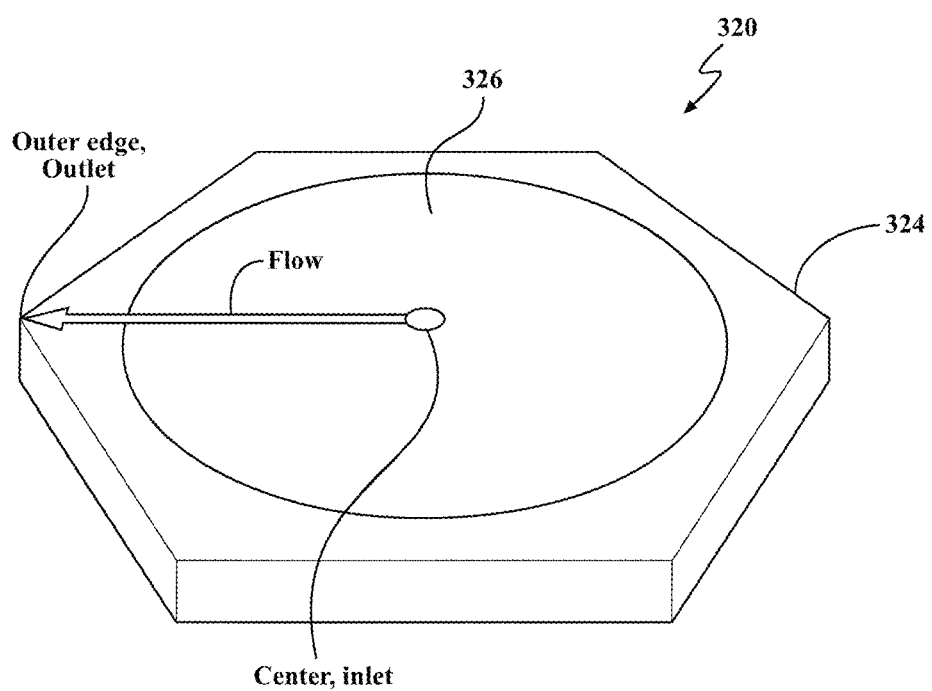
FIG. 27 schematically illustrates another embodiment of a system for detecting rare cells in a fluid, where the system includes a substrate and a mixture disposed on the substrate where fluid flows from a center of the system and radially outwards towards an outer edge of the system.

In one embodiment, the system (20) of the present disclosure includes a substrate (24) and a mixture (26) disposed on the substrate (24) and comprising a thermo-responsive polymer (28) and a carrier (30). Various embodiments of the system (20) are set forth in and described below with reference to FIGS. 1-13. In another embodiment, the system (120), (220) of the present disclosure includes a substrate (124), (224), an extension (132), (232) disposed on the substrate (124), (224) and a mixture (126), (226) disposed on the extension (132, 232) and comprising a thermo-responsive polymer (128) and a carrier (130). Various embodiments of the system (120) are set forth in and described below with reference to FIGS. 14-20. Various embodiments of the system (220) are set forth in and described below with reference to FIGS. 21-26. In still another embodiment, the system (320) of the present disclosure includes a substrate (324) and a mixture (326) comprising a thermo-responsive polymer and a carrier. Various embodiments of the system (320) are set forth in and described below with reference to FIG. 27. Typically, as bodily fluid flows over the substrate (24), (124), (224), (324) e.g. through a microfluidic channel and/or a microfluidic chamber, rare cells in the bodily fluid come into contact with the mixture (26), (126), (226), (326), etc. and become immobilized, e.g. on the surface of the substrate (24), (124), (224), (324) and/or on the surface of the extension (132, 232) by virtue of the mixture (26), (126), (226), (326). The system (20), (120), (220), (320) is described in greater detail below.

The System (20)

Figure 2:
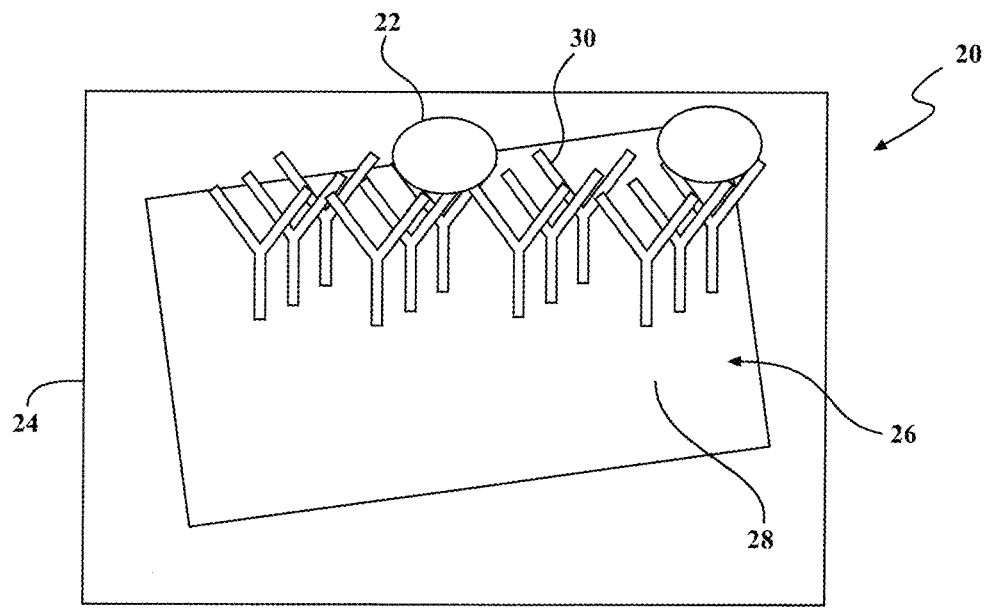
FIG. 2 is a schematic illustration of the system of FIG. 1 with rare cells captured by the carrier of the mixture.
Figure 3:
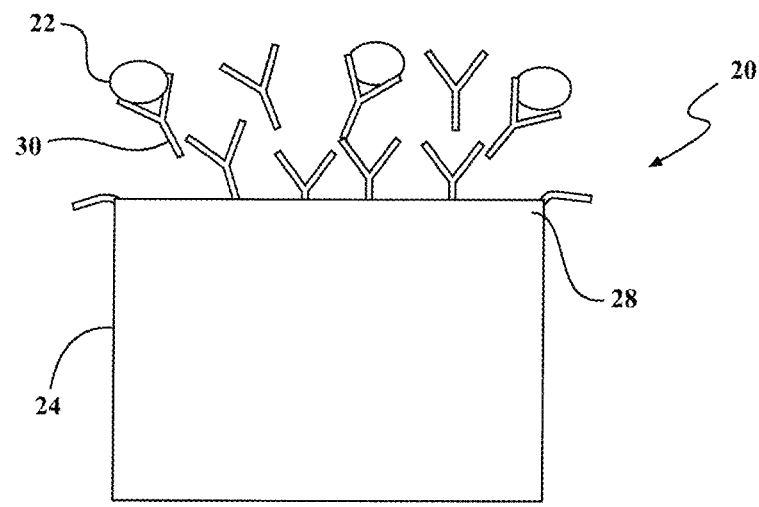
FIG. 3 is a schematic illustration of the system of FIG. 1 with the carrier and the rare cells (which are attached to the carrier) being released by the thermo-responsive polymer as the thermo-responsive polymer dissolves.

As previously described, and as shown in FIG. 1, the system (20) includes the substrate (24) and the mixture (26) disposed on the substrate (24) and comprising the thermo-responsive polymer (28) and the carrier (30). As shown in FIG. 2, rare cells (22) in a fluid that come into contact with the mixture (26) are captured and held by the carrier (30). For example, the carrier (30) typically has at least one functional group that binds to, and thereby captures the rare cells (22) when the cells (22) come into contact with functional groups of the carrier (30). As shown in FIG. 3, the rare cells (22) captured and held by the carrier (30) may be released by the thermo-responsive polymer (28). Release of the rare cells (22), which are attached to the carrier (30), occurs as the thermo-responsive polymer (28) dissolves in the surrounding fluid when a temperature of the system (20)

falls below a lower critical solution temperature (LCST) of the thermo-responsive polymer (28). Further details of the system (20) are described below.

The substrate (24) is not particularly limited in this disclosure and may be further defined as being, including, consisting essentially of, or consisting of, a metal, plastic, polymer, inorganic compound, glass, silicon (e.g. —Si—Si—), silicone (e.g. —Si—O—Si— or PDMS), epoxy, semiconductors, and/or combinations thereof. The terminology "consist essentially of" typically describes that the substrate (24) includes one or more of the particular aforementioned materials and is free of, or includes less than 0.1 or 1, weight percent, of dissimilar materials. The substrate (24) may be fabricated using any technique known in the art including, but not limited to, molding, photolithography, electroforming, machining, chemical vapor deposition, and the like.

The substrate (24) may also be further defined as a device, layer, film, coating, sheet, skin, chip, block, or wafer. In various embodiments, the substrate (24) is further defined as a tri-layered substrate that includes a silicon layer, a $SiO_2$ layer, and a PDMS (i.e., polydimethylsiloxane) layer. Alternatively, the substrate (24) may be further defined as a single layer. In one embodiment, additional layers, e.g. the $SiO_2$ layer and the PDMS layer, are disposed on the single layer and may be individually described as one or more supplemental (or support) layers. Depending on overall design and shape, one or more of the substrate (24) and/or one or more supplemental layers may be independently further defined as an outermost layer, an innermost layer, or an interior layer, e.g. of a device or of the system (20). In other embodiments, the substrate (24) and/or one or more supplemental layer may be, include, consist essentially of, or consist of, one or more of polyethylene terephthalate (PET), polyimide, polyether ether ketone (PEEK), and/or combinations thereof.

The substrate (24) and/or the one or more supplemental layers may be bonded together by any means known in the art including use of adhesives, chemical bonding techniques, and physical bonding techniques. In one embodiment, the substrate (24) includes a $SiO_2$ layer that is bonded to the substrate (24) using oxygen plasma treatment.

The substrate (24) and one or more supplemental layers are not limited to any particular configuration or structure and each of the substrate (24) and one or more supplemental layers may independently be disposed in any order or configuration relative to one another. All combinations of these layers and configurations are herein expressly contemplated. Each of the substrate (24) and supplemental layers are also not particularly limited to any particular cross-section and each may independently have, but is not limited to having, a rectangular cross-section, a square cross-section, a triangular cross-section, a circular or oval cross-section, an "I"-shaped cross-section, a "C"-shaped cross-section, an "L"-shaped cross-section, a "T"-shaped cross-section, a "U"-shaped cross-section, or a "W" shaped cross-section. The substrate (24) and supplemental layers may be solid, hollow, or have solid sections and hollow sections.

The overall size of each of the substrate (24) and supplemental layers is not particularly limited. In one embodiment, the substrate (24) has dimensions of about 35 mm×10 mm×3 mm. However, these dimensions are not limiting and may vary. Suitable non-limiting examples of substrates (24) and supplemental layers have length, width, and height dimensions on the scale of 1 to 100, 1 to 75, 1 to 50, 1 to 25, 1 to 20, 1 to 15, 1 to 10, 1 to 5, or 0.1 to 1 inches, centimeters, and/or millimeters. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments. It is also contemplated that a microfluidic device, as described in greater detail below, may have the same or different dimensions from one or more of the substrate (24) and/or the supplemental layer(s).

The mixture (26) is disposed on the substrate (24) and includes the carrier (30) and the thermo-responsive polymer (28). As shown in FIGS. 1 and 2, the mixture (26) when disposed on the substrate (24) forms a platform for the capture and release of rare cells (22) in a fluid. The mixture may be disposed on, or coupled or attached to, the substrate (24) by any means known in the art including both physical and chemical attachment including covalent bonding, electrostatic attraction, etc. In an embodiment, the mixture (26) disposed on the substrate (24) forms a film having a thickness of from about 0.5 to 10 μm, or from about 1 to 9 μm, or from about 1.5 to 8 μm, or from about 2 to 7 μm, or from about 2.5 to 6 μm, or from about 3 to 5 μm, or from about 3 to 4 μm. It is to be appreciated that a film thickness of less than 0.5 μm is undesirable, as the mixture (26) of the film cannot adequately perform capture and release of the rare cells (22) in the fluid. It is further to be appreciated that the thickness of the film is limited by the thickness of the microfluidic device. For example, the thickness of the film cannot be so thick that the combined thickness of the film and the substrate is thicker than the total thickness of the microfluidic device. With such thicknesses of the film, there would not be enough room for fluid to flow over the film and, as such, the rare cells (22) may not interact with the mixture (26) of the film. In addition, the film of the mixture (26) can be any shape, such as rectangular shape, circular shape, oval shaped, etc.

The carrier (30) is used in the mixture (26) for capturing the rare cells (22) present in a fluid. The carrier (30) is further used for protecting the rare cells (22) from polymer contamination when the thermo-responsive polymer dissolves and releases the carrier (30) with the rare cells (22). In one embodiment, the carrier (30) includes one or more types of graphene oxide and one or more markers, binding agents, etc. bonded or attached to the graphene oxide.

Figure 4:
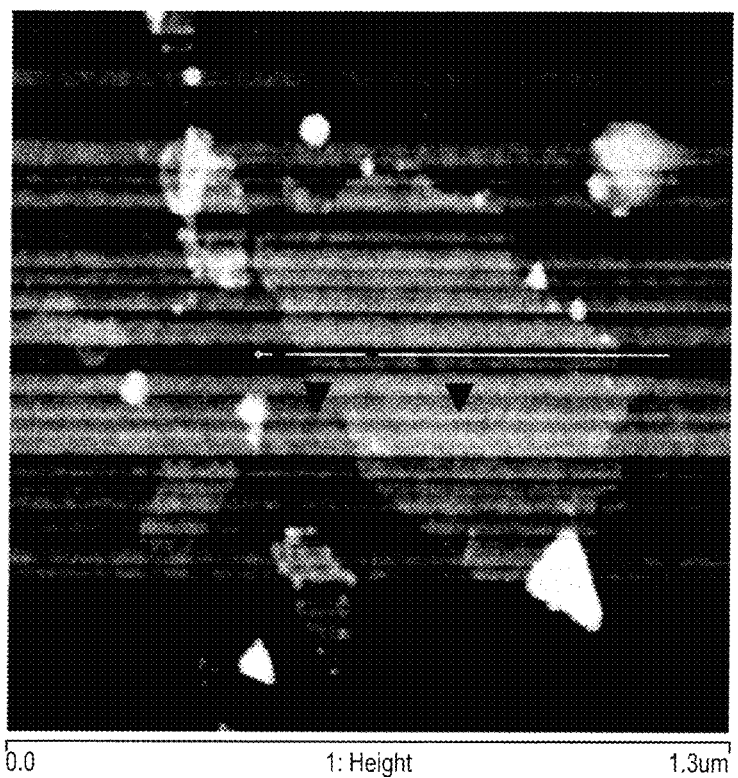
FIG. 4 is an atomic-force microscopy (AFM) image illustrating one embodiment of a graphene oxide sheet having a thickness of about 2 nm.
Figure 5:
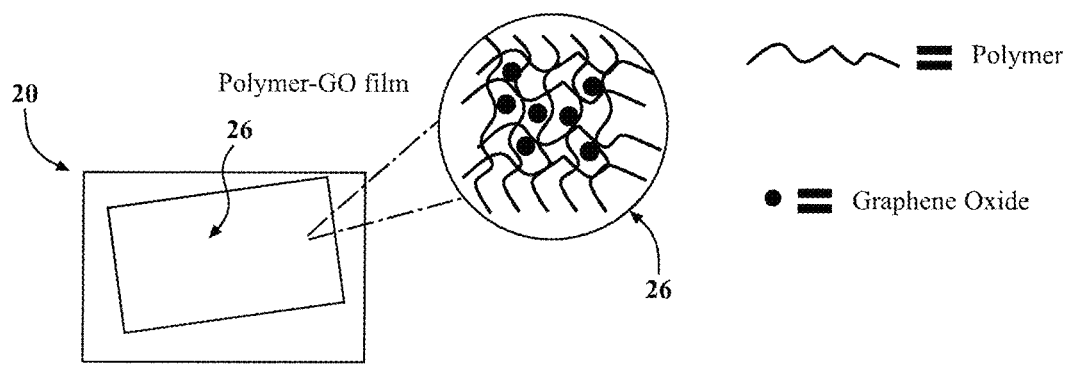
FIG. 5 is a semi-schematic illustration of one embodiment of the system comprising a substrate with a polymer-graphene oxide film disposed on the substrate, and a magnified view of the polymer-graphene oxide film.

Graphene oxide is a single layer form of graphite oxide and can be further defined as a form of graphene that includes oxygen functional groups on basal planes and edges. Typically, graphene oxide is described as a strong paper-like material. The graphene oxide may have a thickness of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 nm, or up to 50 nm, e.g. in tenth- or half-nanometer increments, each ±0.1, 0.2, 0.3, 0.4, 0.5, 0.6, 0.7, 0.8, 0.9, or 1.0, nm. FIG. 4 is an AFM image that illustrates an embodiment of a graphene oxide sheet having a thickness (i.e., a height) of about 2 nm.

In one embodiment, the graphene oxide is formed from graphite, as described in D. Li, M. B. Muller, S. Gilje, R. B. Kaner, and G. G. Wallace, "Processable aqueous dispersions of graphene nanosheets," *Nature Nanotechnology*, vol. 3, pp. 101-105, 2008, which is expressly incorporated herein by reference in a non-limiting embodiment. In another embodiment, the graphene oxide is formed using the procedure as described in Z. Wei, D. E. Barlow, and P. E. Sheehan, "The Assembly of Single-Layer Graphene Oxide and Graphene Using Molecular Templates," *Nano Letters*, Vol. 8, No. 10, pp. 3141-3145, 2008, also expressly incorporated herein by reference in a non-limiting embodiment. In still another embodiment, the graphene oxide is formed from graphene sheets that are formed using the procedure as described in H. Wang, X. Wang, X. Li, H. Dai, "Chemical Self-Assembly of Graphene Sheets," *Nano Research*, Vol. 2, pp. 336-342, 2009, also expressly incorporated herein by reference in a non-limiting embodiment. In even another embodiment, the graphene oxide is formed using the procedure described in X. Sun, Z. Liu, K. Welsher, J. T. Robinson, A. Goodwin, S. Zaric, H. Dai "Nano-Graphene Oxide for Cellular Imagine and Drug Delivery" *Nano Research*, Vol. 1, pp. 203-212, 2008, also expressly incorporated herein by reference in a non-limiting embodiment. It is also contemplated that the graphene oxide may be formed using the procedure described in U.S. Pat. App. Pub. No. US 2010/0028681, which is also expressly incorporated herein by reference in a non-limiting embodiment.

In one embodiment, graphene oxide sheets are formed by exfoliation-reintercalation-expansion methods, as described above. In another embodiment, ground natural graphite is intercalated by oleum in the presence of sodium nitrate. The product may then be treated with an aqueous solution of tetrabutylammonium (TBA) hydroxide and suspended by PL-PEG-NH$_2$ in DMF.

In an embodiment, the graphene oxide is functionalized with one or more functional groups including, but not limited to, aliphatic groups, aromatic groups, nitrogen including groups such as amines and amides, carboxyl groups, sulfur including groups, phosphorous including groups, and the like. Alternatively, the graphene oxide can be functionalized with one or more markers, antibodies (such as EpCAM, CD133, CD44, EGFR, and combinations thereof), antigens, proteins, tumor specific binding agents (e.g. anti-EpCAM), and the like. In another embodiment, the terminology "tumor specific binding agent" describes an agent that binds to a nonhemopoietic cell that can form a tumor, such as a cell not of hemopoietic origin, excluding blood cells and immune cells, but including epithelial cells, endothelial cells, neurons, hepatocytes, nephrons, glial cells, muscle cells, skin cells, adipocytes, fibroblasts, chondrocytes, osteocytes, and osteoblasts. The binding agent may bind to a cell surface marker that is specific for a type of cell that can form a tumor and that is not normally found in circulating blood. In an alternative, the binding agent may bind to a cell surface marker that is specific for a transformed cell. Such agents may also bind to healthy cells circulating in blood from non-pathogenic origins, e.g., venipuncture or trauma. In other embodiments, Streptavidin and/or one or more antibodies for various viruses may be utilized.

In various embodiments, the graphene oxide is functionalized with one or more markers that allows for identification, enumeration, detection, capture, and/or isolation of genomic DNA, cDNA, or mRNA sequences, proteins or other intracellular contents that are indicative of a type or presence of a particular tumor, determination of the presence or absence of certain mutations in EGFR, HER2, prostate specific antigen TMPRSS2-ERG, CD133, CD44, CD24, epithelial-specific antigen (ESA), Nanog, 25 BMI1, and the like. Alternatively, the graphene oxide may be functionalized with one markers that allows for identification, enumeration, detection, capture, and/or isolation of cells related, but not limited, to one or more of the following cancers: ostate, lung, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, non-small cell lung cancer (NSCLC), soft tissue sarcoma, squamous cell carcinoma, stomach cancer, thyroid cancer, topical skin lesion, veticulum cell sarcoma, Wilm's tumor, and/or combinations thereof.

In one embodiment, the graphene oxide is functionalized with polyethylene glycol. For example, expandable graphite may be exfoliated and heated at about 900 C for about 1 hour under argon to remove intercalated acid molecules. Then, a salt such as NaCl may be added and removed by filtration with water to reduce particle size. Then, a strong acid, such as sulfuric acid, may be added to effect intercalation. Further, an oxidizing agent such as KMnO4 may be added and the product may be washed. Subsequently, carboxylic acid functional groups made be added along with NaOH followed by sonication, neutralization, filtering and washing. The product formed is then typically a carboxylic acid modified graphite oxide (GO—COOH). This product may be then sonicated with a 6-arm polyethylene glycol-amine and N-(3-dimethylaminopropyl-N'-ethylcarbodiimide) hydrochloride may be added. Finally, mercaptoethanol may be added and the product subjected to centrifugation in PBS to form NGO-PEG.

Figure 7:
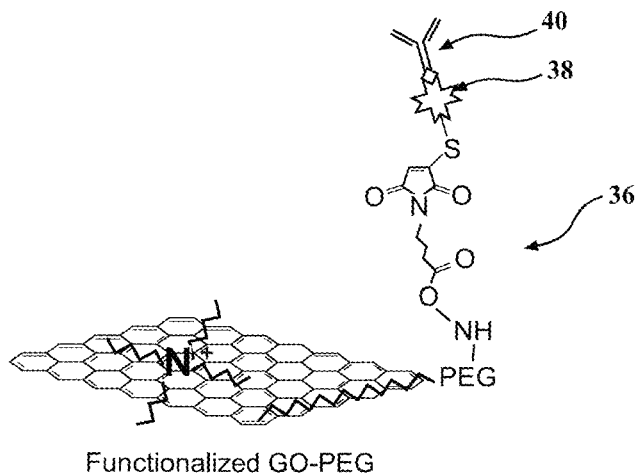
FIG. 7 is an illustration of a functionalized polymer-graphene oxide (GO-PEG).

In still other embodiments, the graphene oxide is functionalized with a linking molecule or linker (36), such as shown in FIG. 7. In one example, the linker (36) may be GMBS which is known as N-[g-maleimidobutyryloxy]succinimide ester in the art. In another example, the linker (36) may be sulfo-GMBS, which is a water soluble derivative of GMBS. The linking molecule (36) is not particularly limited. It is also contemplated that the graphene oxide (i.e., the carrier (30)) and/or the linking molecule (36) may be functionalized or bonded to a marker (38), as also shown in FIG. 7. An example of a marker (38) may be a protein, such as NeutrAvidin. The protein may be directly bonded to the graphene oxide and/or the linking molecule (36). It is further contemplated that the graphene oxide, the linking molecule (36), and/or the marker (38) may be functionalized or bonded to an antibody (40), as also shown in FIG. 7. An example of an antibody (40) may be EpCAM against the EpCAM antigen expressed on the surface of cancer cells. The antibody (40) may be directly bonded to the graphene oxide, the linking molecule (36), and/or the marker (38). In one embodiment, the graphene oxide is functionalized with (i.e., bonded to) a linking molecule which, in turn, is functionalized with (i.e., bonded to) a protein which, also in turn, is functionalized with (i.e., bonded to) an antibody. The antibody can then bind a rare cell (22) such as a CTC. The instant disclosure is not limited to the aforementioned antibodies, proteins, etc. and one or more known in the art may be utilized and bonded to the graphene oxide. Suitable non-limiting examples include various antibodies and/or proteins, epithelial surface markers such as EGFR, prostate markers such as PSMA, PSA, cancer cell markers such as CD133, CD44, ALDH, endothelial markers such as CD31, CD34, leukocyte markers such as CD45, CD4, exosome/ microvessicle markers such as CD63, etc. Alternatively, various peptides recognizing particular DNA sequences may be utilized.

In one embodiment, the graphene oxide is functionalized with a binding agent, the binding agent includes the reaction product of phospholipid-polyethylene-glyco-amine (PL-PEG-NH$_2$) and N-g-maleimidobutyryloxy succinimide ester (GMBS), the reaction product is further bonded to a protein, and the protein is further bonded to an antibody for interaction with the rare cells.

It is to be appreciated that the carrier (30) is not limited to functionalized graphene oxide, and can otherwise include any suitable nanoparticle with one or more surface groups bonded or attached to the nanoparticle. Suitable surface groups include any of the functional groups described above for the graphene oxide. In addition, and as will be described in further detail below, the thermo-responsive polymer (28) has a polymer matrix, and the carrier (30) is embedded in the polymer matrix of the thermo-responsive polymer (28) (as shown, for example, in FIGS. 5 and 8). Accordingly, the functionalized nanoparticle may be selected from any nanoparticle with functional surface group(s) that can suitably be embedded in the polymer matrix of the thermo-responsive polymer (28). One example of a suitable nanoparticle for the carrier (30) is a silicon nanoparticle with one or more markers, binding agents, etc. bonded or attached to the surface of the silicon nanoparticle.

Figure 6:
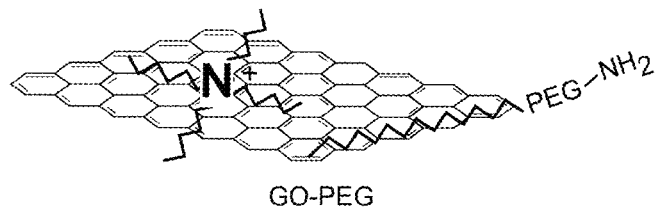
FIG. 6 is an illustration of nonfunctionalized polymer-graphene oxide (GO-PEG), where the graphene oxide acts as a carrier for PEG-NH$_2$.
Figure 8:
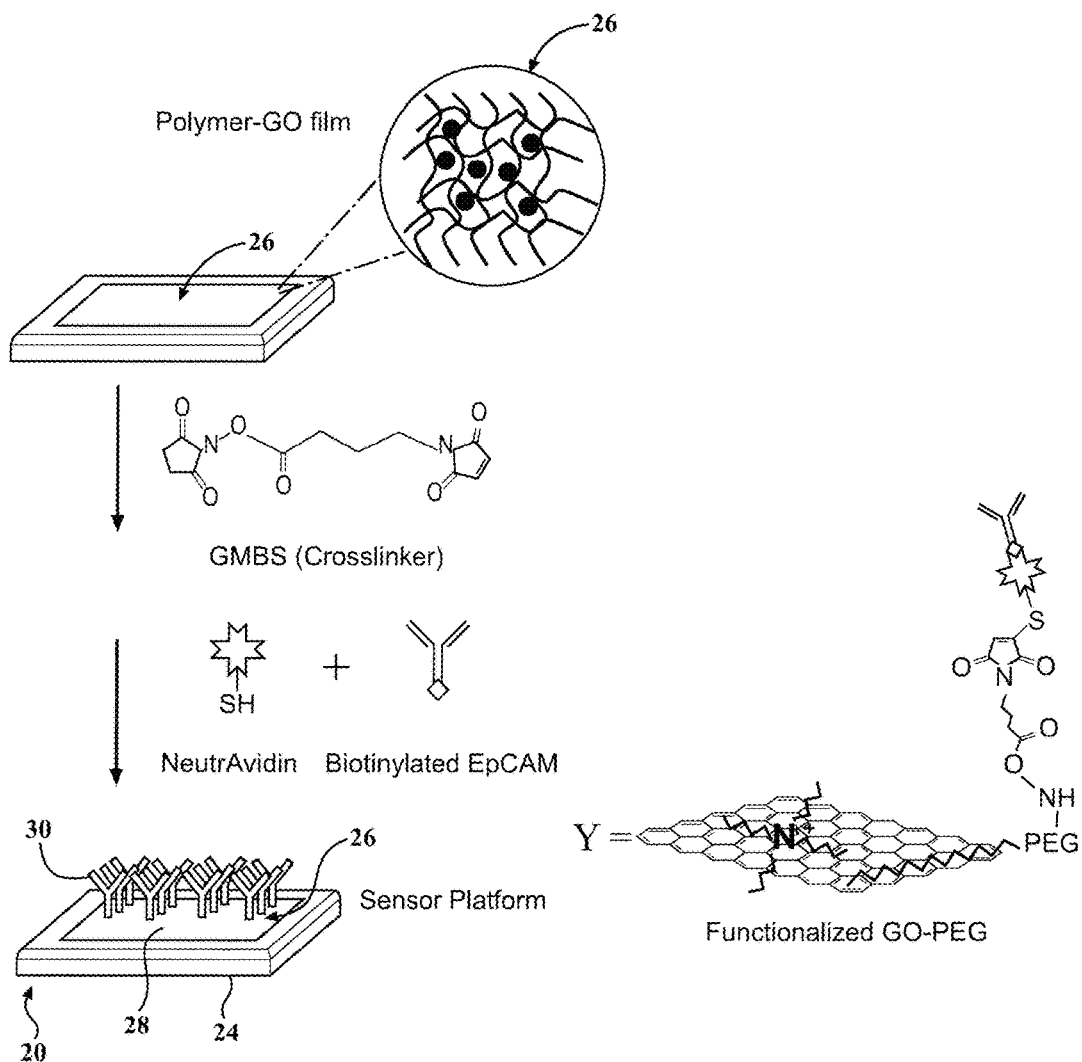
FIG. 8 is an illustration of a process for embedding graphene oxide in a thermo-responsive polymer, and introducing a linker (e.g. GMBS), a marker (e.g. NeutrAvidin), and an antibody (e.g. biotinylated EpCAM) to the graphene oxide.

In an embodiment, and with reference to FIG. 8, the mixture (26) may be formed by mixing the thermo-responsive polymer (28) with the carrier (30). For example, the thermo-responsive polymer (28) is dissolved in a suitable solvent and the carrier (30) (such as graphene oxide in solution) is added to the thermo-responsive polymer (28) solution. The thermo-responsive polymer (28) solution and the graphene oxide in solution are mixed in a common solvent. Typically, from 25 to 100 μL of the graphene oxide solution is added per 10 mg of the thermo-responsive polymer. It is to be understood that the mixture (26) requires a critical amount of carrier (30). In instances where the amount of carrier (30) is too high (such as greater than 100 microliters per 10 mg of thermo-responsive polymer), the resultant film may have cracks or other undesirable blemishes. In embodiment, the mixture (26) is applied to the substrate (24), such as by drop casting, and allowed to dry. The dried mixture (26) forms a nano-composite film on the substrate (24) surface, where the film includes the thermo-responsive polymer (28) having a polymer matrix and the carrier (30) embedded in the polymer matrix. For example, functionalized graphene oxide may be mixed in the thermo-responsive polymer (28), and after dry casting, a polymer-graphene oxide (or polymer-GO) film forms with the functionalized graphene oxide embedded in the polymer (28), as shown at least in FIG. 5. An illustration of the graphene oxide (GO) for the polymer-GO film is shown in FIG. 6.

Thermo-responsive polymers are a class of stimuli-responsive polymers that respond to temperature changes by undergoing conformational changes. Thermo-responsive polymers have been used for various applications, such as for drug delivery, tissue engineering, controlling cell adhesion and bacterial growth, and protein encapsulation. In the present disclosure, the thermo-responsive polymer (28) is used for releasing rare cells (22) captured by the carrier (30), e.g. functionalized graphene oxide. The thermo-responsive polymer typically provides temperature dependent dissolution in the fluid that, once dissolved, releases the carrier (30) with the rare cell (22) still attached to the carrier (30). In an embodiment, the thermo-responsive polymer (28) has a tunable lower critical solution temperature (LCST) for allowing release of the captured rare cells (i.e., the rare cells attached to the carrier) when a temperature of the system (20) is below the LCST of the thermo-responsive polymer (28). It is believed that the biocompatible functionalized nanomaterial (e.g. the functionalized graphene oxide) with the thermo-responsive polymer that promotes effective cell release improves capture sensitivity while substantially simultaneously allowing viable cell release. This may lead to improved downstream analysis, such as fluorescence in situ hybridization (FISH), molecular analysis, and single cell analysis.

In various embodiments, the thermo-responsive polymer (28) may be a homo-polymer having a tunable LCST that enables use of the system (20) at room temperature (e.g. at a temperature of from about 22 to 26° C.). Accordingly, the thermo-responsive polymer (28) utilized in the mixture (26) should be selected from a homo-polymer having a LCST that is below room temperature. With use of the system (20) at room temperature, the capture and release of the rare cells (22) can be accomplished without having to expose the system (20) to harsh environmental conditions, which could be damaging to the cells (22) and/or the individual components/materials of the system (20). In an embodiment, the thermo-responsive polymer is a homo-polymer having a tunable LCST, and the LCST of the thermo-responsive polymer (28) used in the mixture (26) is from about 7 to 18° C., or from about 9 to 17° C., or from about 11 to 16° C., or from about 13 to 15° C. In one embodiment, the thermo-responsive polymer has an LCST of from about 13 to 18° C., and more particularly an LCST of about 15° C. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The thermo-responsive polymer (28) typically exhibits a different solubility in response to variations in temperature. The presence of the LCST (i.e., the critical temperature below which the polymer-solvent system is miscible in all proportions and above which phase separation occurs) is unique and is typically entropically driven. At the LCST, the thermo-responsive polymer (28) begins phase separation, where the polymer (28) begins to separate from the fluid. This is due, at least in part, to a molecular transition from a coiled enthalpically-favored polymer structure to a globular entropically-favored polymer structure. The LCST is often observed in highly polar solvents, such as water and ethanol, driven by hydrogen bonding interactions between the solvent and the polymer chains.

In an embodiment, the thermo-responsive polymer (28) for the mixture (26) may be selected from a suitable polymer having a LCST temperature of from about 7° C. to 18° C. In this embodiment, the selected thermo-responsive polymer is used directly in the mixture (26). In another embodiment, the thermo-responsive polymer (28) may have a LCST temperature that is higher or lower than the foregoing range. However, where the LCST of the polymer is tunable, the polymer (28) may be modified to obtain a polymer with a LCST falling within the foregoing range. Accordingly, in this embodiment, the thermo-responsive behavior (or LCST) of the polymer (28) may be tuned or modulated through modification of the chemical structure of the monomeric units of the thermo-responsive polymer (28) to make such monomeric units more hydrophic or hydrophilic. Accordingly, the thermo-responsive polymer (28) utilized in the mixture (26) is a homo-polymer with a modified chemical structure so that the LCST temperature falls within the range of about 7° C. to 18° C. In yet another embodiment, in instances where the thermo-responsive polymer (28) has a LCST temperature that is higher or lower than the foregoing range, the thermo-responsive behavior of the polymer (28) may be modulated through co-polymerization of two or more monomers with different hydrophobicity or hydrophilicity. Typically, the more hydrophobic the polymer is, the lower the critical temperature will be. In addition, the LCST of the thermo-responsive polymer (28) may also be dependent on the molecular weight of the polymer, tacticity, chain-end groups, concentration of the polymer solution, and salt type and concentration in the solution.

Various classes of homo-polymers that show thermo-responsive behavior and may be used as the thermo-responsive polymer (28), or may be chemically modified to achieve a desirable thermo-responsive behavior, are set forth below:

1. Poly(N-alkyl acrylamides) (Left to Right, Name and LCST)

Poly(N-isopropylacrylamide) (PNIPAM): 33° C.
Poly(N-n-propylacrylamide) (PNNPAM): 10° C.
Poly(N-cyclopropylacrylamide) (PNCPAM): 53° C.
Poly(N,N-diethylacrylamide) (PDEAM): 33° C.

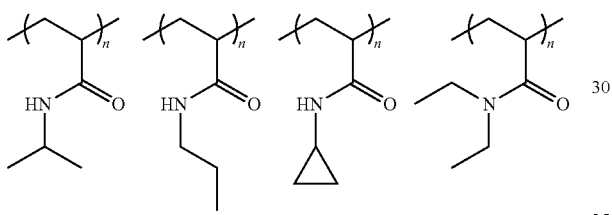

Another polymer of the same class as poly(N-alkyl acrylamides) with a suitable LSCT is poly(N—(N'-isobutylcarbamido)propyl methylacrylamide) (PiBuCPMA): 13° C.:

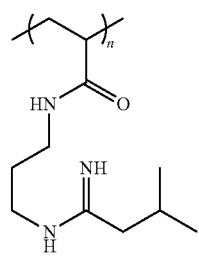

2. Poly(N-vinylalkylamide) (Left to Right, Name and LCST)

Poly(N-vinylisobutyramide) (PNVIBA): 39° C.
Poly(N-vinyl-n-butyramide) (PNVBA): 32° C.

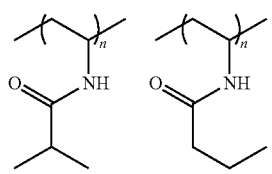

3. Lactam/Pyrrolidone/Pyrrolidone Based Polymers (Left to Right, Name and LCST)

Poly(N-vinylcaprolactam) (PVCL): 32° C.
Poly(N-vinylpyrrolidone) (PVP): 30° C.
Poly(N-ethylpyrrolidine methacrylate) (PNEPMA): 15° C.
Poly(N-acryloylpyrrolidine) (PNAP): 51° C.

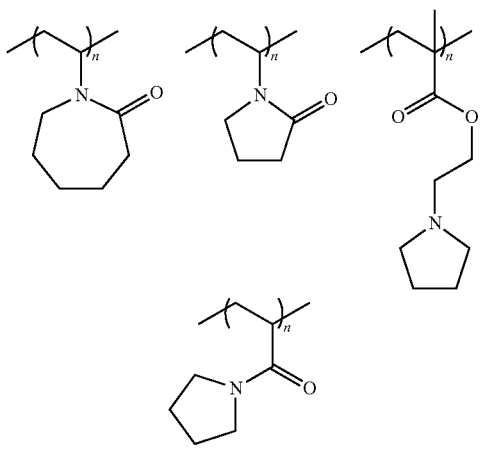

4. Poly(vinyl ether)s (Left to Right, Name and LCST)

Poly(methyl vinyl ether): 35-36° C.
Poly(2-(2-ethoxy)ethoxyethyl vinyl ether) (PEOEOVE): 41° C.
Poly(2-methoxyethyl vinyl ether) (PMEVE): 70° C.

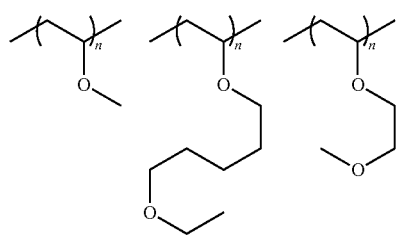

5. Poly(oxazoline)s (Left to Right, Name and LCST)

Poly(2-ethyl 2-oxazoline) (PEOx): 62-65° C.
Poly(2-isopropyl 2-oxazoline) (PiPOx): 36° C.
Poly(2-n-propyl 2-oxazoline) (PnPOx): 36° C.

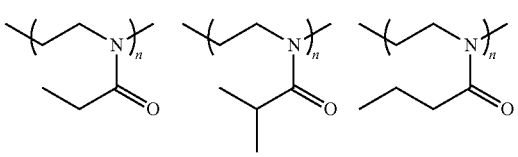

6. Poly(N-acryloyl piperidine)

Poly(N-acryloyl piperidine: LCST=5° C.

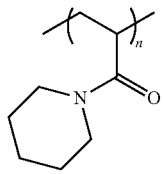

7. Poly(phosphazenes)

Poly[bis((ethoxyethoxy)ethocy)phosphazene] (PBEEP), LCST=38° C.

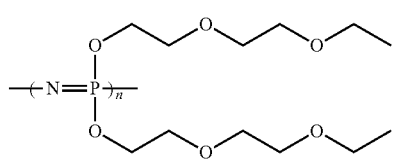

Poly[bis(2,3-bis(2-methoxyethoxy)propanoxy) phosphazene] (PBBMEP), LCST=38° C.

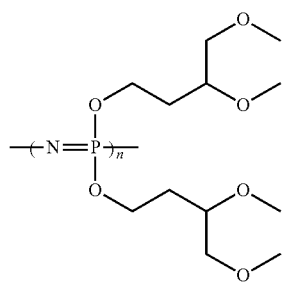

8. Poly(N-acryloyl-1-proline methyl ester)

Poly(N-acryloyl-1-proline methyl ester) poly(A-Pro-OMe), LCST=15-20° C.

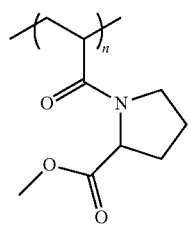

9. Poly(N-acryloyl-L-valine N'-methylamide)

Poly(N-acryloyl-L-valine N'-methylamide) (PAVMA), LCST=5.6-19.1° C.

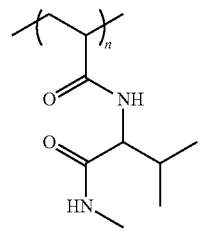

10. Poly(2-hydroxypropylacrylate)

Poly(2-hydroxypropylacrylate) (PHPA), LCST=30-60° C.

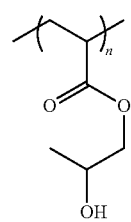

It is to be understood that "n" in each of the chemical formulas provided above can be from 20 to 1000. In addition, and in an embodiment, the thermo-responsive polymer (28) may also be a combination of two or more homo-polymers identified above.

Copolymerization is another way of controlling the thermo-responsive behavior (e.g. LCST) of the thermo-responsive polymer (28). For example, if the critical temperature of the polymer (28) needs to be decreased, then the polymer (28) may be copolymerized with a more hydrophobic monomer. Similarly, if the critical temperature of the polymer (28) needs to be increased, then the polymer (28) may be copolymerized with a more hydrophilic monomer. The critical temperature can be tuned or modulated by changing the ratio of the two monomers in the copolymer. It is to be appreciated, however, that since the thermo-responsive behavior is an interplay of hydrogen bonding and hydrophobic interactions between the polymer chain and molecules of the solvent, the resultant copolymer may not be soluble due to stronger hydrogen bonding interactions between the constituent monomers. Examples of copolymers exhibiting LCST behavior and which may be used as the thermo-responsive polymer are set forth below:

1. Copolymer of N-isopropylmethylacrylamide and a methylacrylamide Monomer with Labile Hydrazone Linkage (LCST: 13-44° C.)

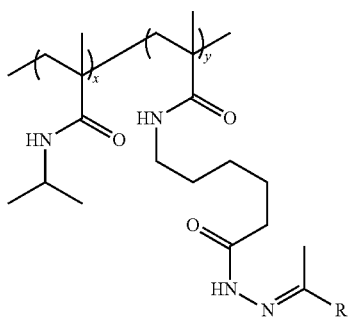

R = $CH_3$, n-$C_4H_9$, n-$C10H_{21}$

2. Poly[(di(ethylene glycol) ethyl ether acrylate)-co-(oligoethylene glycol acrylate)] (LCST: 15-90° C.)

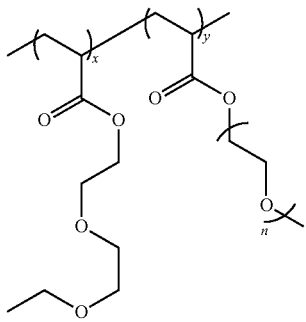

3. Poly(N-acrloyl piperidione-co-N,N-diethylacrylamide

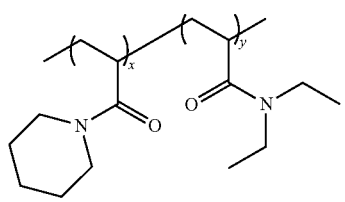

4. Poly(vinyl alcohol-co-vinyl acetal) (P(VOH-co-VAc), LCST=17-41° C.

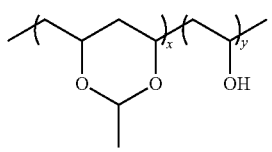

5. Poly(glycidol-co-glycidol acetate), LCST=4-100° C.

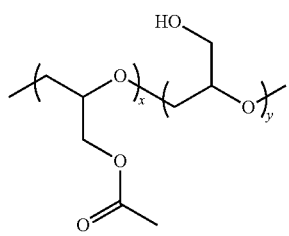

It is to be understood that "x" in the chemical formulas above can be from 20 to 1000, "y" in the chemical formulas above can be from 20 to 1000, and "n" in the chemical formulas above can be from 20 to 1000. In addition, and in an embodiment, the thermo-responsive polymer may also be a combination of two or more of the copolymers identified above.

In various embodiments, polymers suited for the mixture (26) has a LCST that is below room temperature to allow easy device handling for cell capturing at room temperature and release at temperature below room temperature. There are many homo-polymers and copolymers that have an LCST below room temperature (effectively below 20° C.); however, the polymers that can be used in the mixture (26) depends on the solubility and stability of the polymer in the solvent, such as (N,N-dimethylformamide) (DMF), as well as on the film quality after drop casting. Examples of more preferred thermo-responsive polymers include: poly(N-n-propylacrylamide) (LCST=10° C.); poly(N—(N'-isobutyl-carbamido)propyl methylacrylamide) (LCST=13° C.); poly (N-(2,2-di-methyl-1,3-dioxan-5-yl)methacrylamide) (LCST=15.3° C.); poly(N-(2,2-di-methyl-1,3-dioxan-5-yl) acrylamide) (LCST=17.8° C.); poly(N-ethylpyrrolidine methacrylate) (LCST=15° C.); poly(2-n-propyl-2-oxazine) (LCST=11-13° C., n=15-50); poly(N-acryloyl-L-valine N'-methylamide) (LCST=5.6-19.1° C.); and poly(N-acryloyl-1-proline methyl ester) (LCST=15-20° C.).

Figure 9:
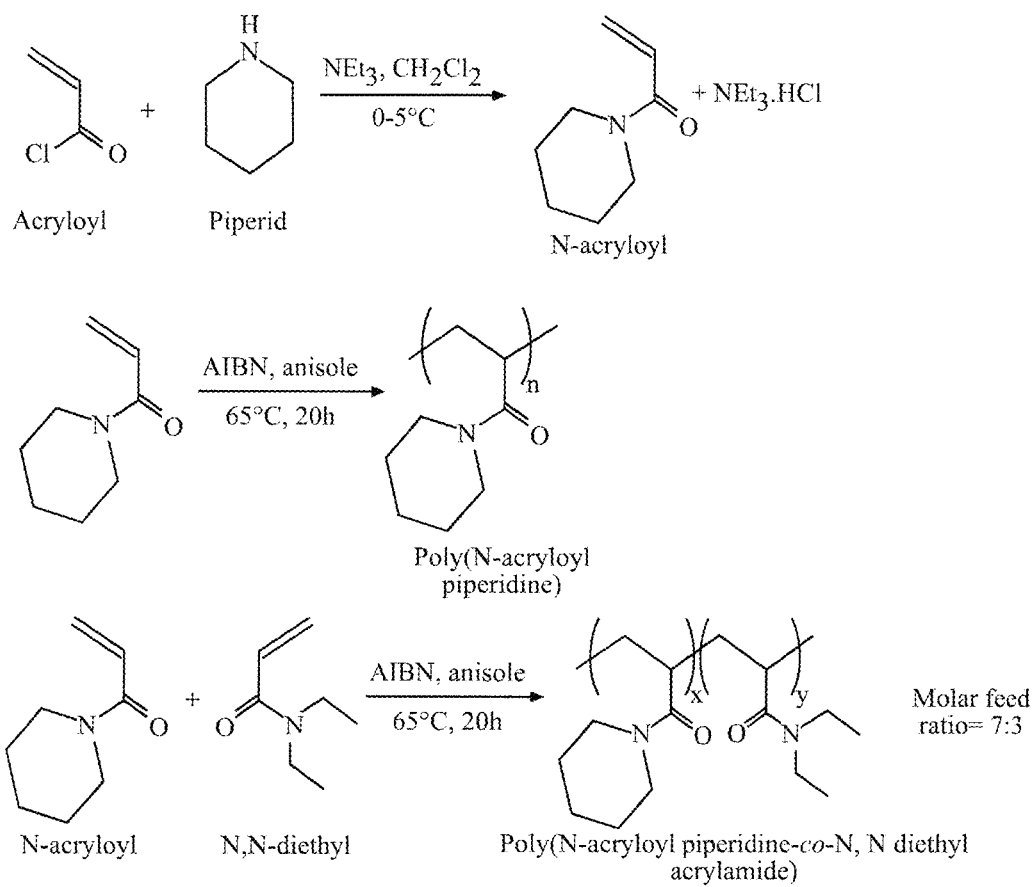
FIG. 9 illustrates one embodiment of a process for tuning a lower critical solution temperature (LCST) of poly(N-acryloyl piperidine) by copolymerization.

An illustration of a process for tuning the LCST of the thermo-responsive polymer (28) by copolymerization is described with reference to FIG. 9. In this example, poly (N-acryloyl piperidine) is formed according to the following process. As shown, acryloyl chloride reacts with piperidine in the presence of $NEt_3$ and $CH_2Cl_2$ at a temperature of from about 0 to 5° C. to form N-acryloyl piperidine and $NEt_3.HCl$. N-acryloyl piperidine is polymerized in the presence of AIBN and anisole at a temperature of about 65° C. for about 20 hours to form poly(N-acryloyl piperidine) having a LCST of about 5° C. Modulation of the LCST of poly(N-acryloyl piperidine) to increase the LCST may be accomplished through copolymerization. In an example, and as also shown in FIG. 9, N-acryloyl piperidine may be copolymerized with N,N-diethyl acrylamide in the presence of AIBN and anisole at a temperature of about 65° C. for about 20 hours to form poly(N-acryloyl piperidine-co-N,N-diethyl acrylamide) having a LCST of about 13° C.

Figure 10:
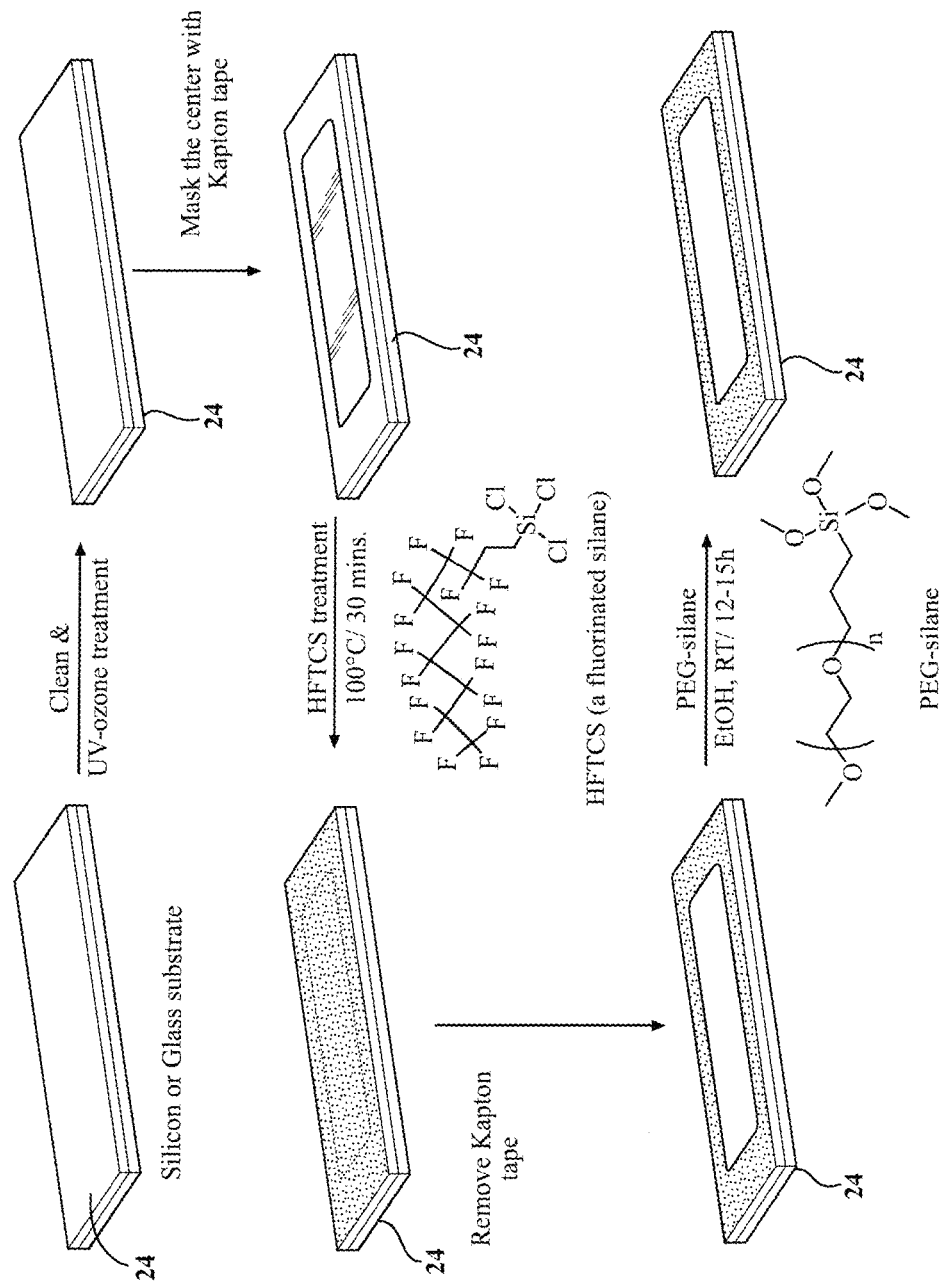
FIGS. 10 and 11 illustrate one embodiment of a process for fabricating the system as a microfluidic device including a substrate and a polymer-graphene oxide film disposed on the substrate, where the microfluidic device further defines a microfluidic chamber and/or channel.
Figure 11:
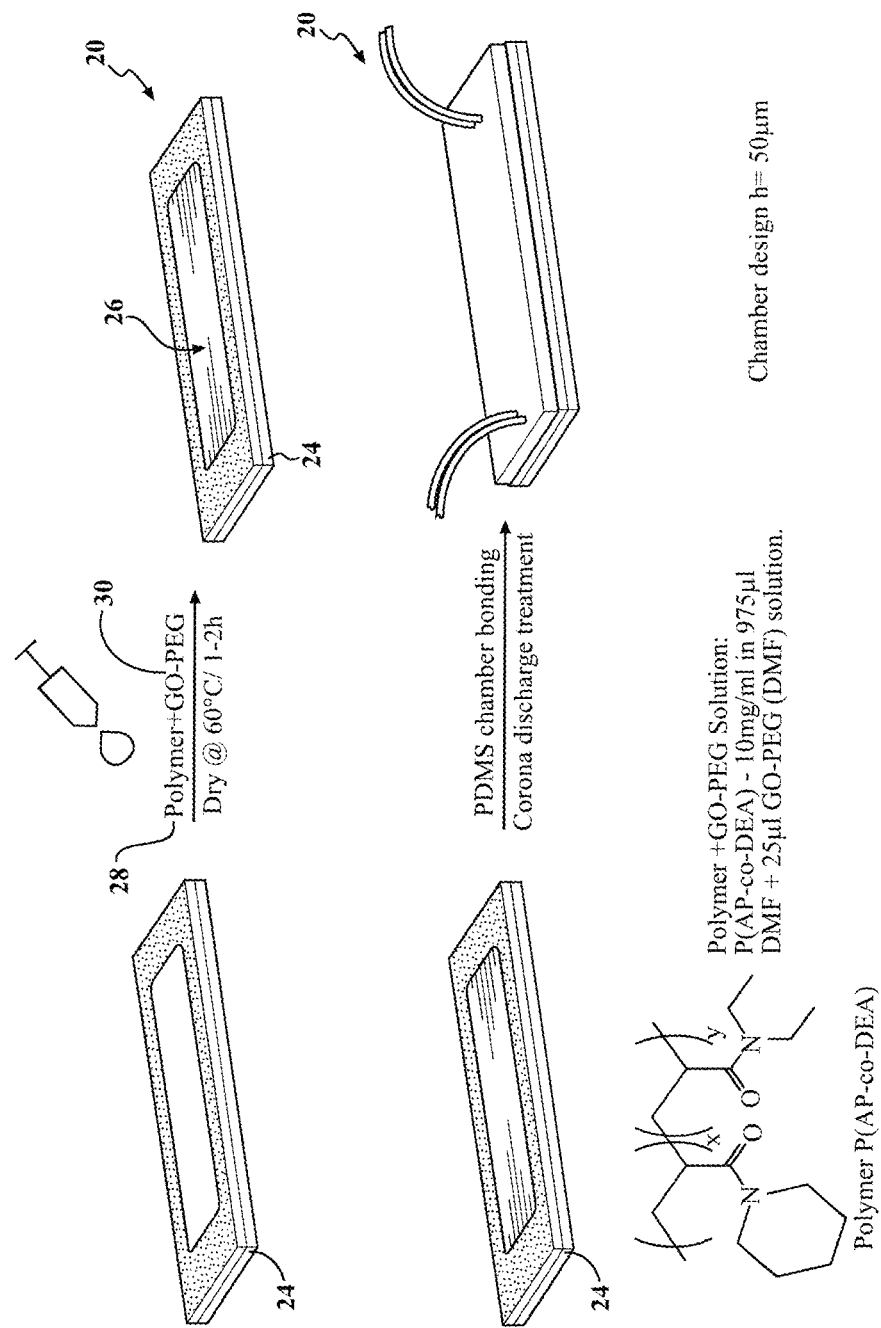
Figure 12:
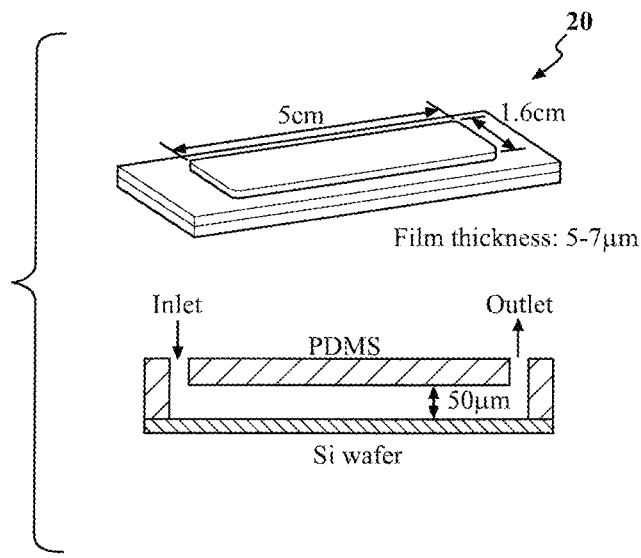
FIG. 12 is another illustration of an embodiment of the system including the substrate and the mixture disposed on the substrate, and showing example dimensions of the system.
Figure 13A:
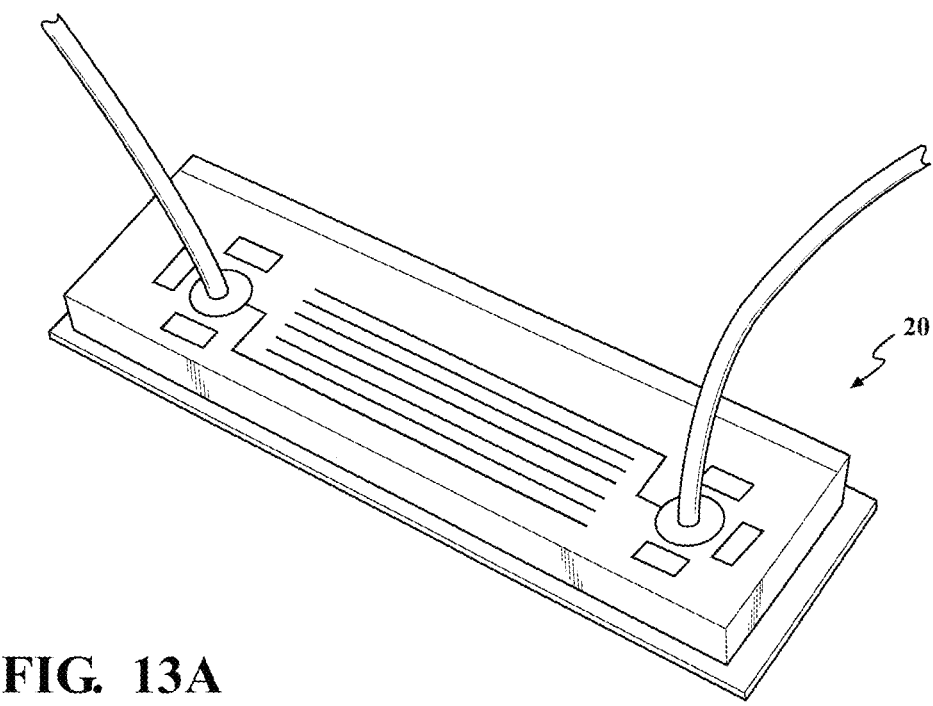
FIG. 13A illustrates an embodiment of a microfluidic device.
Figure 13B:
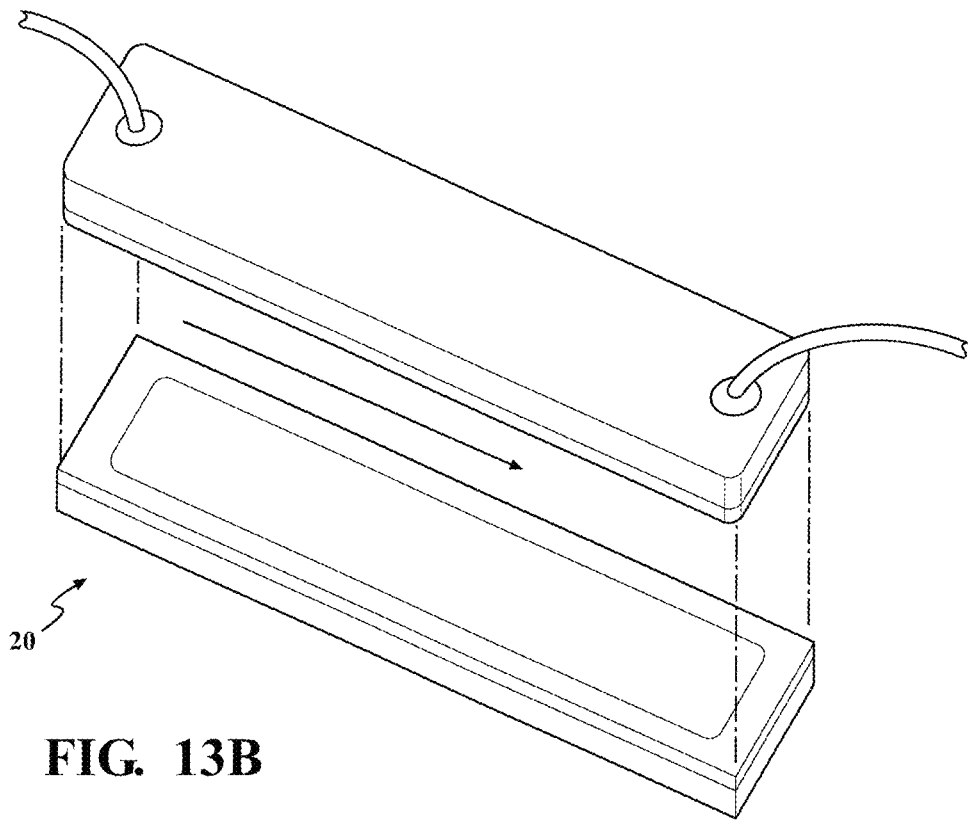
FIG. 13B illustrates another embodiment of the microfluidic device.
Figure 13C:
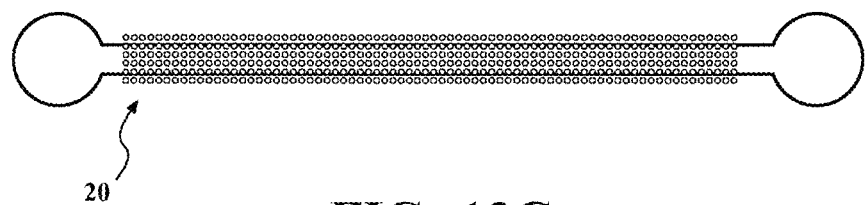
FIG. 13C illustrates another embodiment of the microfluidic device.
Figure 13D:
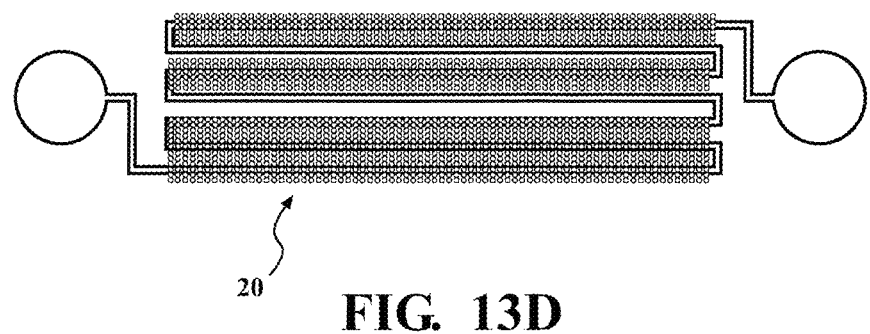
FIG. 13D illustrates another embodiment of the microfluidic device.

In an embodiment, the system (20) is further defined as a microfluidic device. The microfluidic device (and/or system (20)) may include a microfluidic channel and/or a microfluidic chamber through which blood, bodily fluids, and/or other substances can flow. The microfluidic device (and/or system (20)) may be fabricated as follows. With reference to FIG. 10, the microfluidic device (and/or system (20)) may be fabricated by providing the substrate (24) and cleaning the surface of the substrate (24). In an embodiment, the substrate (24) surface may also be UV-ozone treated in addition to being cleaned. The method further includes masking the surface of the substrate (24) with tape, such as Kapton tape and applying HFTCS (which is a fluorinated silane) treatment to the masked substrate (24) at about 100° C. for about 30 minutes. The method further includes removing the Kapton tape, and treating the substrate (24) with PEG-silane in EtOH at room temperature for about 12 to 15 hours to form a PEG-silane treated substrate (24). As shown in FIG. 11, the method further includes forming a polymer-GO film on the surface of the treated substrate (24). This may be accomplished by applying (such as by drop casting) a mixture (26) of the thermo-responsive polymer (28) and the carrier (30) (e.g. graphene oxide) to the surface of the treated substrate (24) and drying the mixture (26) at a temperature of about 60° C. for about 1 to 2 hours to form the system (20). Microfluidic chamber(s) and/or channel(s) may then be formed utilizing a corona discharge treatment. As shown in FIG. 12, the resultant system (20) includes a substrate (24) (e.g. a Si wafer with PDMS formed on the Si wafer) and a chamber defined within the substrate (e.g. between the Si wafer and the PDMS). The height of the chamber may be, for example, about 50 µm. The substrate (24) further includes an inlet and outlet for fluid to enter and leave the system (20).

In addition, and as shown in FIG. 12, the mixture (26) forms a film with a predetermined length and width. There is no limitation on the length and width of the film (i.e., the mixture (26)) disposed on the substrate (24). In an embodiment, the length of the film is from 1 to 10 cm, or from 2 to 9 cm, or from 3 to 8 cm, or from 4 to 7 cm, or from 5 to 6 cm. In one embodiment, the length of the film is about 5 cm. The width of the film may be from 0.5 to 2.5 cm, or from 0.7 to 2.3 cm, or from 0.9 to 2.1 cm, or from 1.1 to 1.9 cm, or from 1.3 to 1.7 cm, or from 1.5 to 1.6 cm. In one embodiment, the width of the film is about 1.6 cm.

In an embodiment, the system (20) is further defined as a microfluidic device including at least one microfluidic chamber and/or channel. Typically, larger devices include microfluidic chambers as opposed to microfluidic channels, but this is not necessarily true in every embodiment. In one embodiment, the microfluidic device has one or more microfluidic channels and/or chambers, one or more of which each independently has a length, height, and/or width of from about 1 to 1000 µm (i.e., 1 mm). In various embodiments, one or more of these values is from 1 µm to 100, 5 to 95, 10 to 90, 15 to 85, 20 to 80, 25 to 75, 30 to 70, 35 to 65, 40 to 60, 45 to 55, or 50 to 55, µm. In other embodiments, one or more of these values is from 100 to 1000, from 125 to 975, from 150 to 950, from 175 to 925, from 200 to 900, from 225 to 875, from 250 to 850, from 275 to 825, from 300 to 800, from 325 to 775, from 350 to 750, from 375 to 725, from 400 to 700, from 425 to 675, from 450 to 650, from 475 to 625, from 500 to 600, from 525 to 575, or from 550 to 575 µm. In other embodiments, the width may be up to 5 mm, and the length up to 100 to 1000 mm. The dimensions of the microfluidic device, as a whole, are not particularly limited. In various embodiments, the length may be from about 5 to 100 mm, the width may be from about 5 to 50 mm, and the thickness may be from about 100 µm to 10 mm. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

One of more microfluidic channels and/or chambers may each individually have a unique shape and/or structure. In addition, one microfluidic channel and/or chamber may have a shape or pattern different from another microfluidic channel and/or chamber in the same device. The geometry of these patterns is also not particularly limited. The patterns may be geometric, non-geometric, uniform or non-uniform, e.g. straight, zig-zag, herringbone, circular or oval, triangular, whorl-shaped, ribbon-shaped, marble, spiral-shaped, coil-shaped, curl-shaped, twisted, looped, helix, serpentine, sinusoidal, winding, and/or random, and the like.

Suitable but non-limiting microfluidic devices are described in WO2009/051734 and PCT/US10/53221, each of which is expressly incorporated herein by reference in non-limiting embodiments. Non-limiting examples of microfluidic devices are set forth in FIGS. 13A through 13D. Other suitable, but non-limiting, microfluidic devices are described in S. Wang et al., "Highly Efficient Capture of Circulating Tumor Cells by Using Nanostructured Silicon Substrates with Integrated Chaotic Micromixers," *Angewandte Chemie*, vol 50, pp. 3084-3088, 2011, which is expressly incorporated herein by reference in non-limiting embodiments. As described in this reference, it is contemplated that this disclosure may utilize silicon nanopillars and/or PDMS channels.

The microfluidic device may include one or more walls oriented substantially perpendicularly, or transversely, to a floor, supplemental layers, microfluidic channels and/or microfluidic chambers. The microfluidic device may also have a central body, a longitudinal axis, and upstream and downstream ends opposite each other, wherein the central body defines the microfluidic channel and/or microfluidic chambers which is in fluid communication with the upstream and downstream ends along the longitudinal axis for receiving the fluid sample. The microfluidic device may also include an entrance (i.e. inlet) defined by the central body and disposed at the upstream end of the central body and include an exit (i.e., outlet) also defined by the central body and disposed at the downstream end of the central body wherein both the entrance and exit are disposed transverse to the longitudinal axis.

The geometry of the microfluidic channel and the one or more walls of the microfluidic device is not particularly limited but may be designed to increase or decrease flow through, velocity through, or pressure in, the microfluidic channel.

The microfluidic device may include a single microfluidic channel and/or chamber, two microfluidic channels and/or chambers, or three or more (i.e., a plurality of) microfluidic channels and/or chambers. The microfluidic channels and/or chambers can be arranged in series, in parallel, or in any geometric or puzzle configuration as selected by one of skill in the art. In one embodiment, one or more microfluidic channels and/or chambers are arranged in an approximate herringbone pattern. Each individual microfluidic channel and/or chamber may be used to isolate one or more types of material or rare cells (22). In various embodiments, a sample of blood, bodily fluid, etc. is segmented into two or more segments and the segments flow through different microfluidic channels and/or chambers at one or more pressures and/or velocities.

The microfluidic device may be designed to allow for optical or visual inspection of the microfluidic channels and/or microfluidic chambers. For example, the microfluidic device may include a top, bottom, and/or side, which may be transparent to allow for optical or visual inspection. Alternatively, the microfluidic device may include a top, bottom, and/or side which may be opaque. It is also contemplated that the microfluidic device may not include a top.

In addition, the microfluidic device may be designed to maximize efficiency relative to flow, velocity and/or shear force of a sample passing therethrough. In various embodiments, the maximum shear force exerted on a cell, based on a volumetric flow rate of about 1 mL/h, is about 0.4 dynes/cm$^2$ at q=68°, and the maximum velocity is about 460 µm/s. The shear stress produced in a microfluidic channel and/or microfluidic chamber is typically of from about 0.1 to 20 dyn/cm$^2$ and may be less than 15, 10, 5, 1, or 0.5, dyn/cm$^2$. Shear stress is not necessarily constant throughout a microfluidic channel. In other embodiments, a sample may be transported through the microfluidic channel and/or chamber at a rate of about 0.1 to 30 mL/hr. Typical flow rates are typically from 0.5 to 1, from 1 to 20, 2 to 19, 3 to 18, 4 to 17, 5 to 16, 6 to 15, 7 to 14, 8 to 13, 9 to 12, or 10 to 11, mL/hr. However, these rates are not limiting and the rate at which the sample passes through may be greater or less than those described above. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The volume of the microfluidic channel and/or microfluidic chamber may be customized depending on a volume of the sample used. The volume of the microfluidic channel and/or microfluidic chamber may be smaller or larger than the size of the sample or may be approximately the same as the size of the sample. In various embodiments, the microfluidic device and/or the microfluidic channel and/or microfluidic chamber has a volume of from about 10 µL to 20 mL, from about 100 µL to 15 mL, from about 100 µL to 10 mL, from about 100 to 5 mL, from about 100 µL to 1 mL, or from about 100 µL to 0.5 mL. However, these volumes are not limiting and the volume of the microfluidic device and/or the microfluidic channel and/or microfluidic chamber may be greater or less than those described above. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The microfluidic channel and/or microfluidic chamber may be modified to increase surface area, volume, etc. to increase a probability that a rare cell with be captured. For example, when the walls are substantially planar, the height of the microfluidic channel and/or microfluidic chamber may be designed so that rare cells are more efficiently detected and/or trapped.

The microfluidic device is not particularly limited to any particular efficiency. However, in various embodiments, the microfluidic device can typically identify, enumerate, detect, capture, and/or isolate from 1 to 10,000, 1 to 7,500, 1 to 5,000, 1 to 2,500, 1 to 1500, from 5 to 1000, from 10 to 500, from 25 to 200, or from 50 to 100, rare cells (22) from a blood sample of about 1 mL or less. Alternatively, the system (20) and/or microfluidic device may have a rare cell capture efficiency of at least 1, 5, 10, 15, 20, 25, 30, 35, 40, 45, 50, 55, 60, 65, 70, 75, 80, 85, 90, 95, or 99 percent determined as (rare cells captured on the (functionalized) graphene oxide (or any protein, antibody, marker, etc. bound thereto) divided by a total number of rare cells introduced to the system and/or microfluidic device) multiplied by 100. In other embodiments, the system (20) and/or microfluidic device may have a rare cell capture efficiency of 95 to 100, 90 to 95, 90 to 100, 85 to 95, 85 to 90, 80 to 85, 80 to 90, 80 to 95, 75 to 80, 75 to 85, 75 to 90, 75, to 95, 70 to 75, 70 to 80, 70 to 85, 70 to 90, 75 to 95, 50 to 95, 55 to 90, 60 to 85, 65 to 80, 65 to 75, 65 to 70, 25 to 50, 59 to 75, or 25 to 75 percent, as determined using the formula described immediately above. In various embodiments, the microfluidic device has a rare cell capture efficiency of about 70, 75, or 80 plus or minus about 20, 25, or 30, at 5-20 cells/mL spiked in blood. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

In various embodiments, the microfluidic device and system (20) may capture, on average, about 155±236 CTCs/mL for NSCLC, about 16 to 292 CTCs/mL for metastatic prostate, about 25 to 174 CTCs/mL for localized prostate cancer, about 9 to 831 CTCs/mL for pancreatic cancer cells, about 5 to 176 CTCs/mL for breast cancer cells, and about 42 to 375 (121±127) CTCs/mL for colorectal cancer cells. The microfluidic device may allow captured cells to be grown and cultivated, and/or washed such that non-specifically bound cells, e.g. leukocytes, may be removed which may result in about a $10^6$-fold enrichment. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The microfluidic device may also include or be coupled to one or more components such as reservoirs, pumps, valves, actuators, pipes, tubes, electrodes, meters, computers, electronic monitoring devices, analytical devices, electrical potential and/or resistance monitoring devices, and the like. Those of skill in the art may select one or more of the components to couple to the microfluidic device.

The System (120)

Another embodiment of the system (120) includes the substrate (124), an extension (132) disposed on the substrate, and the mixture (126) disposed on the extension (132). The mixture (126) includes the thermo-responsive polymer (128) and the carrier (130). Similar to the system (20), rare cells (22) in a fluid that come into contact with the mixture (126) disposed on the extension (132) of the system (120) are captured and held by the carrier (130). The rare cells (22) captured by the carrier (130) may be released from the thermo-responsive polymer (128). More particularly, when released, the rare cells (22) remain attached the carrier (130) and the thermo-responsive polymer (128) releases the carrier (130) with the rare cell (22) attached to the carrier (130) as the thermo-responsive polymer (128) dissolves in the surrounding fluid.

Figure 14:
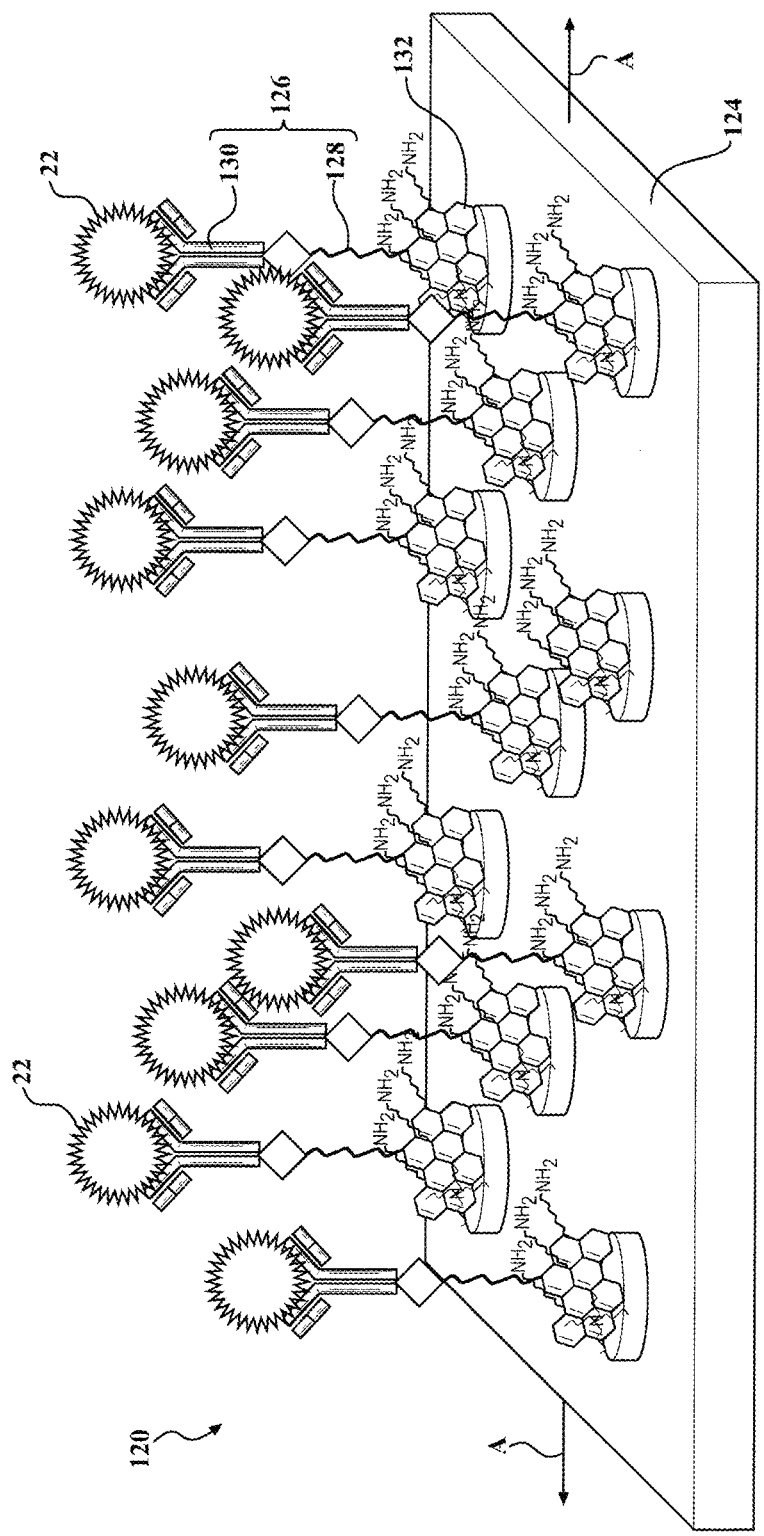
FIG. 14 illustrates an embodiment of a microfluidic device including a magnified view of an extension (e.g. a gold nanopost), a mixture including a thermo-responsive polymer and functionalized graphene oxide disposed on the extension.

The substrate (124) of the system (120) may be same as the substrate (24) for the system (20) described in detail above. In addition, the mixture (126) may be the same as the mixture (26) for the system (20) also described in detail below. However, the mixture (126) in the system (120) is disposed on an extension (132), which is disposed on the substrate (124). As shown in FIG. 14, the extension (132) is coupled to the substrate (124) and extends outwardly from the substrate (124). The terminology "extension" may describe a single extension, two extensions, or a plurality of extensions, in various embodiments, throughout. Said differently, whenever the terminology "extension" is used, that terminology may describe various embodiments including a single extension, two extensions, or a plurality of extensions.

The extension (132) may extend outwardly from the substrate (124) approximately perpendicularly to a longitudinal axis (A) or may extend outwardly at another angle to the substrate (124) and/or the longitudinal axis (A), e.g. at an obtuse or acute angle, such as 30, 45, or 60. The extension (132) may be coupled to the substrate (124) via any means known in the art such as through chemical and physical connections, e.g. with adhesives, via chemical bonding, and the like. Similarly, the extension (132) may be coupled to the substrate (124) in direct contact with the substrate (124) or in indirect contact with the substrate (124), e.g. separated by one or more layers, compounds, molecules, etc. As an additional example, the extension (132) may be disposed in direct contact with an intermediate or supplemental layer or connection which, in turn, may be disposed either directly or indirectly with the substrate (124). It is contemplated that the extension (132) may still be coupled to the substrate (124) even though there is no direct contact therebetween.

Figure 15:
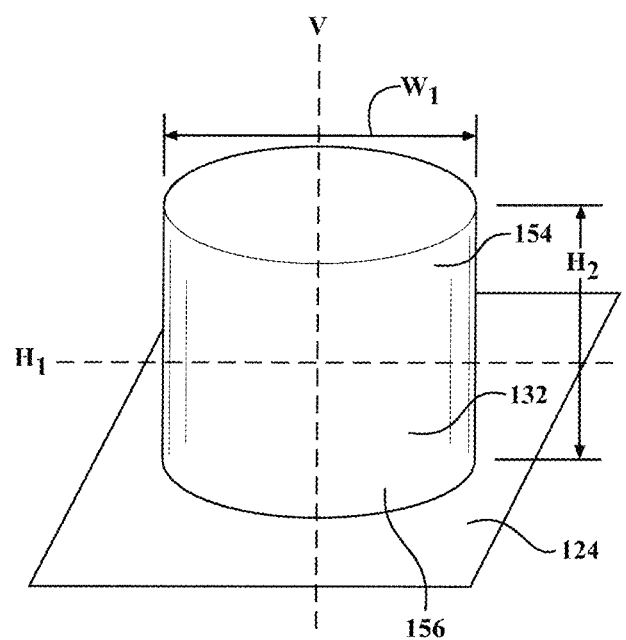
FIG. 15 is a schematic perspective view of an embodiment of an extension disposed on a substrate.

As shown in FIG. 15, the extension (132) typically has an upper end (154) and a lower end (156) and a vertical axis (V) that extends through the upper and lower ends (154, 156). Typically, the upper and lower ends (154, 156) extend along the vertical axis (V). The extension (132) also typically has a horizontal axis ($H_1$) that extends between the upper and lower ends (154, 156).

The extension (132) may be disposed substantially perpendicularly to the substrate (124) and/or horizontal axis ($H_1$) or disposed transversely (i.e., at any angle) to the substrate (124) and/or horizontal axis ($H_1$). It is also contemplated that the extension (132) may be disposed such that the horizontal axis ($H_1$) is disposed approximately parallel to, or transverse to, the substrate (124). The extension (132) may be further defined as a post or rod, e.g. a micro-post, micro-rod, nanopost, nanorod, etc. In one embodiment, the extension (132) is further defined as an electrode. Typically, the extension (132) has micro- or nano-scale dimensions.

In various embodiments, the extension (132), e.g. a nanopost, has a height (e.g. $H_2$) of about 100 nm and a width or radius of about 10 μm. In other embodiments, the extension (132) has a height ($H_2$) of about 10, 15, 20, 25, 30, 35, 40, 45, 50, 55, 60, 65, 70, 75, 80, 85, 90, or 95 nm, or ranges thereof. In still other embodiments, the extension (132) has a height (e.g. $H_2$) of about 105, 110, 115, 120, 125, 130, 135, 140, 145, 150, 155, 160, 165, 170, 175, 180, 185, 190, 200, 205, 210, 215, 220, 225, 230, 235, 240, 245, 250, 255, 260, 265, 270, 275, 280, 285, 290, 295, 300, 325, 350, 375, 400, 425, 450, 475, or 500 nm, or ranges thereof. In even further embodiments, the extension (132) has a height (e.g. $H_2$) of from 10 to 2000, from 50 to 2000, from 100 to 2000, from 200 to 1900, from 300 to 1800, from 400 to 1700, from 500 to 1600, from 600 to 1500, from 700 to 1400, from 800 to 1300, from 900 to 1200, or from 1000 to 1100, nm, or ranges thereof. In other embodiments, the extension (132) has a diameter or width (e.g. $W_1$) of from 100 nm to 1000 micrometers or from 100 nm to 1000 nm, from 150 to 950, from 200 to 800, from 250 to 750, from 300 to 700, from 350 to 650, from 400 to 600, from 450 to 550, or from 500 to 550 nm, or ranges thereof. In still other embodiments, the extension (132) has a diameter or width (e.g. $W_1$) of from 20 to 100, from 25 to 95, from 30 to 90, from 35 to 85, from 40 to 80, from 45 to 75, from 50 to 70, from 55 to 65, or from 60 to 65, nm, or ranges thereof. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

Figure 16:
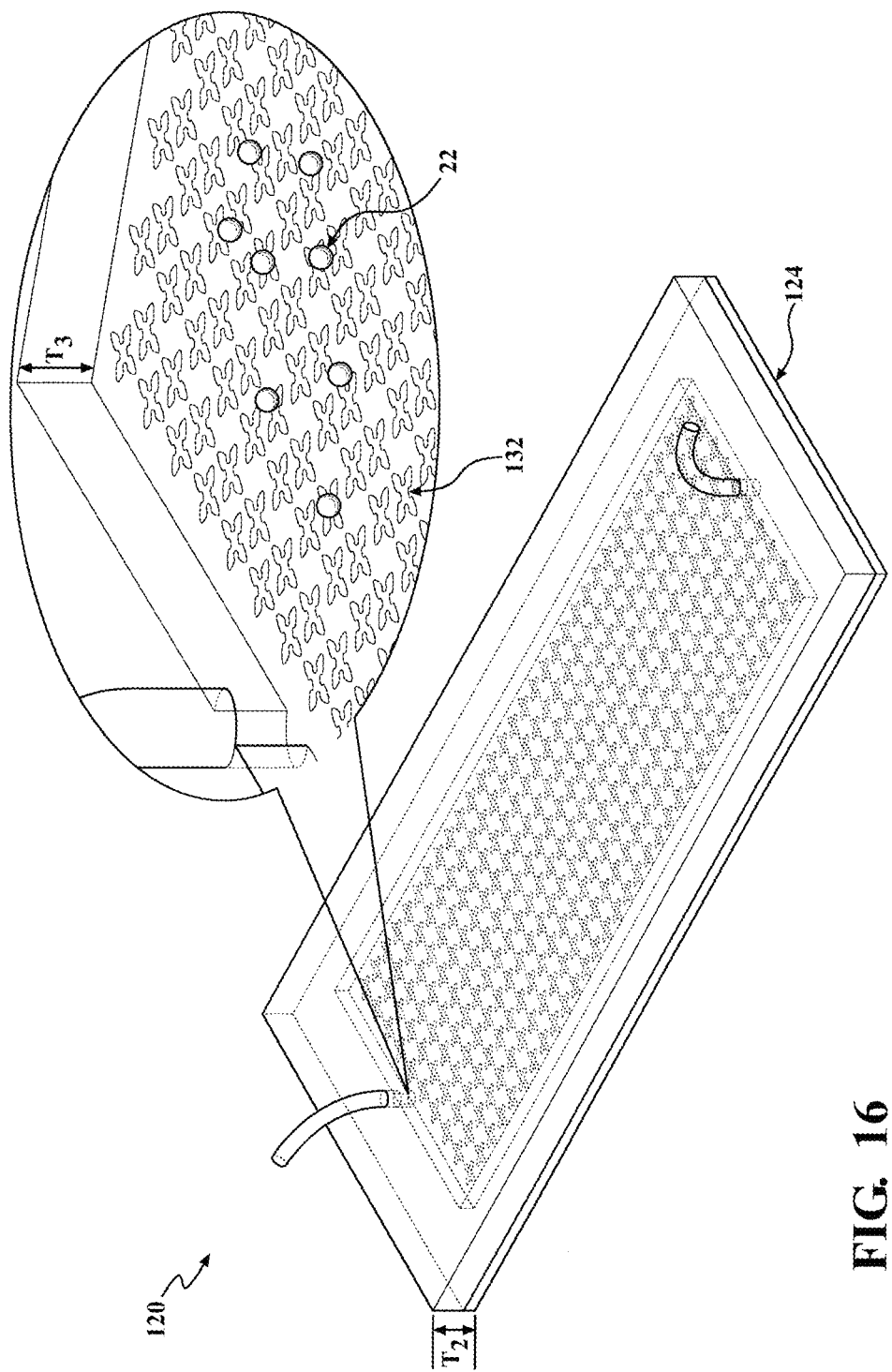
FIG. 16 is an illustration of an embodiment of a microfluidic device including a plurality of extensions, and a magnified portion of the plurality of extensions distributed in leaf patterns on a substrate and rare cells disposed thereon.
Figure 17:
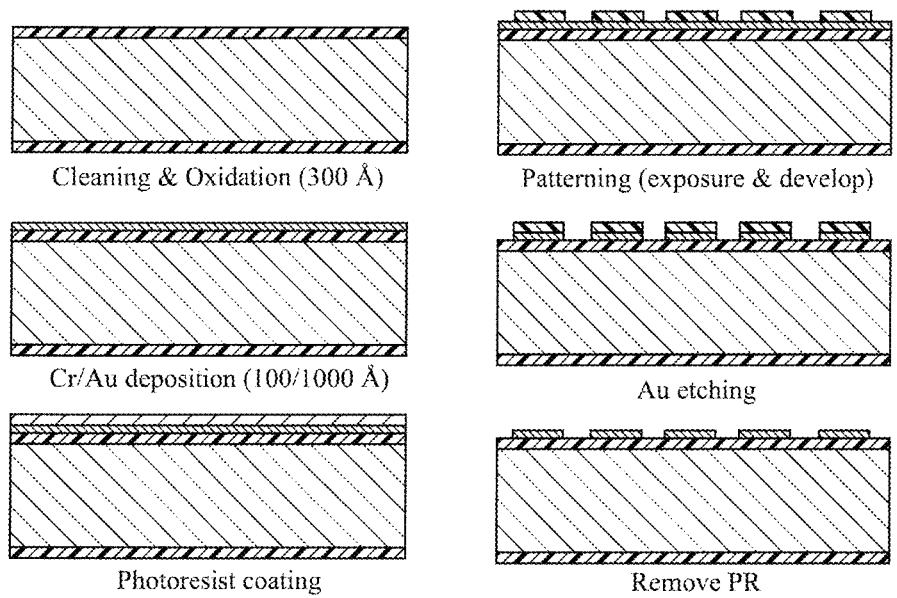
FIG. 17 is a schematic flow diagram of a series of method steps, one or more of which may be utilized to form graphene oxide.
Figure 18:
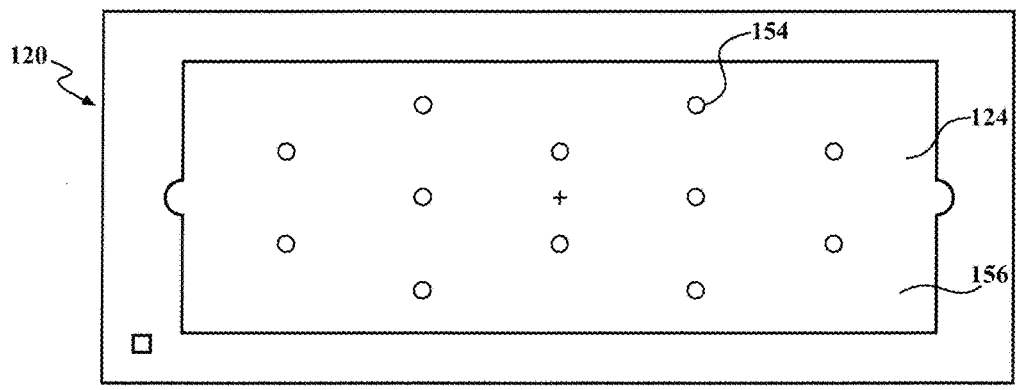
FIG. 18 is a top view of another embodiment of the microfluidic device including a plurality of extensions distributed on the substrate.

It is contemplated that, relative to the height/thickness of a microfluidic device or channel or chamber, described in greater detail below, and e.g. as shown as $T_2$ or $T_3$ in FIG. 16, the extension (132) may appear essentially two dimensional, as could be determined by one of skill in the art. For example, if the height/thickness of a microfluidic device or channel or chamber is from about 40 to 50 μm, even a 500 nm height of an extension (132) is only 1% of the height/thickness of the microfluidic device or channel or chamber. In a similar scenario, a 5 nm height of an extension (132) is only 0.01% of the height/thickness of a microfluidic device, channel, or chamber. Moreover, a 1 nm height of an extension (132) is only 0.002% of the height/thickness of a microfluidic device, channel, or chamber in one embodiment. In similar embodiments, the height of the extension (132) is small, as appreciated by a person of skill in the art, compared to the height/thickness of the microfluidic device, channel, or chamber, that the extension (132) appears to be almost two-dimensional. Similarly, even under light microscopy and modest magnification (e.g. 50-500×), the height of the extension (132) may appear essentially two-dimensional when compared to the height/thickness of the microfluidic device, channel, or chamber, as appreciated by a person of skill in the art.

The extension (132) may be, include, consist essentially of, or consist of, a plastic, polymer (such as polymethylmethacrylate (PMMA)) or metal or combinations thereof. In one embodiment, the metal is gold (e.g. the extension (132) may be formed from gold). Alternatively, the metal may be, include, consist essentially of, consist of, or be chosen from the group of, transition metals, precious metals, rare earth metals, and combinations thereof. In various embodiments, it is contemplated that the extension (132) be, include, consist of, or consist essentially of, a metal, such as gold, silver, and/or copper, and/or a mixed metal compound such as indium-tin oxide (ITO). The terminology "consist essentially of" typically describes that the extension (132) includes one or more of the aforementioned materials and is free of, or includes less than 0.1 or 1 weight percent, of a non-metal or a non-mixed metal compound or another of the aforementioned materials.

The extension (132) may be formed by any method known in the art. In one embodiment, the extension (132) is formed by evaporating and patterning metal layers, e.g. Cr/Au layers (10/100 nm). In various embodiments, the extension (132) can be formed using a lift-off process which typically allows for fine patterns to be formed. A photoresist may be coated on a silicon substrate (124) and patterned by photolithography, see e.g. FIG. 17. Then metal layers may be deposited on the silicon wafer. Subsequently, the substrate (124) may be immersed in acetone or a photoresist remover solution. A patterned gold layer typically remains. In other embodiments, a shadow mask can be used in conjunction with depositing a layer, e.g. a gold layer. Electroplating techniques may also be utilized throughout this disclosure.

The extension (132) may be disposed on any one or more portions or segments of the substrate (124), microfluidic device, channel, and/or chamber. In various embodiments, the extension (132) is disposed on or in/within a microfluidic channel or a microfluidic chamber, as first introduced above. In other embodiments, more than one extension (132) is disposed on or in the substrate (124), microfluidic device, channel, and/or chamber in a pattern, for example, as set forth, for example, in FIG. 18. It is contemplated that a total number of extensions (132) may exceed hundreds, thousands, hundreds of thousands, millions, tens of millions, etc.

The total number of extensions (132) is not particularly limited. The extension (132) itself may be formed in a shape/pattern and/or a plurality of extensions (132) may be, as a whole, set forth in a shape/pattern that may be the same or different than the pattern of any individual extension (132). Each individual extension (132) may have a shape/pattern that is the same or different from any one or more other extensions (132). Similarly, the plurality of extensions may be segmented into one or more segments and each segment may individually have a shape/pattern than is the same or different from the shape/pattern of any other segment and/or from any shape/pattern of any individual extension (132).

The size and geometry of these patterns is also not particularly limited. In one embodiment, the diameter of a pattern for an individual extension (132) is about 20 micrometers. In another embodiment, the unit length of a pattern for an individual extension (132) is about 100 micrometers. As set forth in FIGS. 19A-19C, individual extensions (132) may have a circular, flower, or leaf shape/patterns. However, these shapes and patterns are not particularly limiting. Any of the aforementioned shapes/patterns are not limited and each may individually be further defined as a geometric shape/pattern, a non-geometric shape/pattern, a uniform or non-uniform shape/pattern, or as a gradient shape/pattern. Alternatively, the aforementioned shape/pattern of any one or more independent extensions (132), segments, or plurality of extensions (132) may not have any defined shape or pattern and may be described as random or amorphous. Still further, any of the aforementioned shapes/patterns may be as described below relative to the shapes/patterns of the microfluidic channel and/or microfluidic chamber.

Figures 19A, 19B:
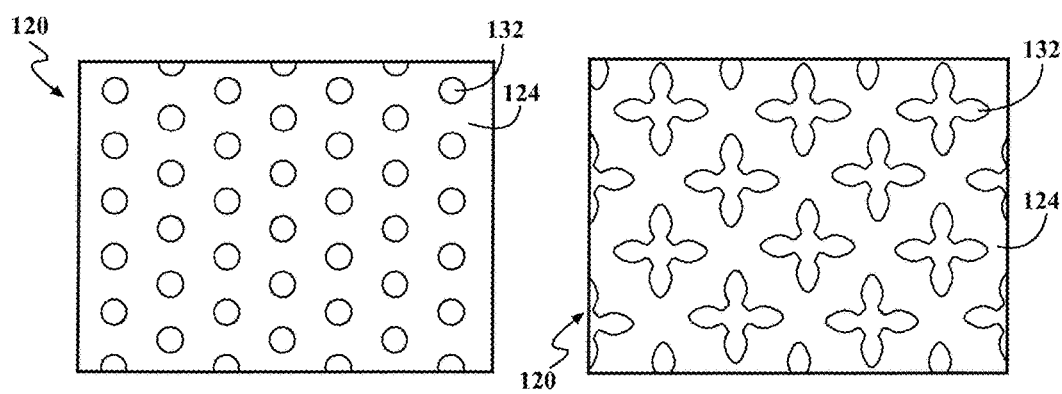
FIG. 19A is an illustration of a circular pattern of extensions (e.g. gold nanoposts) of one embodiment wherein the extensions are disposed on a substrate and each extension has a diameter (e.g. $W_1$) of about 20 μm.
FIG. 19B is an illustration of a flower pattern of extensions (e.g. gold nanoposts) of one embodiment wherein the extensions are disposed on a substrate and the unit length is about 100 μm.
Figure 19C:
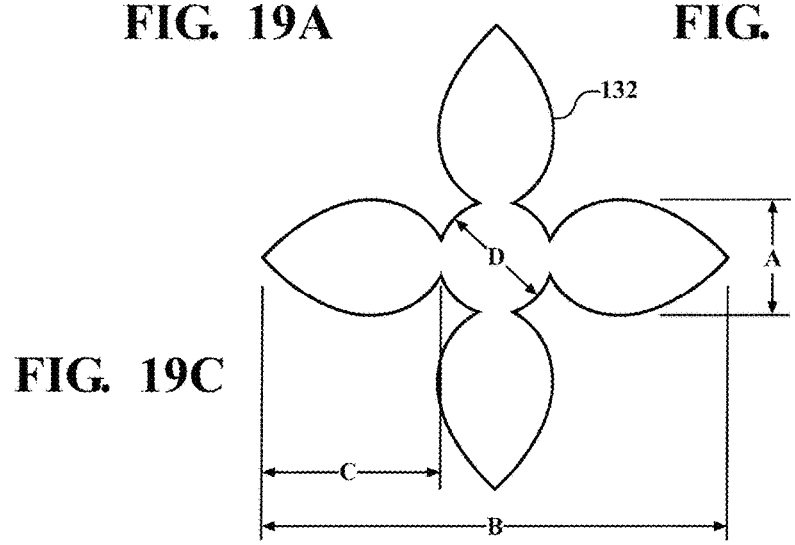
FIG. 19C is a schematic illustration of an extension (e.g. gold nanopost) of one embodiment where the extension is disposed on a substrate in a leaf pattern.

For example, in FIG. 19C, the dimensions of (A) may be about 2 to 500 µm or any other value or range of values set forth in the table of FIG. 20A or any value or range of values therebetween. The dimensions of (B) may be about 5 to 2000 µm or any other value or range of values set forth in the table of FIG. 20B or any value or range of values therebetween. The dimensions of (C) may be about 2 to 1000 µm or any other value or range of values set forth in the table of FIG. 20C or any value or range of values therebetween. The dimensions of (D) may be about 2 to 500 µm or any other value or range of values set forth in the table of FIG. 20D or any value or range of values therebetween. In one embodiment, the dimensions of (A), (B), (C), and (D), are 25 µm, 100 µm, 36.5 µm, and 25 µm, respectively. Any of the aforementioned values may, for example, vary by 1, 2, 3, 4, 5, 10, 15, 20, or 25+% in varying non-limiting embodiments. All values, and ranges of values, between and including the aforementioned values and the values in the tables are also hereby expressly contemplated in various non-limiting embodiments.

In other embodiments, the extensions (132) are disposed in patterns, e.g. patterns having a length, width, and/or spacing of about 150 nm (e.g. with about a 1.5 µm pitch). In still other embodiments, the extensions (132) are disposed with a 1, 2, 3, 4, 5, 6, 7, 8, 9, 10, 15, 20, 25, 30, 35, 40, 45, 50, 55, 60, 65, 70, 75, 80, 85, 90, 95, of 100 µm, distance between extensions (132) and a shift between at least two rows of an independent distance that may be one of the values described immediately above, e.g. 10, 20, 30, 40, 50, 60, 70, 80, 90, or 100 µm, or ranges thereof. In one embodiment, the extensions (132) are disposed in an equilateral triangular arrangement with a 50 µm distance between extensions (132) and a 50 µm shift after every 3 rows. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

In other embodiments, the pitch distances may be from about 1 to 1000 µm (i.e., 1 mm). In various embodiments, the pitch distance is from 1 to 100, 5 to 95, 10 to 90, 15 to 85, 20 to 80, 25 to 75, 30 to 70, 35 to 65, 40 to 60, 45 to 55, or 50 to 55, µm. In other embodiments, the pitch distance is from 100 to 1000, from 125 to 975, from 150 to 950, from 175 to 925, from 200 to 900, from 225 to 875, from 250 to 850, from 275 to 825, from 300 to 800, from 325 to 775, from 350 to 750, from 375 to 725, from 400 to 700, from 425 to 675, from 450 to 650, from 475 to 625, from 500 to 600, from 525 to 575, or from 550 to 575 µm. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

Further details of the extensions (132) and their arrangement on the substrate (124) and forming the system (120) or microfluidic device is set forth in U.S. Patent Publication No. 2015/0285808, the contents of which are incorporated herein in their entirety in various non-limiting embodiments.

The System (220)

Another embodiment of the system (220) includes the substrate (224), an extension (232) disposed on the substrate, and the mixture (226) disposed on the extension (232). The mixture (226) includes the thermo-responsive polymer and the carrier, such as graphene oxide. Similar to the system (20) and (120), rare cells (22) in a fluid that come into contact with the mixture (226) disposed on the extension (232) of the system (220) are captured and held by the carrier. The rare cells (22) captured by the carrier may be released from the thermo-responsive polymer. More particularly, when released, the rare cells (22) remain attached the carrier and the thermo-responsive polymer releases the carrier with the rare cell (22) attached to the carrier as the thermo-responsive polymer dissolves in the surrounding fluid.

The substrate (224) of the system (220) may be same as the substrate (24) for the system (20) described in detail above. In addition, the mixture (226) may be the same as the mixture (26) for the system (20) also described in detail below. However, the mixture (226) in the system (220) is disposed on an extension (232), which is disposed on the substrate (224).

The system (220) also includes the extension (232) coupled to the substrate (224), and extending outwardly from the substrate (224). The terminology "extension" may describe a single extension, two extensions, or a plurality of extensions, in various embodiments, throughout. Said differently, whenever the terminology "extension" is used, that terminology may describe various embodiments including a single extension, two extensions, or a plurality of extensions. In the present embodiment, and as shown in FIGS. 21 and 24, the system (220) includes a plurality of extensions (232) extending outwardly from said substrate (224) and substantially radially arranged about said center axis (C) of the substrate (224).

Figure 21:
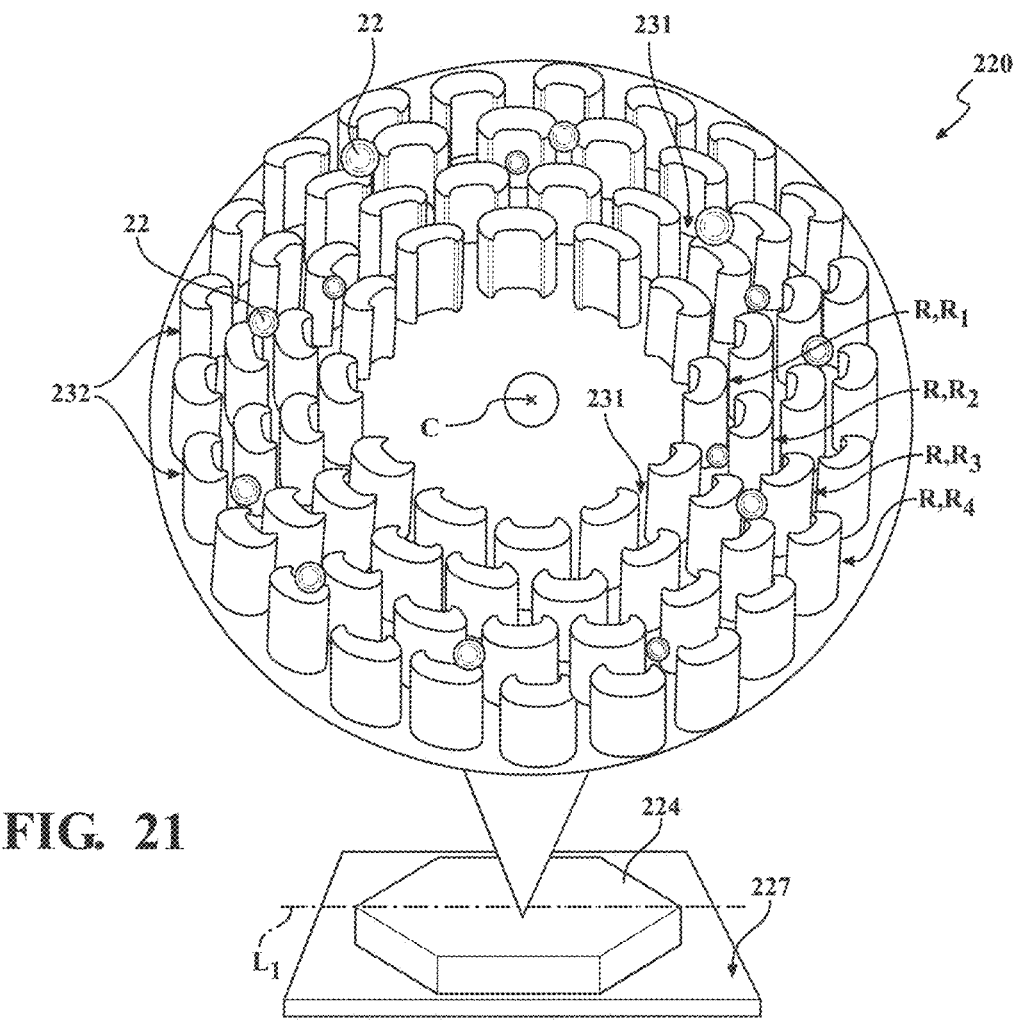
FIG. 21 is a schematic exploded view of another non-limiting embodiment of a microfluidic device including a plurality of bean-shaped extensions arranged about a center axis of a substrate and rare cells (e.g. CTCs) and white blood cells captured by the mixture disposed on the bean-shaped extensions.
Figure 22:
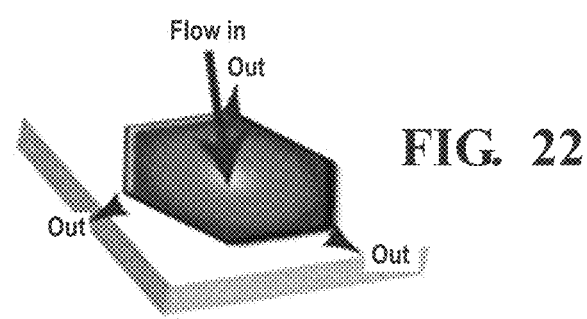
FIG. 22 is a schematic illustration of the microfluidic device of FIG. 21 showing an inlet at the center of the substrate and outlet at an outer edge of the substrate, and further shows a colored fluid flow profile with velocity decreasing from the inlet toward the outlet.

As shown, e.g. in FIG. 21, the extensions (232) may extend outwardly from the substrate (224) approximately perpendicularly to an axis ($L_1$) or may extend outwardly at another angle to the substrate (224) and/or the axis ($L_1$), e.g. at an obtuse or acute angle, such as 30, 45, or 60. The extensions (232) may be coupled to the substrate (224) via any means known in the art such as through chemical and physical connections, e.g. with adhesives, via chemical bonding, and the like. Similarly, the extensions (232) may be coupled to the substrate (224) in direct contact with the substrate (224) or in indirect contact with the substrate (224), e.g. separated by one or more layers, compounds, molecules, etc. As an additional example, the extensions (232) may be disposed in direct contact with an intermediate or supplemental layer or connection which, in turn, may be disposed either directly or indirectly with the substrate (224). It is contemplated that the extension (232) may still be coupled to the substrate (224) even though there is no direct contact therebetween.

In various embodiments, the extensions (232) are arranged about the center axis (C) of the substrate (224). In an embodiment, and as shown in FIG. 21, the extensions (232) may be substantially radially arranged about the center axis (C) of the substrate (224). Further, the system (220) may include the plurality of extensions (232) arranged about the center axis (C) in at least one row (R). As shown in FIG. 21, for example, the system (220) may include the plurality of extensions (232) arranged substantially radially about the center axis (C) in multiple rows (R). For instance, a first row ($R_1$) of extensions (232) may be substantially radially arranged about the center axis (C), a second row ($R_2$) of extensions (232) may be substantially radially arranged about the center axis (C) behind the first row of extensions (232), a third row ($R_3$) of extensions (232) may be substantially radially arranged about the center axis (C) behind the second row of extensions (232), and a fourth row ($R_4$) of extensions (232) may be substantially radially arranged about the center axis (C) behind the third row ($R_3$). While FIG. 21 shows four rows ($R_1$, $R_2$, $R_3$, $R_4$), it is to be appreciated that the system (220) may include any number of rows (R), such as two, three, four, five, six, seven, etc. rows (R) of extensions (232).

Figure 24:
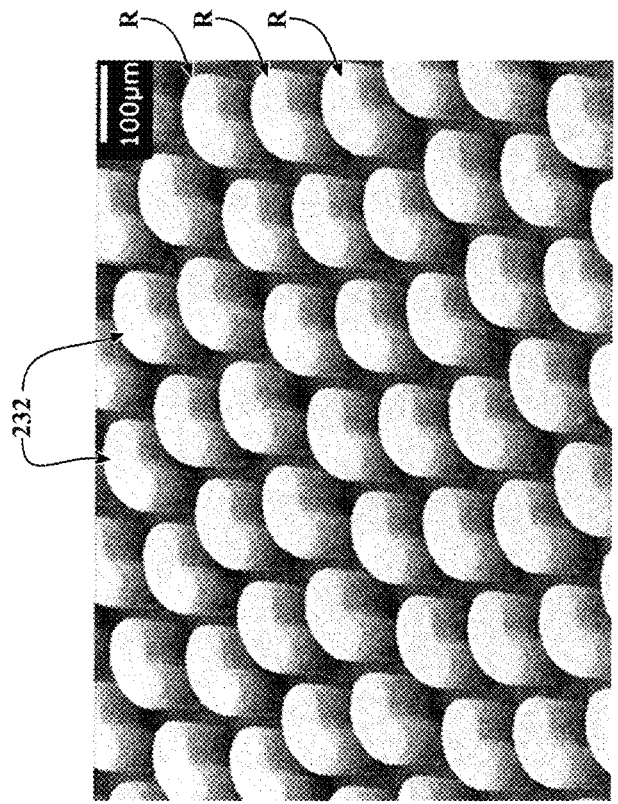
FIG. 24 is a scanning electron microscope (SEM) image of a portion of the microfluidic device of FIG. 23 showing a plurality of bean-shaped extensions.
Figure 23:
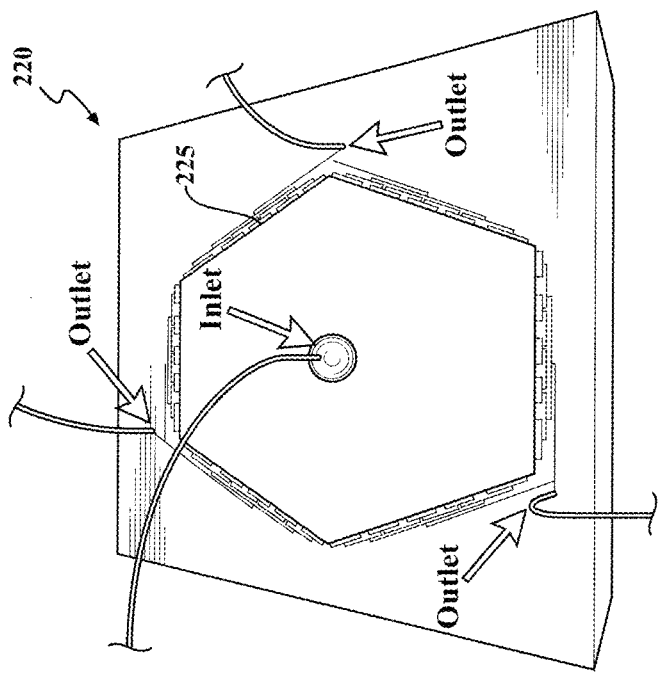
FIG. 23 is a perspective view of the microfluidic device of FIG. 21 with fluid (e.g. blood) flow into the inlet at the center of the substrate and out of the outlets at the outer edges of the substrate.

With reference to FIGS. 21 and 24, the extensions (232) may be substantially radially arranged about the center axis (C) of the substrate (224) in a plurality of rows (R) to define a channel (231) enabling the fluid to move radially from the center axis (C) toward the outer edge (227) of the substrate (224). In an embodiment, the channel (231) is defined between adjacent extensions (232) of each of the plurality of rows (R). For instance, a channel (231) may be defined between adjacent extensions (232) in a single row (such as, for example, the first row ($R_1$), the second row ($R_2$), etc.) of extensions (232). A channel (231) may also be defined between extensions (232) of adjacent rows (R) (such as, for example, a first extension (232) in the first row ($R_1$) and a second extension (232) in the second row ($R_2$) which is adjacent to the first extension (232)). The channels (231) defined between adjacent extensions (232) of each of the plurality of rows (R) and the channels (231) defined between extensions (232) of adjacent rows (R) may be interconnected to form a single channel (231) through which fluid flows from the inlet toward the outlet(s) of the system (220) (as shown, for example, in FIGS. 22 and 23). In an example, and as described in further detail below, fluid (such as bodily fluid) flows through the interconnected channels (231) and rare cells (such as cancer cells) in the bodily fluid contact and interact with the extensions (232) substantially radially arranged about the center axis (C).

In an embodiment, each of the extensions (232) is spaced from an adjacent one of the extensions (232) (in the same row (R) or in adjacent rows (R)) a distance of from about 10 to 100 µm. In another example, each of the extensions (232) is spaced from an adjacent one of the extensions (232) a distance of from about 20 to 50 µm. In still another example, each of the extensions (232) is spaced from an adjacent one of the extensions (232) a distance of from about 26 to 32 µm. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The extensions (232) may be disposed on any one or more portions or segments of the substrate (224) or microfluidic device. In the present embodiment, the plurality of extensions (232) is disposed on or in the substrate (224) or microfluidic device in a radial pattern described above. Further, a total number of extensions (232) may vary and, in some embodiments, may exceed hundreds, thousands, hundreds of thousands, millions, tens of millions, etc. It is to be appreciated that the total number of extensions (232) is not particularly limited.

Figure 25A:
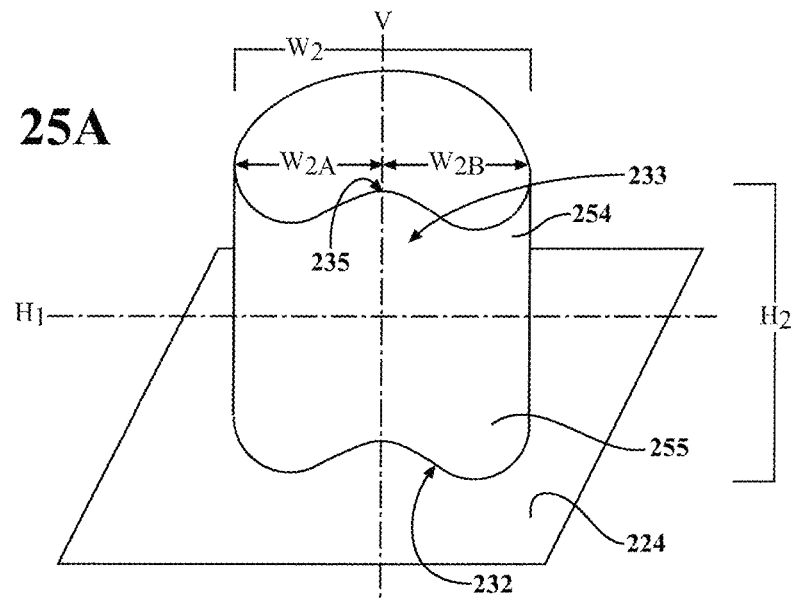
FIG. 25A is a schematic perspective view of a bean-shaped extension disposed on a substrate.
Figure 25B:
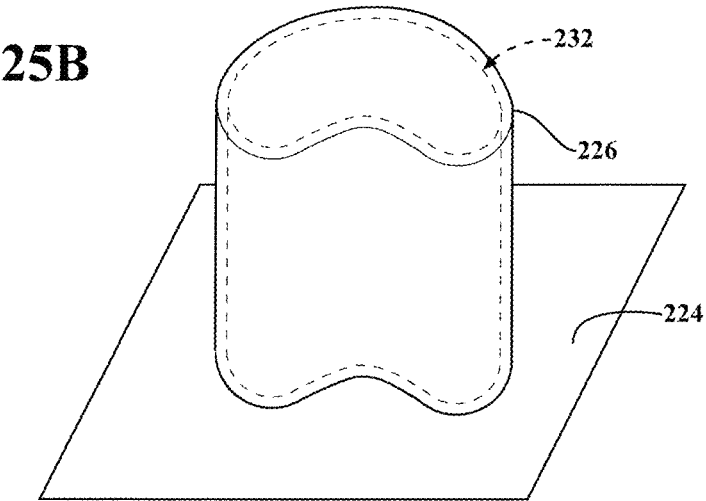
FIG. 25B is another schematic perspective view of the bean-shaped extension disposed on a substrate.
Figure 26A:
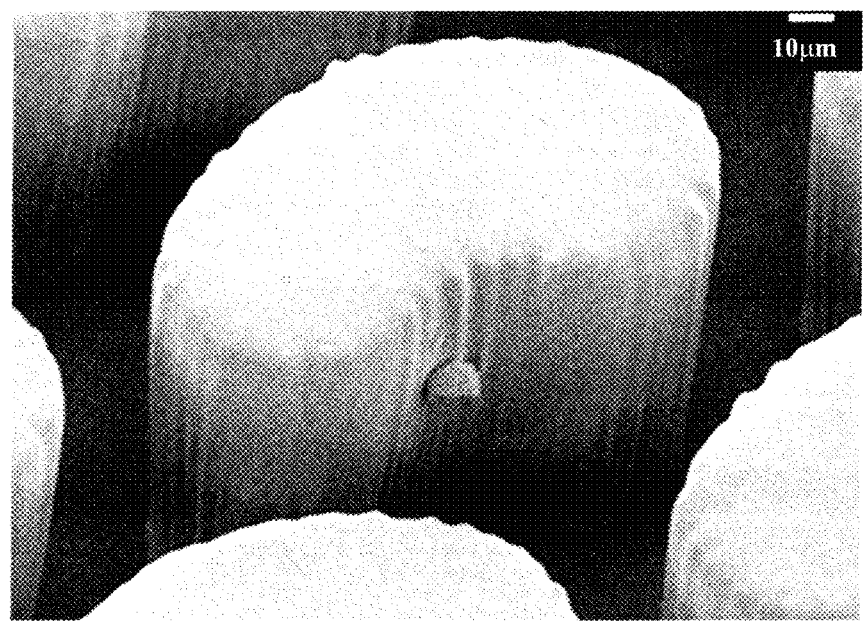
FIG. 26A is an SEM image of a H1650 cell captured on the bean-shaped extension.
Figure 26B:
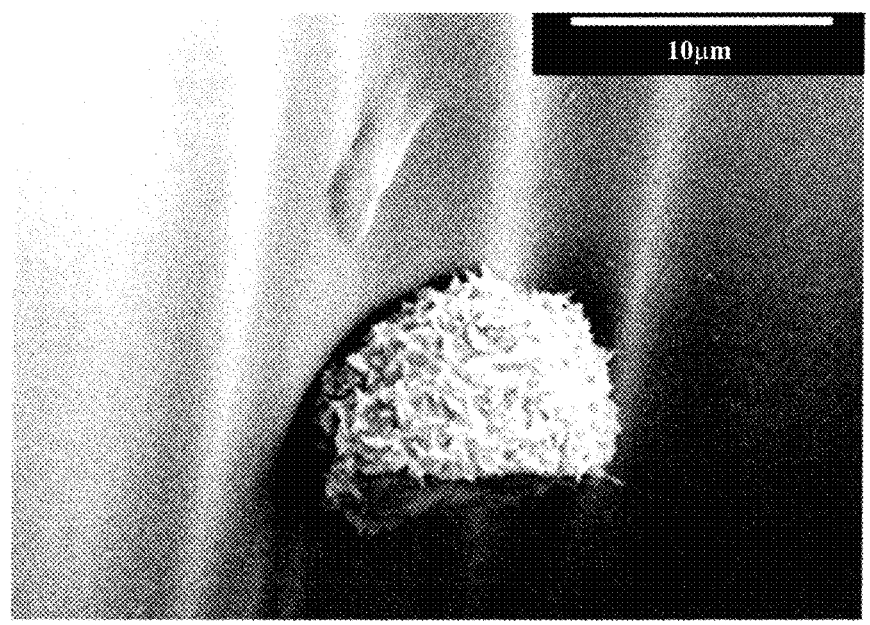
FIG. 26B is an SEM image of a magnified H1650 captured on the bean-shaped extension.

Each extension (232) typically has an upper end (254) and a lower end (255) and a vertical axis (V) that extends through the upper and lower ends (254, 255), as shown in FIG. 25A. Typically, the upper and lower ends (254, 255) extend along the vertical axis (V). The extension (232) also typically has a horizontal axis ($H_1$) that extends between the upper and lower ends (254, 255), as also shown in FIGS. 25A and 25B. At least one of the extensions (232) may be bean-shaped having a concave side (233) with an arc (235). In an embodiment, each of the extensions (232) extending outwardly from the substrate (224) are bean-shaped. Examples of the bean-shaped extensions (232) are shown at least in FIGS. 21, 24, 26A, and 26B. In an example, the arc (235) has an arc angle of from about 75 to 90 degrees. In another example, the arc (235) has an arc angle of from about 80 to 90 degrees. In yet another example, the arc (235) has an arc angle of from about 95 to 90 degrees. In another example, the arc (235) has an arc angle of about 90 degrees. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The extensions (232) may be disposed substantially perpendicularly to the substrate (224) and/or horizontal axis ($H_1$) or disposed transversely (i.e., at any angle) to the substrate (224) and/or horizontal axis ($H_1$). It is also contemplated that the extensions (232) may be disposed such that the horizontal axis ($H_1$) is disposed approximately parallel to, or transverse to, the substrate (224). Each of the extensions (232) may be further defined as a post or rod, e.g. a micro-post, micro-rod, nanopost, nanorod, etc. In one embodiment, each of the extensions (232) is further defined as an electrode. Typically, the extension (232) has micro- or nano-scale dimensions.

In various embodiments, each of the extensions (232), e.g. a nanopost, has a height (e.g. $H_2$) of from about 1 to 5 nm and a width (e.g. $W_2$) of from about 40 to 60 µm. In other embodiments, each extension (232) has a height ($H_2$) of about 1, 1.5, 2, 2.5, 3, 3.5, 4, 4.5, or 5 nm, or ranges thereof. In other embodiments, each extension (232) has a width (e.g. $W_2$) of 40, 41, 42, 43, 44, 45, 46, 47, 48, 49, 50, 51, 52, 53, 54, 55, 56, 57, 58, 59, or 60 µm, or ranges thereof. In an example, the width ($W_2$) of each extension (232) may include a first width ($W_{2A}$) extending from the center of the arc to a first end of the extension (232) and a second width ($W_{2B}$) extending from the center of the arc to a second end of the extension (232). In an example, the first width ($W_{2A}$) of the extension (232) ranges from about 100 to 250 µm, from about 150 to 200 µm, or from about 175 to 195 µm, or ranges thereof, and the second width ($W_{2B}$) of the extension (232) ranges from about 100 to 250 µm, from about 150 to 200 µm, or from about 175 to 195 µm, or ranges thereof. In an example, the first ($W_{2A}$) and second ($W_{2B}$) widths are substantially equal. In another example, the first ($W_{2A}$) and second ($W_{2B}$) widths are different. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The extensions (232) may be, include, consist essentially of, or consist of, a plastic, polymer (such as polymethylmethacrylate (PMMA)) or metal or combinations thereof. In one embodiment, the metal is gold (e.g. the extension (232) may be formed from gold). Alternatively, the metal may be, include, consist essentially of, consist of, or be chosen from the group of, transition metals, precious metals, rare earth metals, and combinations thereof. In various embodiments, it is contemplated that the extension (232) be, include, consist of, or consist essentially of, a metal, such as gold, silver, and/or copper, and/or a mixed metal compound such as indium-tin oxide (ITO). The terminology "consist essentially of" typically describes that the extension (232) includes one or more of the aforementioned materials and is free of, or includes less than 0.1 or 1, weight percent, of a non-metal or a non-mixed metal compound or another of the aforementioned materials.

The extensions (232) may be formed by any method known in the art. In one embodiment, the extensions (232) are formed by evaporating and patterning metal layers, e.g. Cr/Au layers (10/100 nm). In various embodiments, the extensions (232) can be formed using a lift-off process which typically allows for fine patterns to be formed. A photoresist may be coated on a silicon substrate (224) and patterned by photolithography, see e.g. FIG. 17. Then metal layers may be deposited on the silicon wafer. Subsequently, the substrate (224) may be immersed in acetone or a photoresist remover solution. A patterned gold layer typically remains. In other embodiments, a shadow mask can be used in conjunction with depositing a layer, e.g. a gold layer. Electroplating techniques may also be utilized throughout this disclosure.

Further details of the extensions (232) and their arrangement on the substrate (224) and forming the system (220) or microfluidic device is set forth in U.S. Patent Publication No. 2015/0285808, the contents of which are incorporated herein in their entirety.

The System 320

Another embodiment of the present disclosure provides a system (320) comprising a substrate (324) and a mixture (326) disposed on the substrate (324), where the mixture (326) includes a thermo-responsive polymer and a carrier. The system (320) is the same as the system (220) described above, except that the system (320) does not include extensions. In the present embodiment, the mixture (326) is disposed directly on the substrate (324). In addition, fluid flows from an inlet at the center of system (320) and flows radially outwardly toward an outlet at an outer edge of the substrate (324).

Method for Forming the System (20), (120), (220), (320)

This disclosure also provides a method of forming the system (20), (120), (220), (320) and/or a microfluidic device. The method of forming the systems (20), (320) typically includes the steps of providing the substrate (24), (324) and disposing the mixture (26), (326) on the substrate (24), (324). The method of forming the system (120), (220) includes providing the substrate (124) (224), disposing the extension (132), (232) on the substrate (124), (224), and disposing the mixture (126), (226) on the extension (132), (232).

For the method of forming the systems (120), (220), the step of disposing the extension (132), (232) is also not particularly limited and may include any method of forming and/or depositing the extension (132), (232) on the substrate (124), (224). For example, the method may include the step of evaporating and patterning metal (e.g. Cr/Au) layers. Alternatively, the method may include the step of etching silicon to form the extension (132), (232). In addition, the step of providing the mixture (26), (126), (226), (326) includes forming the mixture (26), (126), (226), (326) as previously described.

Method for Detecting Rare Cells:

This disclosure also provides a method for detecting rare cells using the system (20), (120), (220), (320) and/or microfluidic device of this disclosure. The method allows for small amounts of bodily fluid to be evaluated accuracy and precisely and in a time and cost effective manner to determine the presence of rare cells.

The method includes the steps of providing the system (20), (120), (220), (320) and/or microfluidic device and introducing a sample of bodily fluid to the system (20), (120), (220), (320) and/or microfluidic device such that the sample interacts with the carrier (30), (130) and the rare cells (22) are captured by the carrier (30), (130). The method further includes the step of releasing the captured rare cells attached to the carrier (30), (130) when a temperature of the system (20), (120), (220), (320) is below the LCST of the thermo-responsive polymer. The method allows for small amounts of bodily fluid to be evaluated accuracy and precisely and in a time and cost effective manner to determine the presence of rare cells (22). The step of providing the system (20), (120), (220), (320) and/or microfluidic device is not particularly limited and may include one or more of the aforementioned steps described as associated with the method of forming the system (20), (120), (220), (320) and/or the microfluidic device.

The step of introducing a sample of bodily fluid is also not particularly limited. Typically, this step is further defined as exposing the system (20), (120), (220), (320) and/or the microfluidic device and/or the extension (132), (232) to the bodily fluid such that the bodily fluid contacts the mixture (26), (126), (226), (326) including the carrier (30), (130), which is typically modified or functionalized in such as a way as to interact with the bodily fluid in a designated manner. In one embodiment, the step of introducing the bodily fluid is further defined as injecting or adding the bodily fluid to the entrance or inlet of the microfluidic device. The method may also include the step of flowing the bodily fluid through the microfluidic channel(s) and/or microfluidic chamber(s). For the systems (20), (120), the step of flowing the bodily fluid through the channel and/or chamber occurs, e.g. along the longitudinal axis, from the upstream end towards the downstream end and out of the exit.

Another embodiment of the method for detecting rare cells in the fluid utilizes the systems (220), (320). In this embodiment, the method includes introducing a sample of fluid containing the rare cells into the inlet of the system (220), (320) such that the sample of fluid flow radially from the inlet toward the outer edge of the substrate. In an embodiment, the step of introducing the sample is accomplished at a rate of up to about 10 mL/hr. Furthermore, the rate decreases as the fluid flows from the inlet of the system towards the outer edge of the substrate (224), (324). The method further includes capturing the rare cells as the rare cells interact with the carrier (130) of the mixture (226), (326). Further, the method includes the step of releasing the captured rare cells with the carrier (130) when a temperature of the system (220), (320) is below the LCST of the thermo-responsive polymer.

Method for Diagnosing a Disease:

This disclosure also provides a method for diagnosing a disease, such as cancer or carcinoma in a subject. This method includes the step of introducing a sample of a bodily fluid to the system (20), (120), (220) and determining whether any target rare cells (22) are present. Rare cells (22) obtained by the methods of the disclosure may be assayed for genetic information. In addition, the rare cells (22) may be assayed for changes in genetic information over time as well as or in the alternative to enumeration, e.g. to monitor for the appearance of mutations that indicate a change in therapy is advisable.

Method for Lysing Rare Cells:

This disclosure further provides a method of lysing rare cells (22) using the system (20), (120), (220), (320) of this disclosure. This method typically includes the step of introducing a sample of a bodily fluid to the system (20), (120), (220), (320) and subsequently introducing a lysing agent to the system. The lysing agent may be any known in the art.

One or more methods of this disclosure may also include the step of washing the rare cells (22) at a high shear stress or volume to increase purity and reduce the number of weakly bound or non-specifically bound rare cells (22) in the system (20), (120), (220), (320) and/or microfluidic device. One or more methods of this disclosure may also include the step of counting or quantifying a number of bound rare cells (22). The rare cells (22) can be counted by any method known in the art, including optical, e.g. visual inspection, automated counting, microscopy based detection, FACS, and electrical detection, e.g. with the use of Coulter counters. Counting of the rare cells (22) can be useful for diagnosing diseases, monitoring the progress of disease, and monitoring or determining the efficacy of a treatment. The number of rare cells (22) may also be counted in non-medical applications, e.g. for determination of the amount, presence, or type of contaminants in environmental samples, pharmaceuticals, food, or cosmetics.

One or more of the methods of this disclosure may also include the step of measuring a desired characteristic of rare cells (22). For example, the method may include the step of measuring desired biological properties of rare cells (22) such as mRNA expression, protein expression, and DNA quantification.

Alternative Embodiments

In an embodiment, the present disclosure also provides a functionalized thermo-responsive polymer for capture and release of an entity in a fluid. In this embodiment, the thermo-responsive polymer may include a homo-polymer from any of the homo-polymers having a tunable LCST identified above. In addition, the thermo-responsive polymer is functionalized with at least one functional group, such as an aliphatic group, an aromatic group, a nitrogen group, a carboxyl group, a sulfur including group, and a phosphorus including group. The functionalized thermo-responsive polymer can capture and release the entity (such as rare cells) in a fluid without having to include a separate carrier (such as graphene oxide). In addition, the functionalized thermo-responsive polymer includes appropriate functional groups for capture and release of any suitable entity in a fluid, such as rare cells, proteins, etc.

It is also contemplated that the disclosure may include one or more elements, one or more methods, one or more devices, and/or one or more systems as described in one or more of the following references, each of which is expressly incorporated herein by reference, in one or more non-limiting embodiments: Y. Shao, J. Wang, H. Wu, J. Liu, I. A. Aksay, Y. Lin, "Graphene Based Electrochemical Sensors and Biosensors: A Review," *Electroanalysis*, Vol 22, pp. 1027-1036, 2010; Y. Liu, D. Yu, C. Zeng, Z. Miao, L. Dai, "Biocompatible Graphene Oxide-Based Glucose Biosensors," *Langmuir*, vol. 26, pp. 6158-6160, 2010; J. H. Jung et al., "A Graphene Oxide Based Immuno-biosensor for Pathogen Detection," *Angewandte Chemie*, vol. 122, pp. 5844-5847, 2010.

EXAMPLES

Formation of a Microfluidic Device

A microfluidic device for processing of patient blood samples is formed having a two-dimensional, planar capture system using nanomaterial graphene oxide. The microfluidic device bottom substrate is coated with a composite film of functionalized graphene oxide dispersed in a matrix of thermo-responsive polymer with a lower critical solution temperature (LCST) of about 13° C. Surface available functionalized graphene oxide provides anchors for attaching a CTC capture antibody while the polymer matrix provides temperature dependent modulation of capture or release functionality. The microfluidic device is fabricated by drop-casting a polymer-graphene oxide blend on a patterned surface modified substrate.

The microfluidic device is usable at room temperature. This may be due to the polymer matrix having a LCST of about 13° C. as opposed to higher temperatures, such that there is no inadvertent release of the cells during capture. Further, cell release occurs under gentle conditions, which maximizes the viability of the released cells. The consolidation of advantageous properties of the graphene oxide-based capture with release functionality of the chosen polymer yields a microfluidic device that enables the study of the rare cells without the shortcomings of prior technologies, while presenting an easy and scalable fabrication method.

Formation of a Tunable Thermo-Responsive Polymer

Figure 28:
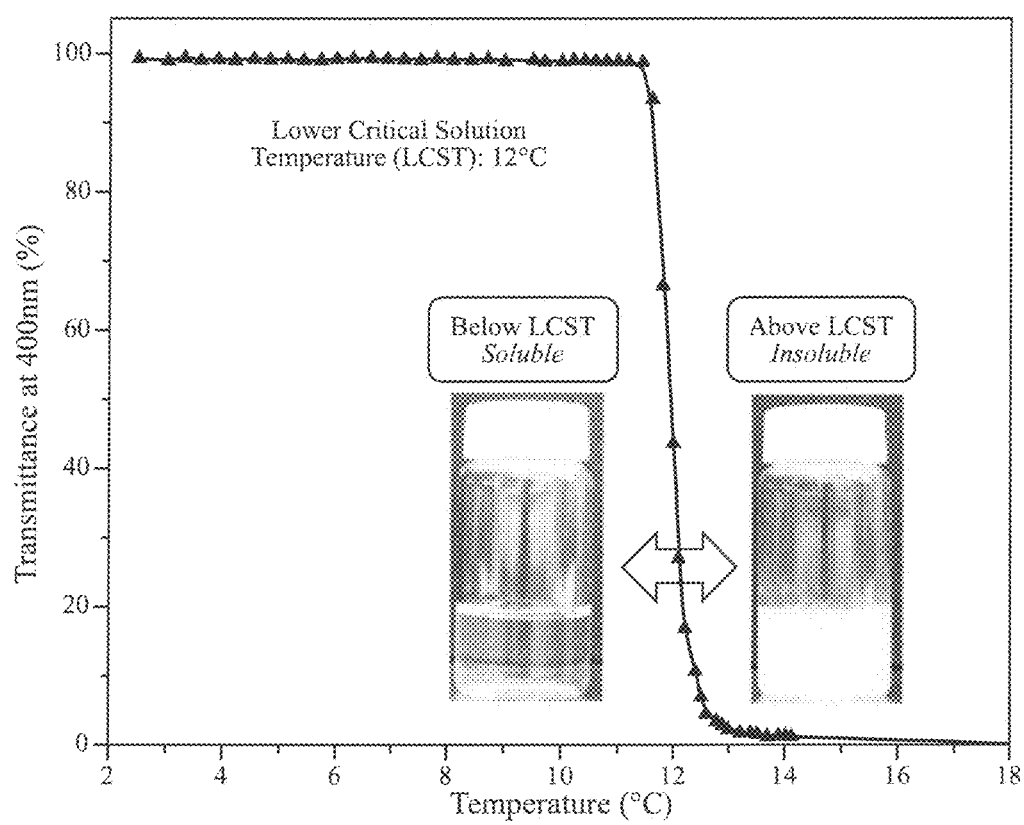
FIG. 28 is a graph showing an ultraviolet-visual transmittance versus temperature for the copolymer poly(N-acryloyl piperidine-co-N,N-diethyl acrylamide), which shows that the copolymer has a lower critical solution temperature (LCST) of about 12° C.

A tunable thermo-responsive polymer is created as shown in FIG. 9. Copolymer poly(N-acryloyl piperidine-co-N,N-diethyl acrylamide) is synthesized via free radical polymerization using AIBN as an initiator. The polymer is characterized for its molecular weight and LCST, as shown in FIG. 28. The LCST is modulated by employing a copolymerization technique using two acrylamide monomers with different degrees of hydrophobicity: N-acryloyl piperidine (AP) and N,N-diethyl acrylamide (DEA). The homopolymers poly(N-acryloyl piperidine) (PAP) and poly(N,N-diethyl acrylamide) (PDEA) have LCST's of about 4° C. and about 25° C., respectively. The capture/release modulation temperature for the microfluidic device may be achieved by changing the ratio of the two monomers in the copolymer. As shown, for example, in FIG. 28, a copolymer synthesized with 7:3 molar ratio of AP:DEA shows a critical temperature of about 12-13° C.

Figure 29:
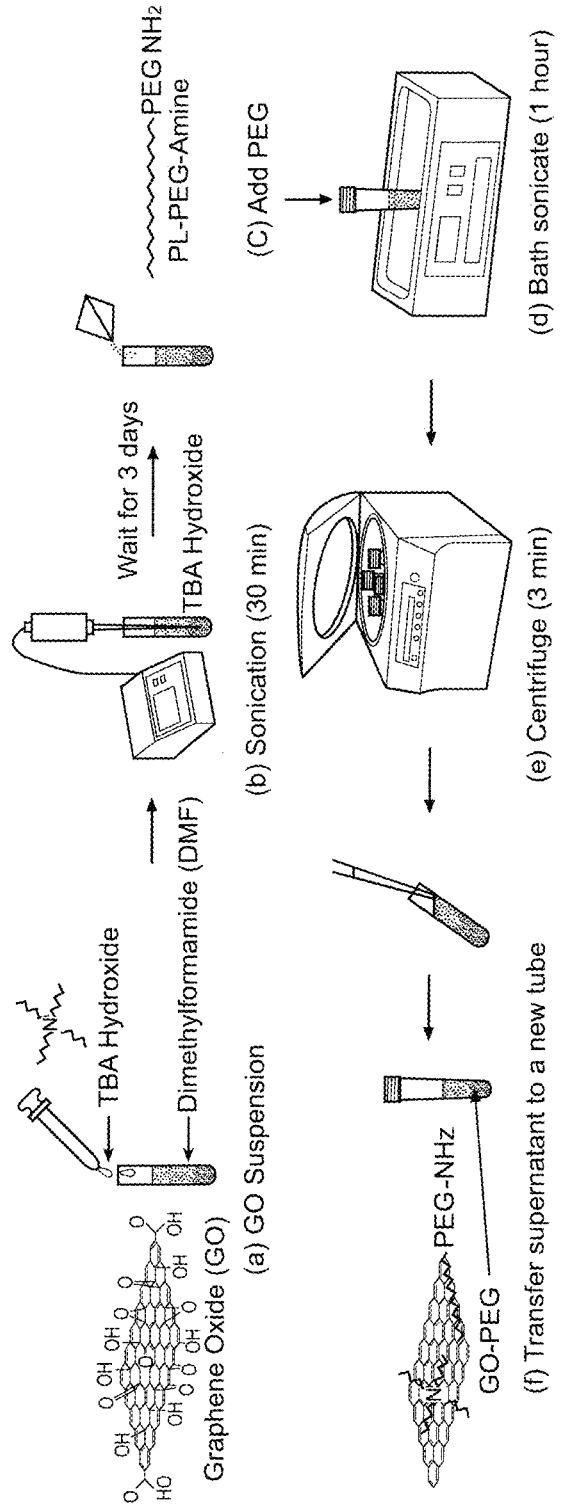
FIG. 29 is a flow diagram illustrating a process for preparing a PEG functionalized graphene oxide suspension.
Figure 30:
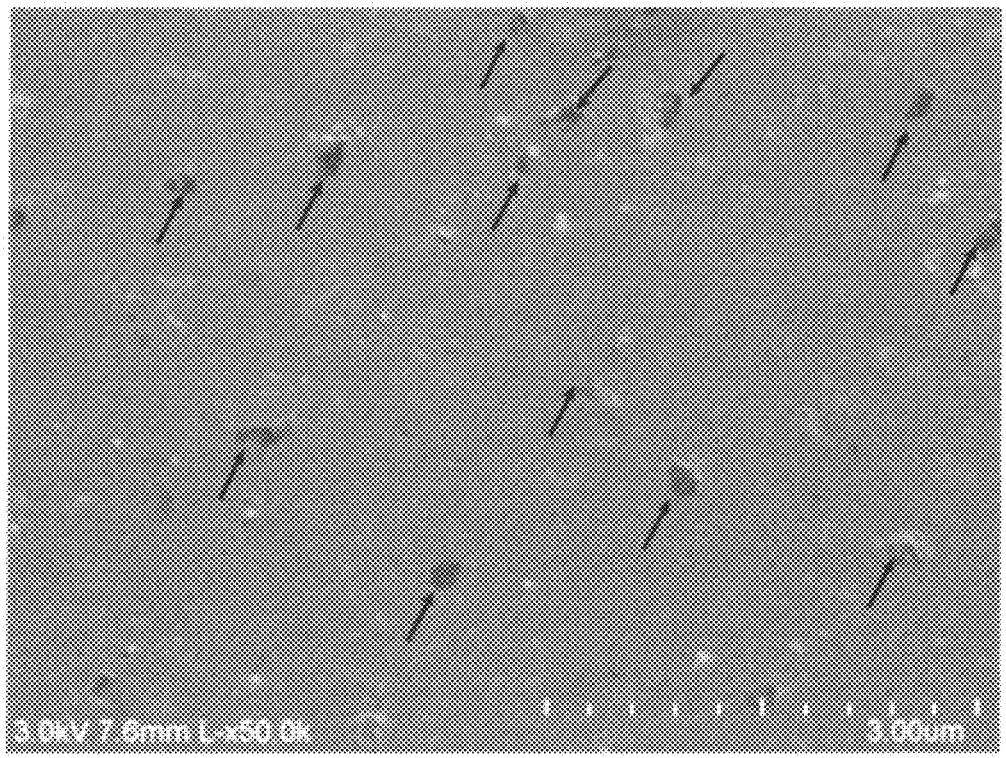
FIG. 30 is a SEM image of a polymer-graphene oxide composite surface, where the arrows indicate suspended graphene oxide present on the surface of the film.

The polymer-functionalized graphene oxide may be prepared as follows. With reference to FIG. 29, about 10 mg of single layer graphene oxide (SLGO) powder is prepared by a modified Hummer's method (Cheap Tubes Inc.). About 10 mL of N,N-dimethylformamide (DMF) and about 300 µL of tetrabutylammonium (TBA) hydroxide (40% in water) are added to form a graphene oxide suspension (as shown in part (a)). Using a tip sonicator, the graphene oxide suspension is ultrasonicated for about 30 minutes (as shown in part (b)). To avoid temperature increase during sonication, a temperature sensor is monitored and the suspension tube is immersed in an ice bath. The suspension is reserved for 3 days at room temperature. About 4 mL of the supernatant was extracted and about 15 mg of phospholipids-polyethylene glycoamine (PL-PEG-$NH_2$) is dissolved (as shown in part (c)), bath sonicated for about 1 hour (as shown in part (d)), and subsequently centrifuged at 12,000 rpm for about 3 minutes (as shown in part (e)). The supernatant is collected and stored at about 4° C. (as shown in part (f)). The supernatant includes PEG functionalized graphene oxide. Polymer-GO nanocomposite films are prepared by dropcasting a DMF solution of the polymer and functionalized GO. The drop-cast films are dried at 60° C. in oven for about 2-3 hours to yield a 3-4 mm thick composite film. An SEM image of polymer-GO composite surface is shown in FIG. 30.

Fabrication of the Polymer-GO Microfluidic Device

The polymer-GO microfluidic device for cell capture and release is fabricated in two steps. It is noted that poly (ethylene glycol) (PEG) tends to render surfaces non-fouling, and the PEG monolayer is used to avoid recapturing of the released CTCs on the glass substrate. In a first step, the polymer-GO composite film is deposited on a patterned and surface-modified glass substrate followed by assembly with a PDMS chamber to form a microfluidic device. In a second step, the device is functionalized by immobilizing anti-EpCAM on the surface available GO through a cross-linker (N-γ-maleimidobutyryl-oxysuccinimide ester, sulfo-GMBS) and avidin-biotin mediated bio-conjugation, providing cell capture/release functionality.

Surface Availability of Amine Groups in the Polymer-GO Composite Films

Figure 31A:
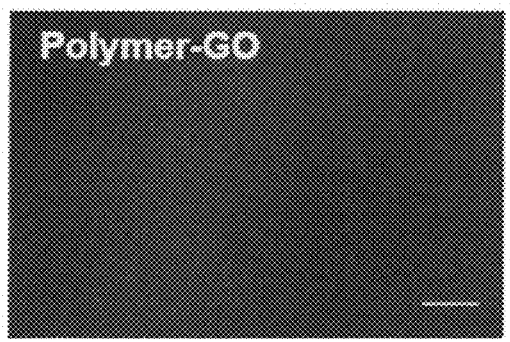
FIGS. 31A-31B are fluorescence images of a polymer film (FIG. 31A) and a polymer-graphene oxide film (FIG. 31B), where the films are incubated with an amine-reactive dye for about 30 minutes at about 40° C. The scale bar for both images is 20.0 μm.
Figure 31B:
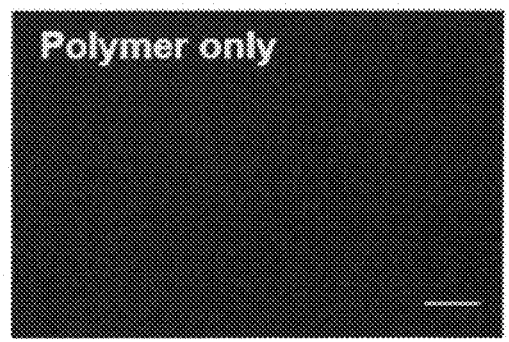

To show the surface availability of the amine groups from the GO-PEG in polymer-GO composite films, drop-cast films are incubated with 0.25 mM aqueous solution of an amine reactive dye, FSE (5-(and-6)-carboxyfluorescein, succinimidyl ester (Life Technologies)) for about 30 minutes at about 40° C., and then washed with copious amount of dionized water. The dye treated films are imaged using a fluorescence microscope (Olympus BX51 coupled with Olympus DP71 camera and EXFO X-cite Series 120 light source). As shown in FIG. 31A, polymer-GO composite films showed bright green fluorescence from the surface tethered dye. In contrast, and as shown in FIG. 31B, the polymer (which does not include the graphene oxide) film showed very low to no fluorescence. It is believed that the dye molecules are primarily tethered to the surface through covalent bonding between the amine groups on film surface and succinimidyl ester groups on the dye. This is suggested by a large contrast in fluorescence intensity from the polymer-GO and polymer-only films.

Time Dependence of Dissolution of Polymer-GO Composite Films in Water

Time dependence of dissolution of polymer-GO composite films in cold water is also determined. Dye treated films are dipped in cold water for different lengths of time and the fluorescence images before and after dipping are compared. Films are dipped in cold water (at a temperature of about 5° C.) for 5, 10, 20, and 30 minutes, and in room temperature water (at a temperature of about 20° C.) for 30 minutes. The beakers with the dipped films are kept on an orbital shaker to weakly simulate conditions in microfluidic devices where the films are subjected to shearing by the flowing fluids. While the film is completely dissolved and washed off in 20 to 30 minutes under cold conditions as evident from gradual disappearance of green fluorescence, the film remains stable and intact at room temperature even after 30 minutes. It is to be understood that in the actual device, the dissolution time is typically much shorter at 10 minutes, which may be due to the shear of the constant flow rate.

Verification of the Conjugation Chemistry

Figure 32A:
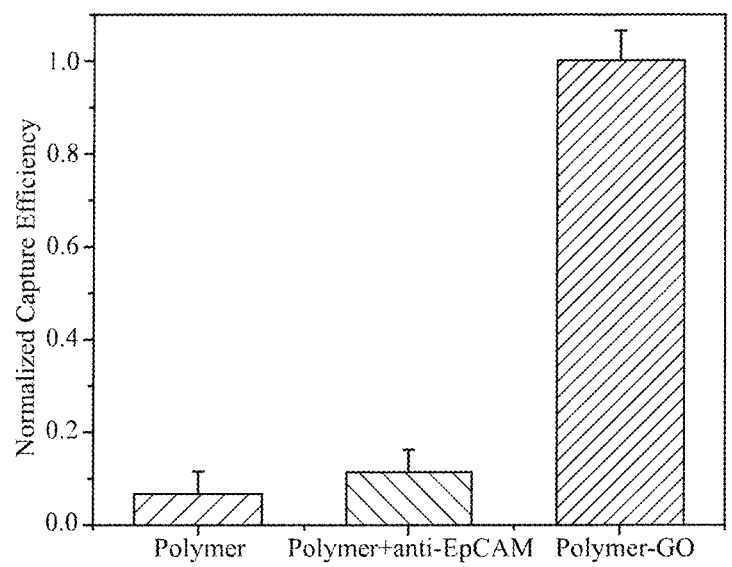
FIG. 32A is a graph showing a capture efficiency of microfluidic devices featuring a thermo-responsive polymer, a thermo-responsive polymer and a non-specifically bound anti-EpCAM, and a polymer-graphene oxide film with specific conjugation chemistry.

To verify the steps of the conjugation chemistry, experiments are performed to compare capture by (1) a polymer film lacking GO alone, (2) a polymer film lacking GO with the addition of anti-EpCAM, and (3) the polymer-GO film with full conjugation chemistry. As shown in FIG. 32A, the two control films show significantly lower levels of capture with the polymer film and the polymer film with antibody capturing at 6.4% and 11.0% the level of the full chemistry, respectively. The increase in capture of the polymer with antibody condition may be a result of physically adsorbed anti-EpCAM. This also suggests that very little of the capture antibody on the fully functional device is non-specifically bound.

Testing of the Performance of the Polymer-GO Device for CTC Capture

Figure 32B:
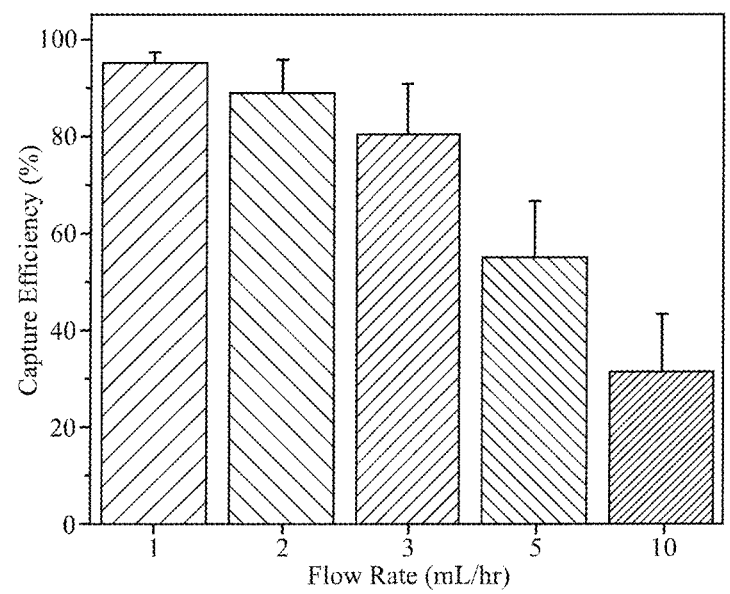
FIG. 32B is a graph showing a cell capture efficiency of the microfluidic polymer-graphene oxide device at various flow rates evaluated using a breast cancer cell line (MCF-7), where error bars show standard deviations (n=6).

To test the performance of the polymer-GO device for CTC capture, fluorescence labeled human breast cancer cell lines MCF-7 cells (1,000 cells/mL) are spiked into a buffer and flow through the GO-polymer device at different flow rates (1 to 10 mL/hr). The captured cells in the device and the non-captured cells collected in the waste are counted. It is found that the capture efficiency decreases with flow rate. As shown in FIG. 32B, the efficiency rapidly decreases at flow rates ≥5 mL/hr. Further, as shown in FIG. 32B, the average capture efficiency is over 88.2% (n=6 at each flow rate) in the 1 to 3 mL/hr range, with the highest capture of about 95.21% at about 1 mL/hr.

Figure 32C:
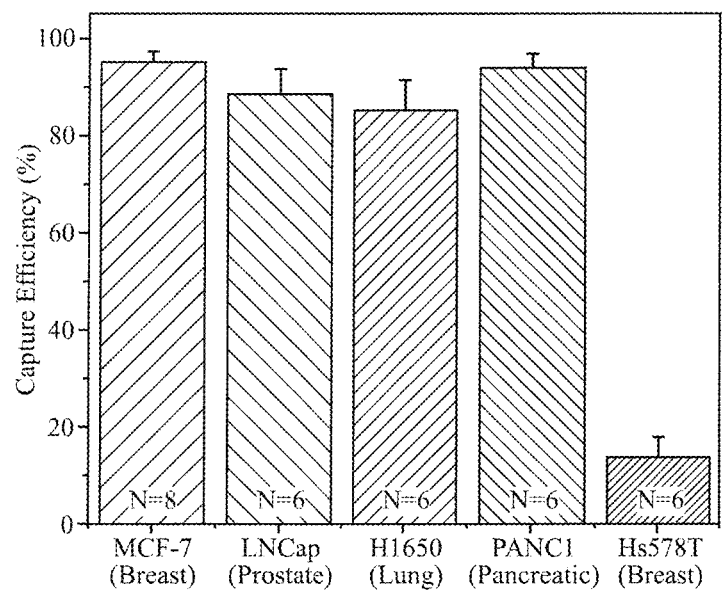
FIG. 32C is a graph showing a capture efficiency of cell lines of varying origin and EpCAM expression levels.

To further investigate the effect of tumor type and EpCAM expression on capture efficiency, three high EpCAM expressing cell lines for various cancer types (MCF-7 breast cancer cells, LNCaP prostate cancer cells, and H1650 lung cancer cells), one low EpCAM expressing cancer-cell line (Panc-1 pancreatic cancer cells), and one EpCAM negative cancer cell lines (Hs578T breast cancer cells) are selected for capture experiments at the flow rate of about 1 mL/hr. The cells are fluorescently labeled and spiked into buffer at a concentration of about 1000 cells/ml. The results are set forth in FIG. 32C, and indicate that the anti-EpCAM-coated GO-polymer device achieves high capture efficiency (about 84.93 to 95.21%) for EpCAM-positive cancer cells. In contrast, a relatively low number of EpCAM-negative cells (Hs578T) are captured. Furthermore, the device is comparably effective in capturing different tumor cells, indicating a robust sensitivity of the device.

Testing of the Performance of the Polymer-GO Device for Cell Release

Figure 32D:
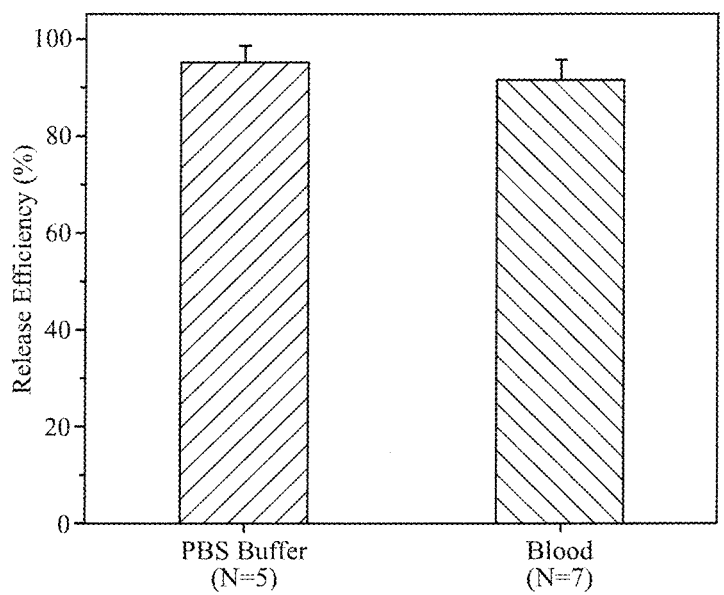
FIG. 32D is a graph showing a release efficiency of the microfluidic polymer-graphene oxide device.
Figure 32E:
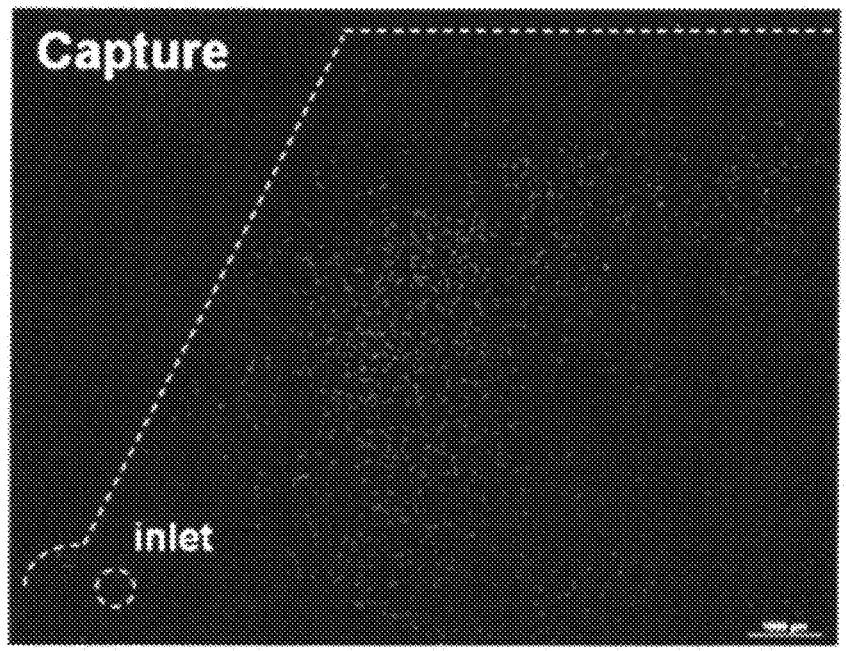
FIGS. 32E-32F are fluorescence microscope images of devices after capture (FIG. 32E) and release (FIG. 32F) of fluorescently-labeled MCF-7 cells.
Figure 32F:
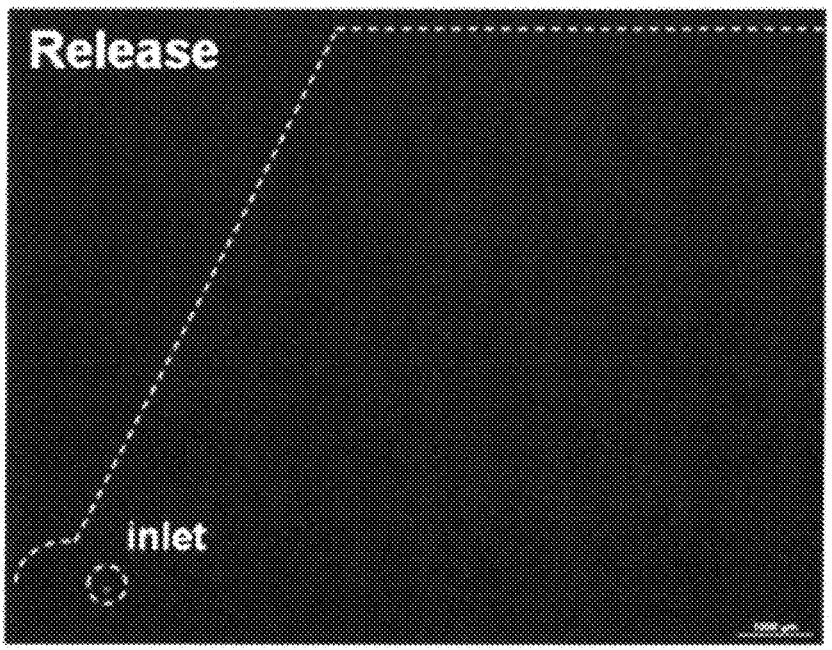

After capturing cells on the devices, cell release experiments are carried out by flowing about 1 mL PBS through the device in a room maintained at about 5° C. at about 100 μL/min. Cell capture is shown in FIG. 32E and cell release is shown in FIG. 32F. Quantification of the cells in the devices before and after release show an average cell release of about 95.21% and about 91.56% in buffer and blood experiments, respectively, as shown in FIG. 32D. As shown in FIG. 32G, the viability of the released cells is also tested by live dead assay, and about 91.68% of the cells remained viable after release.

CTC Capture and Release in Clinical Samples

Figure 33A:
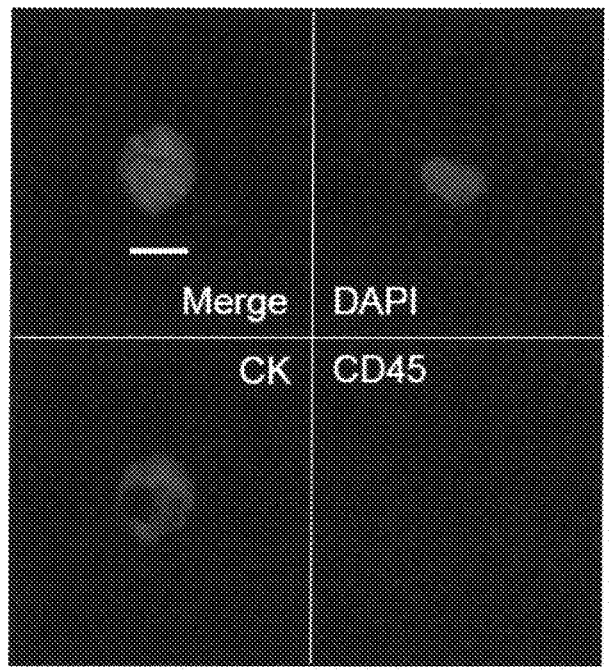
FIG. 33A is a fluorescence image of CTCs from a breast cancer patient sample, where nucleated cells (shown in blue) stain positive for cytokeratin 7/8 (shown in red) and negative for white blood cell marker CD45 (shown in green) are enumerated as CTCs. The scale bar for the fluorescence image is 10 µm.
Figure 33C:
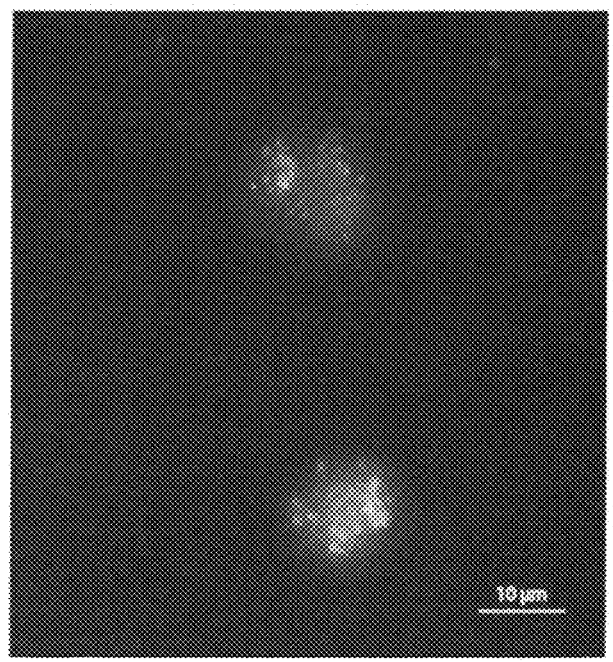
FIG. 33C is a fluorescence in situ hybridization (FISH) image of CTCs of a breast cancer patient, with HER2 shown in green and a centromere 17 probe shown in red.
Figure 33B:
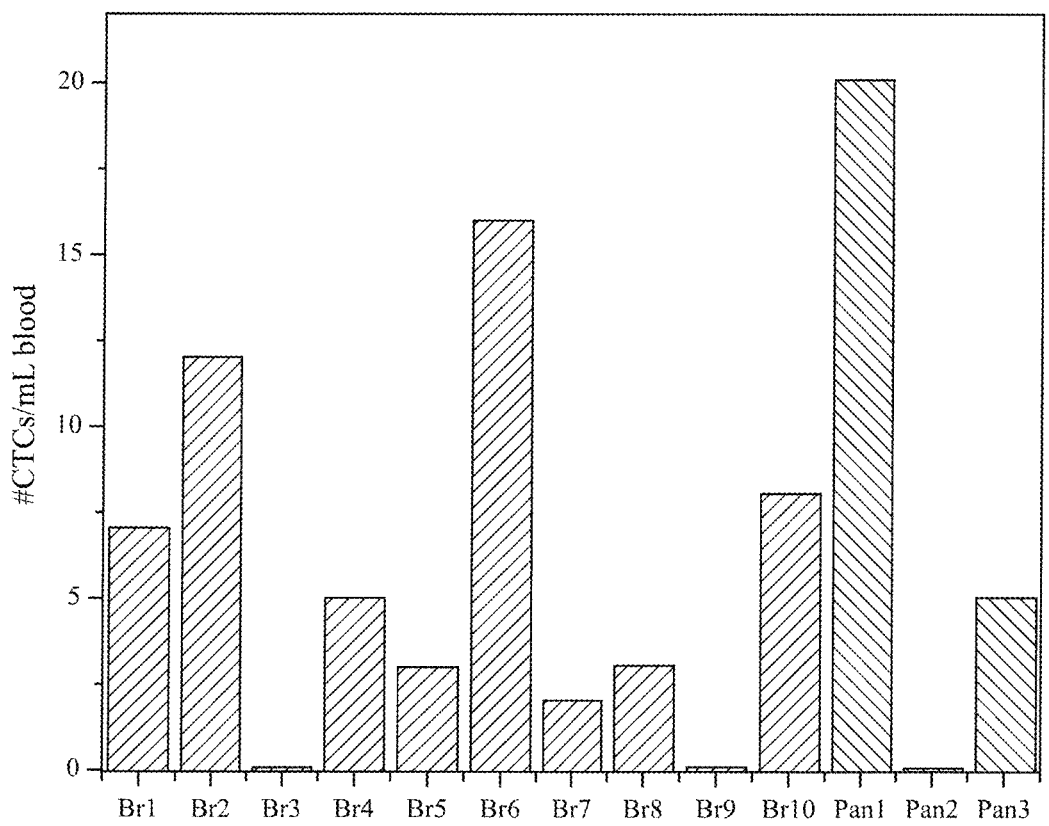
FIG. 33B is a graph showing CTC enumeration results from ten breast cancer patients and three pancreatic cancer patients.

CTC capture and release in clinical samples using the tunable polymer-GO composite film based device is performed as follows. Blood samples obtained from ten metastatic breast cancer patients and three pancreatic cancer patients are prepared. Whole blood samples are collected into EDTA tubes and processed at a flow rate of about 1 mL/hr. Following a washing step, cells are released from the chip and deposited/spun onto glass slides by a cytospin centrifuge. As shown in 33A, CTCs in these samples are identified as DAPI-positive (shown in blue) nucleated cells staining positive for tumor markers (cytokeratin 7/8, visualized with a secondary antibody tagged with Alexa Fluor 546, shown in red) and negative for leukocyte markers (CD45, visualized with a secondary antibody tagged with Alexa Fluor 488, shown in green). CTCs are successfully recovered from 8 breast cancer patient samples and 2 pancreatic cancer patients (ranging from 2 to 20 CTCs/mL), as shown in FIG. 33B. The average number of CTCs recovered from breast samples is 5.6 CTCs/mL and from pancreatic samples is 8.3 CTCs/mL.

Released CTCs are viable and structurally intact, and may be readily investigated by standard clinical cytopathological and genetic testing. The feasibility of detecting HER2 amplification by fluorescence in situ hybridization (FISH) is performed. CTCs released from the chip are subsequently made into "cell blocks" by first fixing the CTCs with ethanol and then embedding the CTCs in Histogel (Thermo Scientific). Blocks are then formalin fixed and stored in 70% ethanol until slide preparation. Blocks are also paraffin embedded and sectioned. FISH is conducted using probes for HER2 (BAC clone RP11-94L15) and chromosome 17 control probe (BAC clone RP11-100E5), revealing HER2 amplification in one breast cancer patient, as shown in FIG. 33C. One green signal indicates the presence of one copy of HER2, while one red signals indicates one copy of centromere 17 probe. Further, the multiple green signals in FIG. 33C imply HER2 amplification.

The downstream analysis facilitated by the efficient release of captured cells highlights the potential for use of the device in basic and clinical cancer investigation. Through the incorporation of a composite that combines the advantages of a temperature-sensitive modality and sensitive nanomaterial-enabled capture, the polymer-GO film that serves as the basis of this technology overcomes some of the key shortcomings of previous CTC capture technologies. As evidenced by data obtained from physiologic solutions containing spiked labeled cancer cells from multiple cancers and the processing of primary breast and pancreatic cancer patient blood samples, isolation of the rare cells with the device is highly feasible.

Compared with other CTC isolation strategies, immunoaffinity based technologies harvest CTCs with high sensitivity and purity, but these technologies have the drawback of tethering cells within the device. To overcoming this limitation, the device of the present disclosure can be used to collect viable and intact CTCs in suspension after immunocapture. This tends to be ideal for various downstream analyses that typically require high integrity and purity of the targeted cell population, such as genotyping and single cell profiling.

One or more of the values described above may vary by +/−5%, +/−10%, +/−15%, +/−20%, etc. so long as the variance remains within the scope of the disclosure. Unexpected results may be obtained from each member of a Markush group independent from all other members. Each member may be relied upon individually and/or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

What is claimed is:

1. A system for detecting cells in a fluid, said system comprising:
   a substrate; and
   a mixture disposed on said substrate and comprising a carrier for capturing the cells and a copolymer including a thermo-responsive polymer copolymerized with a monomer that is one of more hydrophobic or more hydrophilic than said thermo-responsive polymer and said copolymer having a lower critical solution temperature (LCST) tunable based on a ratio of said thermo-responsive polymer and said monomer in said copolymer, wherein said copolymer is adapted to release said carrier with the cells when a temperature of said system is below said lower critical solution temperature (LCST) of said copolymer, wherein said carrier is graphene oxide or a nanoparticle.

2. The system as set forth in claim 1 wherein the thermo-responsive polymer has a matrix and said carrier is embedded in said matrix of said thermo-responsive polymer.

3. The system as set forth in claim 1 wherein said copolymer comprises i) a homo-polymer selected from the group consisting of a poly(N-alkyl acrylamide), a poly(N-vinylalkylamide), a poly(vinyl ether), a poly(oxazoline), a poly(N-vinylcaprolactam), a poly(N-vinylpyrrolidone), a poly(N-ethylpyrrolidine methacrylate), and a poly(N-acryloylpyrrolidine) and ii) a hydrophilic monomer.

4. The system as set forth in claim 1 wherein said copolymer comprises i) N-isopropylmethylacrylamide and ii) a methylacrylamide monomer with labile hydrazone linkage.

5. The system as set forth in claim 1 wherein said copolymer includes i) poly(di(ethylene glycol) ethyl ether acrylate) and ii) (oligoethylene glycol acrylate).

6. The system as set forth in claim 1 wherein said copolymer is poly(N-acryloyl piperidine-co-N,N-diethylacrylamide).

7. The system as set forth in claim 1 wherein said copolymer is poly(vinyl alcohol-co-vinyl acetal).

8. The system as set forth in claim 1 wherein said copolymer is poly(glycidol-co-glycidol acetate).

9. The system as set forth in claim 1 wherein said carrier is a functionalized graphene oxide.

10. The system as set forth in claim 9 wherein said functionalized graphene oxide is graphene oxide including a functionalization comprising a binding agent for interaction with the cells to capture the cells when the cells come into contact with the functionalized graphene oxide.

11. A method for detecting cells using the system of claim 1, said method comprising the steps of:
    providing the system of claim 1; and
    introducing a sample of fluid containing the cells into the system such that the sample interacts with the carrier for capturing the cells.

12. The method as set forth in claim 11 wherein the carrier is the graphene oxide and said method further comprises the step of releasing the captured cells attached to the functionalized graphene oxide when a temperature of the system is below a lower critical solution temperature (LCST) of the thermo-responsive polymer.

* * * * *